US010098943B2

(12) United States Patent
Akahata et al.

(10) Patent No.: US 10,098,943 B2
(45) Date of Patent: Oct. 16, 2018

(54) FLAVIVIRUS VIRUS LIKE PARTICLE

(71) Applicant: VLP Therapeutics, LLC, Wilmington, DE (US)

(72) Inventors: Wataru Akahata, Kensington, MD (US); Ryuji Ueno, Easton, MD (US)

(73) Assignee: VLP Therapeutics, LLC, Wilmington, DE (US)

( * ) Notice: Subject to any disclaimer, the term of this patent is extended or adjusted under 35 U.S.C. 154(b) by 0 days.

(21) Appl. No.: 14/850,399

(22) Filed: Sep. 10, 2015

(65) Prior Publication Data

US 2016/0074501 A1    Mar. 17, 2016

Related U.S. Application Data

(60) Provisional application No. 62/048,897, filed on Sep. 11, 2014.

(51) Int. Cl.
| | |
|---|---|
| *A61K 39/12* | (2006.01) |
| *C07K 14/005* | (2006.01) |
| *C12N 7/00* | (2006.01) |
| *A61K 39/00* | (2006.01) |

(52) U.S. Cl.
CPC .......... *A61K 39/12* (2013.01); *C07K 14/005* (2013.01); *C12N 7/00* (2013.01); *A61K 2039/5258* (2013.01); *A61K 2039/53* (2013.01); *A61K 2039/575* (2013.01); *C12N 2770/24023* (2013.01); *C12N 2770/24123* (2013.01); *C12N 2770/24134* (2013.01); *Y02A 50/386* (2018.01); *Y02A 50/388* (2018.01); *Y02A 50/39* (2018.01); *Y02A 50/394* (2018.01); *Y02A 50/396* (2018.01)

(58) Field of Classification Search
None
See application file for complete search history.

(56) References Cited

U.S. PATENT DOCUMENTS

| | | |
|---|---|---|
| 5,439,809 A | 8/1995 | Guillaumet et al. |
| 5,580,773 A | 12/1996 | Kang et al. |
| 5,629,204 A | 5/1997 | Honjo et al. |
| 5,698,520 A | 12/1997 | Honjo et al. |
| 5,939,598 A | 8/1999 | Kucherlapati et al. |
| 7,101,550 B2 | 9/2006 | Wood et al. |
| 7,595,048 B2 | 9/2009 | Honjo et al. |
| 7,790,181 B2 | 9/2010 | Platteborze et al. |
| 9,249,191 B2 | 2/2016 | Ueno et al. |
| 9,363,353 B1 | 6/2016 | Chik |
| 2003/0108521 A1 | 6/2003 | Calatrava |
| 2005/0214321 A1 | 9/2005 | Rasochova et al. |
| 2007/0122378 A1 | 5/2007 | Freeman et al. |
| 2009/0298955 A1 | 12/2009 | Handa et al. |
| 2009/0305950 A1 | 12/2009 | Minato et al. |
| 2009/0312190 A1 | 12/2009 | Chinea Santiago et al. |
| 2011/0027306 A1 | 2/2011 | Rayner et al. |
| 2011/0081341 A1 | 4/2011 | Honjo et al. |
| 2011/0207223 A1 | 8/2011 | Tang et al. |
| 2011/0318373 A1 | 12/2011 | Sasikumar et al. |
| 2012/0003266 A1 | 1/2012 | Nable et al. |
| 2013/0251744 A1 | 9/2013 | Ueno et al. |
| 2014/0120125 A1 | 5/2014 | Ella et al. |
| 2014/0127247 A1 | 5/2014 | Dubensky, Jr. et al. |
| 2014/0363458 A1 | 12/2014 | Ueno et al. |
| 2015/0017194 A1 | 1/2015 | Akahata et al. |
| 2016/0040134 A1 | 2/2016 | Akahata et al. |
| 2016/0200775 A1 | 7/2016 | Akahata et al. |

FOREIGN PATENT DOCUMENTS

| | | |
|---|---|---|
| CN | 102321639 | 1/2012 |
| CN | 106085974 | 11/2016 |
| JP | 4506301 | 11/1992 |
| JP | 2007512842 | 5/2007 |
| JP | 2007-537761 A | 12/2007 |
| JP | 2008543774 | 12/2008 |
| WO | 9310152 | 5/1993 |
| WO | 9712048 | 4/1997 |
| WO | 9941383 A1 | 8/1999 |
| WO | 2002096939 | 12/2002 |
| WO | 03/102166 A2 | 12/2003 |
| WO | 2004043399 | 5/2004 |
| WO | 2006040334 | 4/2006 |
| WO | 2006088229 | 8/2006 |
| WO | 2007003384 | 1/2007 |
| WO | 2007059715 A2 | 5/2007 |
| WO | 2007100098 | 9/2007 |
| WO | 2008025067 | 3/2008 |
| WO | 2009079185 | 6/2009 |
| WO | 2010062396 | 6/2010 |
| WO | 2011035004 | 3/2011 |
| WO | 2012006180 | 1/2012 |
| WO | 2012023995 | 2/2012 |

(Continued)

OTHER PUBLICATIONS

Lin et al., PLOS, 2012, 6(1):e1337, 12 pages.*
Zhang et al., Virology Journal, 2011, 8:333, 9 pages.*
http://www.who.int/immunization/research/development/dengue vaccines/en/ (3 pages).
Vaccine 30 (2012) 4301-4306.
Expert Rev. Vaccines 9(10), 1149-1176, 2010.
Tsai et al., Journal of Virology, 2015 89: 7348-7362.
Huang Claire Y.H., et al., Virology, 2010, vol. 396, No. 2, pp. 305-315, ISSN:0042-6822, Table1, Fig.5, pp. 310-313.
De Wispelaere Melissanne, et al., J. Virol., 2012, vol. 86, No. 13, pp. 7072-7083, ISSN:0022-538X, Abstract, Fig.1, Fig.8-9, p. 7073.
Purdy E. David, et al., Virology, 2005, vol. 333, No. 2, pp. 239-250, ISSN: 0042-6822, Abstract, Fig.1-4. Table 1, pp. 240, 247-248.
Hsieh Szu-Chia, et al., Virology, 2008, vol. 374, No. 2, pp. 338-350, ISSN: 0042-6822.

(Continued)

*Primary Examiner* — Stacy B Chen
(74) *Attorney, Agent, or Firm* — Sughrue Mion, PLLC

(57) ABSTRACT

Provided is a virus like particle comprising one or more flavivirus structural proteins, and a composition or vaccine comprising thereof, its use in the prevention or treatment of flavivirus infection. The flavivirus structural protein contains at least one amino acid alteration in the envelope region. Examples of flavivirus contains dengue virus.

16 Claims, 3 Drawing Sheets

Specification includes a Sequence Listing.

(56) References Cited

FOREIGN PATENT DOCUMENTS

| WO | 2012106356 | 8/2012 |
| --- | --- | --- |
| WO | 2012123755 | 9/2012 |
| WO | 2012172574 | 12/2012 |
| WO | 2013/009884 A1 | 1/2013 |
| WO | 2013063248 A1 | 5/2013 |
| WO | 20130122262 | 5/2013 |
| WO | 2013151764 A1 | 10/2013 |
| WO | 2015005500 | 1/2015 |
| WO | 2015139784 | 9/2015 |
| WO | 2016021209 | 2/2016 |
| WO | 2016109792 A2 | 7/2016 |
| WO | 2016199936 | 12/2016 |
| WO | 2016210127 | 12/2016 |
| WO | 2017009873 | 1/2017 |
| WO | 2017015463 | 1/2017 |

OTHER PUBLICATIONS

Khetarpal Niyati, et al., J. Nanobiotechnology, 2013, vol. 11, No. 15, 8 pages, ISSN: 1477-3155.
Communication dated Dec. 15, 2015 from the International Searching Authority in counterpart International application No. PCT/JP2015/004623.
Adams et al., "The expression of hybrid H1V:Ty virus-like particles in yeast", Nature, 329(6134):68-70 (1987).
Agata et al., "Expression of the PD-1 antigen on the surface of stimulated mouse T and B lymphocytes", International Immunology, 8(5):765-772 (1996).
Akahata et al., "A VLP vaccine for epidemic Chikungunya virus protects non-human primates against infection", Nat. Med., 16(3):334-338 (2010).
Allsopp et al., "Comparison of numerous delivery systems for the induction of cytotoxic T lymphocytes by immunization", Eur. J. Immunol., 26(8):1951-1959 (1996).
Arora et al., "Virus-like particles displaying envelope domain III of dengue virus type 2 induce virus-specific antibody response in mice", Vaccine, 31(6)873-878 (2013).
Atkins et al., "Therapeutic and prophylactic applications of alphavirus vectors", Expert Reviews in Molecular Medicine, 10(e33):1-17 (2008).
Birkett et al. "A Modified Hepatitis B Virus Core Particle Containing Multiple Epitopes of the *Plasmodium falciparum* Circumsporozoite Protein Provides a Highly immunogenic Malaria Vaccine in Preclinical Analyses in Rodent and Primate Hosts", Infection and Immunity, American Society for Microbiology, US, 70(12): 6860-6870 (2002).
Bonaldo et al., "Surface expression of an immunodominant malaria protein B cell epitope by yellow fever virus", J. Mol. Biol., 315(4):873-885 (2002).
Calvo-Calle et al., "A Linear Peptide Containing Minimal T- and B-Cell Epitopes of *Plasmodium falciparum* Circumsporozoite Protein Elicits Protection against Transgenic Sporozoite Challenge", Infection and Immunity, 74(12):6929-6939 (2006).
Carvalho et al., "Malaria Vaccine: Candidate Antigens, Mechanisms, Constraints and Prospects", Scand. J. Immunol., Blackwell Science Ltd., 56:327-343 (2002).
Chackerian et al., "Determinants of Autoantibody Induction by Conjugated Papillomavirus Virus-Like Particles", The Journal of Immunology, 169(11):6120-6126 (2002) (7 pages total).
Charoensri et al., "An optimized expression vector for improving the yield of dengue virus-like particles from transfected insect cells" Journal of Virological Methods, 205:116-123 (2014).
Cox et al. "Predicting Zika virus structural biology: Challenges and opportunities for intervention", Antiviral Chemistry and Chemotherapy, 24(3-4):118-126 (2015).
Crompton et al., "Advances and challenges in malaria vaccine development", Science in medicine, The Journal of Clinical Investigation, 120(12):4168-4178 (2010).

Dobano et al., "Alphavirus replicon particles are highly immunogenic in the murine Malaria model by homologous or heterologous immunization", Open Vaccine Journal, 1:27-37 (2008).
Elshuber et al., "Cleavage of protein prM is necessary for Infection of BHK-21 cells by tick-borne encephalitis virus", Journal of General Virology, 84:183-191 (2003).
Elshuber et al., "Resuscitating Mutations in a Furin Cleavage-Deficient Mutant of the Flavivirus Tick-Borne Encephalitis Virus", Journal of Virology, 79(18):11813-11823 (2005).
Federico, "Virus-like particles show promise as candidates for new vaccine strategies", Future Virol., 5(4):371-374 (2010).
GenBank Accession No. AAB02517.1, "Structural polyprotein precursor, Venezuelan equine encephalitis virus," retrieved from https://www.ncbi.nlm.nih.gov/protein/AAB02517.1, dated Nov. 17, 2004.
GenBank Accession No. ADG95942.1 structural polyprotein [Chikungunya virus], retrieved from http://www.ncbi.nlm.nih.gov/protein/296124572?report=genbank&log$=protalign&blast_rank=2&FID=PBR7NTOU015, dated Dec. 28, 2010.
"Gen Bank Accession No. AAW78190.1," circumsporozoite protein, partial [*Plasmodium falciparum*] retrieved from http://www.ncbi.nlm.nih.gov/brotein/58429573?report=genbank&log$=protalign&biast_rank=18&RID=P92DMO5R01R, dated Dec. 29, 2006.
GenBank Accession No. AY632535.2, "Zika virus strain MR 766, complete genome" AY632535.2, 6 pages total [retrieved on May 16, 2017] from https://www.ncbi.nlm.nih.gov/nuccore/AY632535, dated Nov. 23, 2010.
Ghasparian et al., "Engineered synthetic virus-like particles and their use in vaccine delivery", Chembiochem., 12(1):100-109 (2011).
Gilbert et al., "A protein particle vaccine containing multiple Malaria epitopes", Nat. Biotechnol., 15(12):1280-1284 (1997).
Gorchakov et al., "Comparative analysis of the alphavirus-based vectors expressing Rift Valley fever virus glycoproteins", Virology, 366: 212-225 (2007).
Gregson et al. "Phase 1 Trial of an Alhydrogel Adjuvanted Hepatitis B Core Virus-Like Particle Containing Epitopes of *Plasmodium falciparum* Circumsporozoite Protein", PLoS ONE, 3(2):e1556 (2008).
Grgacic et al., "Virus-like particles: Passport to immune recognition", Methods, 40:60-65 (2006).
Haddow et al., "Genetic Characterization of Zika Virus Strains: Geographic Expansion of the Asian Lineage", PLOS Neglected Tropical Disease, 6(2):e1477 (2012).
Hevey et al., "Marburg Virus Vaccines Based upon Alphavirus Replicons Protect Guinea Pigs and Nonhuman Primates", Virology, 251:28-37 (11 pages total) (1998).
Hsieh et al.. "The length of and nonhydrophobic residues in the transmembrane domain of dengue virus envelope protein are critical for its retention and assembly in the endoplasmic reticulum", Journal of Virology, 84(9):4782-4797 (2010).
Jennings et al., "Immunodrugs: Therapeutic VLP-Based Vaccines for Chronic Diseases", Annu. Rev. Pharmacol. Toxicol., 49:303-326 (2009).
Jones et al., "A plant-produced Pfs25 VLP Malaria Vaccine Candidate Induces Persistent Transmission Blocking Antibodies against *Plasmodium falciparum* in immunized mice", PLoS One, 8(11):e79538, do1:10.1371/journal.pone.0079538 (Nov. 18, 2013).
Zika virus fact sheet, URL:http://www.who.int/mediacentre/factsheets/zika/en/ (5 pages total), updated Sep. 6, 2016.
Kuo et al., "Cell-based analysis of Chikungunya virus E1 protein in membrane fusion", J. Biomed. Sci., 19(44):1-12 (2012).
Larocca et al., "Vaccine Protection Against Zika Virus from Brazil", doi:10.1038/nature18952 (24 pages total), Nature, 536(7617):474-478 (2016).
Lechner et al., "Virus-like particles as a modular system for novel vaccines", Intervirology, 45(4-6):212-217 (2002).
Leibl et al., "Adjuvant/carrier activity of inactivated tick-borne encephalitis virus", Vaccine, 16(4):340-345 (1998).
Malaria Vaccine Program, http://www.globalvaccines.org/content/malaria+vaccine+program/19614, 4 pages total (2012).
McCoy et al., "Cytotoxic T Lymphocyte-associated Antigen 4 (CTLA-4) Can Regulate Dendritic Cell-induced Activation and Cytotoxicity of CD8+ T Cells Independently of CD4+ T Cell Help", J. Exp. Med., 189(7):1157-1162 (1999).

(56) References Cited

OTHER PUBLICATIONS

Mellman et al., "Cancer immunotherapy comes of age", Nature, 480:480-489 (2011).
Milich et al. "Conversion of poorly immunogenic malaria repeat sequences into a highly immunogenic vaccine candidate", Vaccine, Elsevier Ltd. GB, 20(5-6):771-788 (2002).
Notka F et al., "Accelerated clearance of SHIV in rhesus monkeys by virus-like particle vaccines is dependent on induction of neutralizing antibodies", Vaccine, 18(3-4):291-301 (2000).
Oliveira et al., "Safety and enhanced immunogenicity of a Hepatitis B core practical *Plasmodium falciparum* Malaria vaccine formulated in adjuvant montanide ISA 720 in a Phase I Trial", Infect. Immun., 73(6):3587-3597 (2005).
Oliveira-Ferreira et al., "Immunogenicity of Ty-VLP bearing a CD8 (+) T cell epitope of the CS protein of *P. yoelii*: enhanced memory response by boosting with recombinant vaccinia virus", Vaccine, 18(17):1863-1869 (2000).
Ozden et al., "Inhibition of Chikungunya Virus Infection in Cultured Human Muscle Cells by Furin Inhibitors", Journal of Biological Chemistry, vol. 283, No. 32 (10 pages total) (Aug. 8, 2008).
Palomba et al., "CD8+ T-Cell-Dependent Immunity Following Xenogeneic DNA Immunization against CD20 in a Tumor Challenge Model of B-Cell Lymphoma", Clinical Cancer Research, 370(11):370-379 (2005).
Pfeiffer et al., "A virosome-mimotope approach to synthetic vaccine design and optimization: synthesis, conformation, and immune recognition of a potential Malaria-vaccine candidate", Angew. Chem. Int. Ed., 42(21):2368-2371 (2003).
Pushko et al, "Replicon-Helper Systems from Attenuated Venezuelan Equine Encephalitis Virus: Expression of Heterologous Genes in Vitro and Immunization against Heterologous Pathogens in Vivo", Virology, 239:389-401 (1997).
Richner et al., "Modified mRNA vaccines protect against Zika Virus infection", Cell, 168:1114-1125 (23 pages total) (2017).
Roberts et al, "Vaccination with CD20 peptides induces a biologically active, specific immune response in mice", Blood, 99:3748-3755 (2002).
Rodrigues et al., "Influenza and Vaccinia viruses expressing Malaria CD8+T and B Cell epitopes. Comparison of their immunogenicity and capacity to induce protective immunity", J. Immunol., 153(10):4636-4648 (1994).
Rodriguez et al., Vaccine Efficacy against malaria by the Combination of Porcine Parvovirus-Like Particles and Vaccinia Virus Vectors Expressing CS of Plasmodium, PLoS One, 7(4):e34445 (2012).
Roldao et al., "Virus-like particles in vaccine development", Expert Rev., Vaccines, 9(10):1149-1176 (2010).
Shiratsuchi et al., "Replacing adenoviral vector HVR1 with a malaria B cell epitope improves immunogenicity and circumvents preexisting immunity to adenovirus in mice", Journal of Clinical Investigation, 120(10):3688-3701 (2010).
Sun et al: "Structural analyses at pseudo atomic resolution of Chikungunya virus and antibodies show mechanisms of neutralization", eLIFE, 2:1-27 (2013).
Spohn et al., "A Virus-Like Particle-Based Vaccine Selectively Targeting Soluble TNF—a Protects from Arthritis without Inducing Reactivation of Latent Tuberculosis", The Journal of Immunology, 178:7450-7457 (8 pages total) (2007).
Taylor et al., "Production of immunogenic West Nile virus-like particles using a herpes simplex virus 1 recombinant vector", Virology, 496:186-193 (2016).
Vuola et al., "Differential immunogenicity of various heterologous prime-boost vaccine regimens using DNA and viral vectors in healthy volunteers", J. Immunol., 174(1):449-455 (2005).
Yamaji et al. "Efficient production of Japanese encephalitis virus-like particles by recombinant lepidopteran insect cells", Appl. Microbiol Biotechnol., 97:1071-1079 (2013).
Communication dated Dec. 20, 2017, issued by the European Patent Office in counterpart European Patent Application No. 15829311.8.
Urakami et al., "Development of a Novel Virus-Like Particle Vaccine Platform That Mimics the Immature Form of Alphavirus," Clinical and Vaccine Immunology, 24(7): e00090-17 (pp. 1-14), (2017).
Veltrop-Duits et al., "Human CD4+ T cells stimulated by conserved adenovirus 5 hexon peptides recognize cells infected with different species of human adenovirus", Eur. J. Immunol., 2006, vol. 36, pp. 2410-2423 (14 pages total).
Communication, dated Apr. 11, 2018, issued by the European Patent Office in counterpart European Application No. 15840429.3.
Communication, dated May 15, 2018, issued by the Japanese Patent Office in counterpart Japanese Application No. 2016-501252.
Akane Urakami et al., "An Envelope-Modified Tetravalent Dengue Virus-Like-Particle Vaccine Has Implications for Flavivirus Vaccine Design", Journal of Virology, Dec. 2017, vol. 91, Issue 23, e01181-17 (16 pages total).
Palucha, Andrzej, et al., "Virus-Like Particles: Models for Assembly Studies and Foreign Epitope Carriers" Progress in Nucleic Acid Research and Molecular Biology, 2005, vol. 30, pp. 135-168.

* cited by examiner

Figure 1

DENV Genome: C, prM, E (Structural protein); NS1, NS2A, NS2B, NS3, NS4A, NS4B, NS5 (Nonstructural protein)

DENV VLP Construct: prM, E

C: Capsid, E: Envelope, prM: precursor Membrane protein

Figure 2

| Capsid | DENV2Capsid-R85A K86A | | |
|---|---|---|---|
| prME | DENV2 prM E (WT) | Chimera DENV2 prM E _3'DENV1 E | Chimera DENV2 prM E _3'DENV1 E F108A |

100k-
75k-
50k-

FLAVIVIRUS VIRUS LIKE PARTICLE

CROSS REFERENCE TO RELATED APPLICATIONS

This application claims the benefit of U.S. Provisional Application No. 62/048,897 filed Sep. 11, 2014. The contents of this provisional application are herein incorporated by reference.

TECHNICAL FIELD

The present application relates to a virus like particle comprising one or more flavivirus structural proteins, and a composition or vaccine comprising thereof, its use in medicine, particularly in the prevention or treatment of flavivirus infection.

BACKGROUND ART

Flavivirus comprise more than 70 different viruses, many of which are arthropod-borne and transmitted by either mosquitoes or ticks.

Flavivirus is a genus of viruses in the family Flaviviridae. This genus includes the West Nile virus (WNV), dengue virus (DENV), tick-borne encephalitis virus (TBEV), yellow fever virus (YFV), Japanese encephalitis virus (JEV), hepatitis C virus (HCV) and several other viruses which may cause encephalitis or haemorrhagic diseases.

Dengue fever is a mosquito-borne disease caused by the flavivirus and has spread to most tropical and many subtropical areas. The disease is caused by four closely related viruses, the Dengue virus 1 including subtypes I to IV, Dengue virus 2 including subtypes Asian I, Asian II, Cosmopolitan, American and American/Asian, Dengue virus 3 including subtypes I to IV and Dengue virus 4 including subtypes I to III. Although Dengue is the most important flavivirus with respect to global disease incidence, the development and use of vaccines against the virus has been hampered so far by the theoretical risk of vaccine-related adverse events such as immune enhancement of infection and the requirement to induce a long-lasting protective immune response against all four dengue serotypes simultaneously.

There is no effective dengue therapeutic and prevention against dengue fever is currently limited to vector control measures. A dengue vaccine would therefore represent a major advance in the control of the disease.

While no licensed dengue vaccine is available, several vaccine candidates are currently evaluated in clinical studies. WHO indicates that the growing global epidemic of dengue is of mounting concern, and a safe and effective vaccine is urgently needed. www.who.int/immunization/research/development/dengue_vaccines/en/) and Vaccine 30 (2012) 4301-4306).

Virus-like particles (VLPs) are multiprotein structures that mimic the organization and conformation of authentic native viruses but non-infectious because they do not contain any viral genome, potentially yielding safer vaccine candidates. A handful of prophylactic VLP-based vaccines is currently commercialized worldwide: GlaxoSmithKline's Engerix® (hepatitis B virus) and Cervarix® (human papillomavirus), and Merck and Co., Inc.'s Recombivax HB® (hepatitis B virus) and Gardasil® (human papillomavirus) are some examples. Other VLP-based vaccine candidates are in clinical trials or undergoing preclinical evaluation, such as, influenza virus, parvovirus, Norwalk and various chimeric VLPs. Many others are still restricted to small-scale fundamental research, despite their success in preclinical tests. The implications of large-scale VLP production are discussed in the context of process control, monitorization and optimization. The main up- and down-stream technical challenges are identified and discussed accordingly. Successful VLP-based vaccine blockbusters are briefly presented concomitantly with the latest results from clinical trials and the recent developments in chimeric VLP-based technology for either therapeutic or prophylactic vaccination.

Up to now, VLP-based vaccines have been produced for more than 30 different viruses that infect human and other animals. The examples include AAV (Adeno-associated virus), H5N3 (Avian influenza), BFDV (Budgerigar fledgling disease virus), BTV (Bluetongue virus), Ebola, Enterovirus 71, GHPV (Goose hemorrhagic polyoma virus), HBV (Hepatitis B virus), HCV (Hepatitis C virus), HDV (Hepatitis δ virus), HEV (Hepatitis E virus), HIV, HPV (Human papillomavirus), IBDV (Infectious bursal disease virus), Influenza A, Influenza A H1N1, Influenza A H3N2, JC polymavirus, Margurg, MS2, IPCV (Indian peanut clump virus), NDV (Newcastle disease virus), No (Norovirus) Nv (Norwalk virus), PhMV (Physalis mottle virus), Polymavirus, PPV (Porcine parvovirus), RHDV (Rabbit hemorrhagic disease virus), Rotavirus, SARS, SIV (Simian immunodeficiency virus), SV40 (Simian virus 40), SVDV (Swine vesicular disease virus) and so on. (Expert Rev. Vaccines 9(10), 1149-1176, 2010).

SUMMARY OF THE INVENTION

In a first aspect, the present application provides a virus like particle comprising one or more flavivirus structural proteins, wherein the envelope region of the flavivirus structural protein contains at least one alteration in the amino acid sequence.

In a second aspect, the present application provides a nucleic acid molecule comprising or consisting of a nucleotide sequence that encodes the flavivirus structural protein contained in the virus like particle provided in the first aspect of the present application.

In a third aspect, the present application provides a composition or vaccine comprising the virus like particle provided in the first aspect and/or the nucleic acid molecule provided in the second aspect.

In a fourth aspect, the present application provides a method of producing an antibody or anti-serum comprising a neutralizing antibody, comprising contacting the virus like particle provided in the first aspect of the present application and/or the nucleic acid molecule provided in the second aspect of the present application to a mammal.

In a fifth aspect, the present application provides a method of treating or preventing flavivirus infection or a method of inducing and/or enhancing immune response against a flavivirus in a mammal, comprising administering the composition provided in the third aspect of the present application to the mammal.

In a sixth aspect, the present application provides a method of producing the virus like particle provided in the first aspect of the present application, comprising: culturing a cell which is transfected with a gene encoding the at least one flavivirus structural proteins contained in the virus like particle; and recovering virus like particle from the cell culture. This aspect may further comprise the step of preparing a gene comprising a nucleotide sequence encoding the at least one flavivirus structural proteins contained in the virus like particle.

In a seventh aspect, the present application provides a virus like particle for use in a method or kit of diagnosing flavivirus infection in a mammal.

BRIEF DESCRIPTION OF DRAWINGS

FIG. 1 shows the construction of Dengue virus genome and one example of dengue VLP construct.

FIG. 2 shows envelope proteins in the supernatants measured by Western Blotting. Expression vector for viral structural protein comprising Dengue type 2 virus prM and envelope protein, or for a viral structural protein comprising Dengue type 2 virus prM and a chimera of Dengue type 2 and Dengue type 1, wherein the C-terminal region of the Dengue virus type 2 envelope protein was replaced to the corresponding Dengue virus type 1 C-terminal region (199aa-676aa of SEQ ID NO: 8), or a viral structural protein containing the chimeric envelope region wherein one amino acid alteration in the chimeric envelope region (F108K, at 289aa of SEQ ID NO: 10) was introduced, and an expression vector for Dengue virus type 1 capsid protein were transfected to 293F cells. Western blotting using antibody against Dengue Envelope protein was conducted against the culture supernatant.

Figure 3:
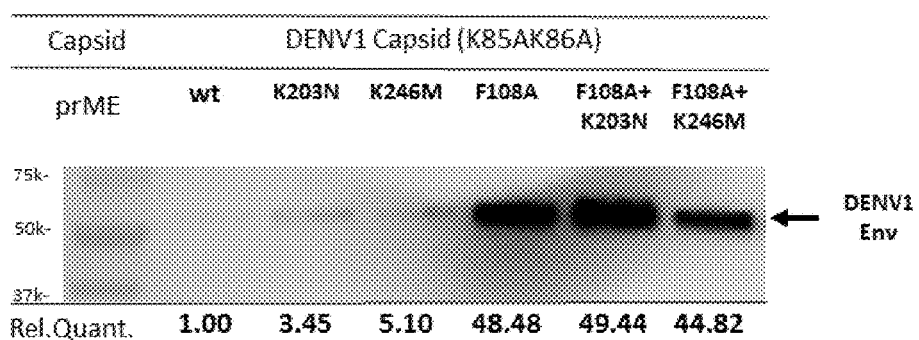
FIG. 3 shows results of Western Blotting. An expression vector for viral structural protein comprising Dengue type 1 virus prM and envelope with or without alteration (wild type, F108A, K203M, K246M, F108A+K246M or F108A+K203N together with expression vector for Dengue type 1 Capsid protein were transfected to 293F cells. Western blotting using antibody against Dengue Envelope protein was conducted against the culture supernatant.

DESCRIPTION OF EMBODIMENTS (1) A Virus Like Particle Comprising One or More Flavivirus Structural Proteins In the first aspect, the present application provides a virus like particle comprising one or more flavivirus structural proteins, wherein at least one amino acid in the envelope region is altered from its naturally occurred structure.

Flavivirus may be West Nile virus, Dengue virus, tick-borne encephalitis virus, yellow fever virus, Japanese encephalitis, and hepatitis C virus (HCV). Preferred flavivirus is Dengue virus. Dengue virus may be Dengue virus 1 including subtypes I to IV, Dengue virus 2 including subtypes Asian I, Asian II, Cosmopolitan, American and American/Asian, Dengue virus 3 including subtypes I to IV and Dengue virus 4 including subtypes I to III. In the specification and claims, the term "flavivirus structural protein or fragment thereof", refers any peptide-based sequence derived from flavivirus that can be recognized by the immune system in a subject, and/or that stimulates a cell-mediated immune response in a subject and/or stimulates the generation of antibodies in a subject.

As shown in FIG. 1, Dengue virus structural protein consists of capsid protein, precursor membrane protein and envelope protein. In this embodiment, VLP comprises at least one of those structural proteins and preferably, a precursor membrane protein (prM) and an envelope protein. The Dengue virus structural protein may further comprise an amino acid corresponding to the initiation codon and a signal sequence to the amino terminal of the prM sequence.

The region comprising at least one amino acid alternation may be preferably between amino acid position 182 and amino acid position 676, more preferably between amino acid position 271 and amino acid position 302, especially between amino acid position 280 and amino acid position 291, particularly 289 of a protein of SEQ ID NO: 21 which comprises initiation codon M and signal peptide of SEQ ID NO: 17 followed by prM and envelope region of Dengue Virus 1 (WestPac strain, GenBank Accsession No: U88535), or between the positions determined as the above-identified positions when the amino acid sequence of a protein comprising initiation codon M, signal peptide followed by prM and envelope region of a flavivirus or a fragment thereof is aligned with the amino acid sequence represented by SEQ ID NO: 21.

The envelope region of the dengue virus type 1 amino acid sequence is represented by SEQ ID NO: 20. Accordingly, the region comprising at least one amino acid alternation may be in this sequence, preferably between amino acid position 90 and amino acid position 121, especially between amino acid position 99 and amino acid position 110, particularly 108 of a protein of SEQ ID NO: 20, or between the positions determined as the above-identified positions when the amino acid sequence of an envelope of a flavivirus or a fragment thereof is aligned with SEQ ID NO: 20.

As used herein, "a position corresponding to" or recitation that nucleotides or amino acid positions "correspond to" nucleotides or amino acid positions in a disclosed sequence, such as set forth in the Sequence listing, refers to nucleotides or amino acid positions identified upon alignment with the disclosed sequence to maximize identity using a standard alignment algorithm. By aligning the sequences, one skilled in the art can identify corresponding residues.

Viral structural proteins of various flavivirus such as dengue virus types 1-4 have been identified and available at various public databases such as GenBank database. For example, Dengue virus type 1 (WestPac strain): Accession No. U88535, Dengue virus type 2 (S1 vaccine strain): Accession No. M19197, Dengue virus type 3 (strain Singapore 8120/95): Accession No. AY766104 and Dengue virus type 4 (strain ThD4_0476_97): Accession No. Y618988. According to this application, envelope protein of a flavivirus such as dengue virus may be obtained from a database and aligned with SEQ ID NO: 20 to identify a position between the positions corresponding to amino acid position 90 and amino acid position 121 of SEQ ID NO: 20, such as a position corresponding to at amino acid position 108 of SEQ ID NO: 20.

With the exception of comprising at least one amino acid alteration in the envelope region, a flavivirus structural protein contained in the virus like particle may be a naturally occurring viral structural protein or a modified protein thereof. In one embodiment, the modified protein has at least 70%, 75%, 80%, 85%, 90%, 95% or 98% amino acid sequence identity to a naturally occurring viral structural protein including prM and envelope protein. In one embodiment, the modified protein is a mutant where at most 10% of the amino acids are deleted, substituted, and/or added to a naturally occurring viral structural protein including prM and envelope regions. The sequence identity may be determined by conventional methods.

According to the present application, one or more flavivirus structural proteins or fragments thereof discussed above may be used as long as they spontaneously assemble into a particulate structure. For example, when eukaryotic cells expressing a gene encoding prM and envelope proteins of dengue virus are cultured, the proteins are generated by the cells and assemble to give VLPs, and the VLPs can be collected from the cell culture supernatant.

The present application addresses one or more of the above needs by providing VLPs, vectors encoding the VLPs, and antibodies (and antibody-like molecules including aptamers and peptides) that specifically bind to the antigen, together with the uses thereof (either alone or in combination) in the prevention or treatment of flavivirus infections.

As used in the specification and claims, the term "antibody" refers to a molecule which is capable of binding to an epitope or antigenic determinant. The term covers a whole antibody and an antigen-binding fragment thereof, including a single-chain antibody. Such antibodies may include human antigen binding antibody fragments and include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies can be from any animal origin including birds and mammals. Preferably, the antibodies are mammalian e.g. human, murine, rabbit, goat, guinea pig, camel, horse and the like, or other suitable animals e.g. chicken. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598, the disclosure of which is incorporated herein by reference in its entirety.

A flavivirus structural protein may be a naturally occurring protein or modified protein of the naturally occurring protein or a fragment of the naturally occurring protein or the modified peptide. The modified protein may be a fragment of the naturally occurring virus structural protein.

In one embodiment, the modified protein derived from a flavivirus structural protein has at least 70%, 75%, 80%, 85%, 90%, 95% or 98% amino acid sequence identity to the naturally occurring protein. In one embodiment, the modified protein derived from a flavivirus is a mutant where at most 10% of the amino acids are deleted, substituted, and/or added based on the naturally occurring viral structural protein derived from the flavivirus.

In one embodiment, the present application provides a virus like particle comprising a flavivirus structural protein having an amino acid sequence represented by any one of SEQ ID Nos.2, 4, 8, 10, 14 and 16.

Each of those sequences represents a protein containing the following regions: initiation codon: M (1aa), signal sequence (2-15aa), pr sequence (16-106aa), M sequence (107-181aa), and Envelope region (182-676aa). In one embodiment, a virus like particle comprising a viral structural protein having the regions of prM and envelope region of SEQ ID Nos.2, 4, 8, 10, 14 and 16, i.e. comprising amino acid sequences of from position 16 to position 676 of those proteins may be provided.

The modified flavivirus structural protein may have at least 70%, 75%, 80%, 85%, 90%, 95% or 98% amino acid sequence identity to an amino acid sequence represented by any one of SEQ ID Nos.2, 4, 8, 10, 14 and 16, or an amino acid sequence from position 16 to position 676 of the one of those sequences. Also, the modified flavivirus structural protein may be a mutant where at most 10% of the amino acids are deleted, substituted, and/or added based on the flavivirus structural protein having an amino acid sequence represented by any one of SEQ ID Nos. SEQ ID Nos.2, 4, 8, 10, 14 and 16, or an amino acid sequence from position 16 to position 676 of any one of those sequences.

(2) Nucleotide and Vector

In the second aspect, the present application provides a nucleic acid molecule comprising or consisting of a nucleotide sequence encoding the virus like particle as provided in the first aspect of the present invention.

In one embodiment, the present application provides a nucleic acid molecule comprising a nucleotide sequence that encodes a flavivirus structural protein that provide the virus like particle as described above.

In one embodiment, the present application provides an expression vector comprising the nucleic acid molecule as described above, wherein the vector optionally comprises an expression control sequence operably linked to the nucleic acid molecule.

Examples of expression control sequences include, but are not limited to, promoter such as CMV promoter, phage lambda PL promoter, the *E. coli* lac, phoA and tac promoters, the SV40 early and late promoters, and promoters of retroviral LTRs.

In one embodiment, the present application provides an expression vector for a flavivirus structural protein, which consists of a nucleotide sequence represented by any one of SEQ ID Nos.1, 3, 7, 9, 13 and 15.

In one embodiment, the present application provides a nucleic acid molecule which is modified from the nucleic acid molecule having a nucleotide sequence represented by any one of SEQ ID Nos.1, 3, 7, 9, 13 and 15. The modified nucleic acid molecule may have at least 70%, 75%, 80%, 85%, 90%, 95% or 98% nucleotide sequence identity to the nucleic acid molecule having a nucleotide sequence represented by any one of SEQ ID Nos.1, 3, 7, 9, 13 and 15. Also, the modified nucleic acid molecule may be a mutant where at most 10% of the amino acids are deleted, substituted, and/or added based on the nucleic acid molecule having a nucleotide sequence represented by any one of SEQ ID Nos.1, 3, 7, 9, 13 and 15.

(3) Composition or Vaccine

In the third aspect, the present application provides a composition or vaccine comprising the virus like particle provided in the first aspect of the present application and/or the nucleic acid molecule provided in the second aspect of the present invention.

In one embodiment, the present application provides a composition comprising the flavivirus virus like particle as described above or the nucleic acid molecule as described above.

The composition may further comprise a pharmaceutically acceptable carrier and/or adjuvant. Examples of adjuvant include, but are not limited to Ribi solution (Sigma Adjuvant system, Sigma-Aldrich).

The pharmaceutical composition of the present application may contain a single active ingredient or a combination of two or more active ingredients, as far as they are not contrary to the objects of the present invention. For example, cytokines including chemokines, antibodies against a cytokine such as anti-TNF antibody (e.g. infliximab, adalimumab), anti-VEGF antibody (e.g. bevacizumab and ranibizumab), cytokine receptor antagonist such as anti HER2 antibody (e.g. Trastuzumab), anti EGF receptor antibody (e.g. Cetuximab), anti VEGF aptamer (e.g. Pegaptanib) and immunomodulator such as cyclosporine, tacrolimus and ubenimex may be used for the combination therapy.

In a combination of plural active ingredients, contents of the respective ingredients may be suitably increased or decreased in consideration of their therapeutic effects and safety.

The term "combination" used herein means two or more active ingredients are administered to a patient simultaneously in the form of a single entity or dosage, or those active ingredients are administered to a patient as separate entities either simultaneously or sequentially with no specific time limits, wherein such administration provides therapeutically effective levels of the two components in the body, preferably at the same time.

In one embodiment, the composition is a vaccine composition including a DNA vaccine. In one embodiment, the DNA vaccine provided by the present invention comprises CpG containing oligonucleotide.

(4) Method of Producing an Antibody

In the fourth aspect, the present application provides a method of producing an antibody against a flavivirus or an antiserum containing a neutralizing antibody against a flavivirus, comprising contacting the virus like particle provided in the first aspect of the present application and/or the nucleic acid molecule provided in the second aspect of the present invention to a mammal.

The antibody produced in this aspect may be used for passive immunization against a flavivirus-causing pathogen in a mammal by administering the same to the mammal, and thus prevent the mammal from flavivirus infection or treat a disease or condition caused by flavivirus infection in the mammal.

The antibody produced in the fourth aspect of the present application may be humanized using a conventional technique. Thus, in one embodiment, the method provided in the fourth aspect of the invention further comprises a step of humanizing a non-human mammal produced antibody. The antibody or humanized antibody provided by this aspect may be used for preventing a human subject from flavivirus infection or for treating a disease or condition caused by flavivirus infection in the subject.

The antibody produced according to this aspect may be used in vitro to select a subpopulation from immune cells such as B-cell and T-cell derived from the patient, which are then re-administered to the patient.

Antiserum can be obtained by the conventional manner. Blood samples are taken from the immunized non-human animal, and the blood is processed so as to obtain the antiserum, i.e. the antibody-containing liquid component of the blood. The non-human mammal is preferably selected from the group consisting of rat, mouse, hamster, pig, rabbit, horse, donkey, goat, sheep, guinea pig, lama, and non-human primate (e.g. chimp).

(5) Method of Treating a Disease Caused by a Flavivirus Infection in a Subject or Preventing a Subject from Flavivirus Infection In the fifth aspect, a method of treating a disease or condition caused by flavivirus infection such as dengue fever in a subject, wherein the virus like particle provided in the first aspect, the nucleotide molecule provided in the second aspect, or the composition provided in the third aspect is administered to the subject. By administering the above listed VLP, nucleotide molecule or composition to the subject, immune response against a flavivirus can be enhanced and thus, the disease or condition caused by the flavivirus infection can effectively be treated. In this aspect, the VLP, nucleotide molecule or composition may be administered to the patient locally to the affected organ or systemically.

A method of preventing a subject from a flavivirus infection or from a disease caused by a flavivirus infection, comprising administering the virus like particle of the first aspect, the nucleotide molecule provided in the second aspect or the composition of the third aspect to the subject. The disease caused by a flavivirus may be dengue fever.

According to the present application, the virus like particle can also be applied for immune therapy. The VLP may be applied ex vivo to cells derived from the patient or a human cell line which are subsequently administered to the patient.

(6) Method of Producing the Virus Like Particle

In the sixth aspect, the present application provides a method of producing the virus like particle provided in the first aspect of the present invention, comprising culturing a cell which is expressing a gene coding for the viral structural protein; and recovering the virus like particle from the cell culture.

Various host-vector systems may be used for expression of the virus like particle. Eukaryotic cells can be used for the method provided by the fourth aspect of the present application. Examples of eukaryotic cells include, but are not limited to, insect cells (e.g. sf9 cells, H5 cells), yeast cells (e.g. *S. cerevisiae*) and mammalian cells (e.g. CHO cells, human embryonic kidney (HEK) 293F cells). Vector used for the method provided by the second aspect of the present application comprises a nucleic acid molecule encoding the virus like particle to be expressed. Cells may be transfected with the vector using conventional methods (e.g. lipofection, electroporation). A skilled person can select culture medium or with DNA methyl transferase inhibitors and histone deacetylase inhibitors such as sodium butyrate, depending on cells employed. After the transfection, virus like particle can be produced in the cells and/or culture supernatant. Virus like particle may be recovered from the culture supernatant and purified using ultracentrifugation.

The virus like particles of the present application do not replicate and therefore, have highly safe profiles.

(7) Kit or Method of Diagnosing Flavivirus Infection

In the seventh aspect, the present application provides a virus like particle for use in a method or kit of diagnosing flavivirus infection in a mammal. By using the virus like particles, an enzyme-linked immune-sorbent assay (ELISA) diagnostic kit capable of detecting an antibody specific to the flavivirus could be produced.

The present application will be described in detail with reference to the following example, which, however, is not intended to limit the scope of the present invention.

EXAMPLE 1

Preparation of a Virus Like Particle Comprising a Protein or a Fragment of Dengue Virus Type 1-2

Dengue virus types 1 and 2 viral structural proteins were used as the wild type viral structural proteins. In the envelope region of the viral structural proteins, at least one alternation was introduced. Namely, amino acid Phe at position 108 of Dengue virus type 1 envelope protein (SEQ ID NO: 20) was altered to Ala (F108A), amino acid Lys at position 203 of Dengue virus type 1 envelope protein was altered to Asn (K203N) (Envelope region: 172-676aa of SEQ ID NO: 4), amino acid Asn at position 246 was altered to Met (K246M). In this example, envelope region corresponds to 172-676aa of SEQ ID NO: 2, position 108 of SEQ ID NO: 20 corresponds to position 289 of SEQ ID NO: 2, position 203 of SEQ ID NO: 20 corresponds position 384 of SEQ ID NO: 2, and position 246 of SEQ ID NO: 20 corresponds to position 427 of SEQ ID NO: 2. In the examples, mutation in the envelope region is expressed using the number starting from the envelope region.

To express the viral structural protein in mammalian cells, DENV2 prM E expression vector and DENV2 Capsid expression vector 20 ug each were mixed and transfected to 293F cells. Capsid vector was mutated R85A and K86A to express better yield (SEQ ID NO: 11 and 12). To express the DENV2 prM E better, C terminal DENV2 Env region (199aa-676aa) was replaced to the corresponding DENV1 Env region to give chimera proteins (SEQ ID NOs. 7 and 8). To stabilize the VLPs, Env fusion peptide region (F108A) was mutated (SEQ ID NOs. 9 and 10).

4 days after the transfection, supernatant from the transfected cell culture was harvested and the Env expression was examined by Western blotting using Dengue virus (9.F.10) monoclonal antibody that specifically binds to the envelope protein (sc-70959, Santa Cruz Biotechnology) as a 1st antibody and rabbit anti-mouse IgG-HRP (sc-358920, Santa Cruz Biotechnology) as a 2nd antibody. The result is shown in FIG. 2.

As shown from FIG. 2, cells transfected with DENV2 prM and the chimera of Dengue virus type 2 and type 1 envelope protein with one alteration (F108A) generated higher amount of protein. Those proteins in the supernatant spontaneously assembled to give particles.

To express the VLP, DENV1 prM E expression vector and DENV1 Capsid expression vector 20 ug each were mixed and transfected to 293F cells. Capsid vector was mutated K85A and K86A to express better yield (SEQ ID NOs. 5 and 6). To stabilize the VLPs, Env fusion peptide region (F108A) (SEQ ID NOs. 1 and 2) or basic amino acid (K203N) (SEQ ID NOs. 3 and 4) or (K246M) were mutated. Further, two amino acids (F108A+K246M, SEQ ID NOs: 13 and 14) and (F108A+K203N, SEQ ID NOs. 15 and 16) were also mutated. 4 days after transfection, supernatant from the transfected cells was harvested and the Env expression was examined by Western blotting using Dengue virus (9.F.10) monoclonal antibody (sc-70959, Santa Cruz Biotechnology) as a 1st antibody and rabbit anti-mouse IgG-HRP (sc-358920, Santa Cruz Biotechnology) as a 2nd antibody. Results are shown in FIG. 3.

As shown by FIG. 3, cells transfected with DENV prM and the envelope protein with at least one alteration generated higher amount of envelope protein. Those proteins in the supernatant spontaneously assembled to give particles.

EXAMPLE 2

Figure 4:
FIG. 4 shows results of Western Blotting. An expression vector for viral structural protein comprising Dengue type 1 virus prM and envelope with or without alteration (wild type, F108A, K203M or F108+K203N) was transfected to 293F cells. Western blotting using antibody against Dengue Envelope protein was conducted against the culture supernatant.

Preparation of a Virus Like Particle Comprising Dengue Virus Structural Protein prM and Envelope Expression vector for Dengue virus structural proteins containing prM and modified Envelope protein F108A, K203N, or K203N+F108A (SEQ ID NOs 1, 3, 15 respectively) used in Example 1 were used. In the same manner as Example 1, 20 ug of the vector was transfected to 293F cells and cultured. Supernatants from the transfected cells were harvested on day 4 after the transfection. Western Blot was performed to detect DENV VLP using a monoclonal antibody (9.F.10, Santa Cruz Biotech) as a primary antibody and rabbit anti-mouse IgG-HRP conjugated antibodies as a secondary antibody. Results are shown in FIG. 4. As shown by FIG. 4, cells transfected with DENV1-prM and the envelope protein with at least one alteration generated higher amount of envelope protein.

Figure 5:
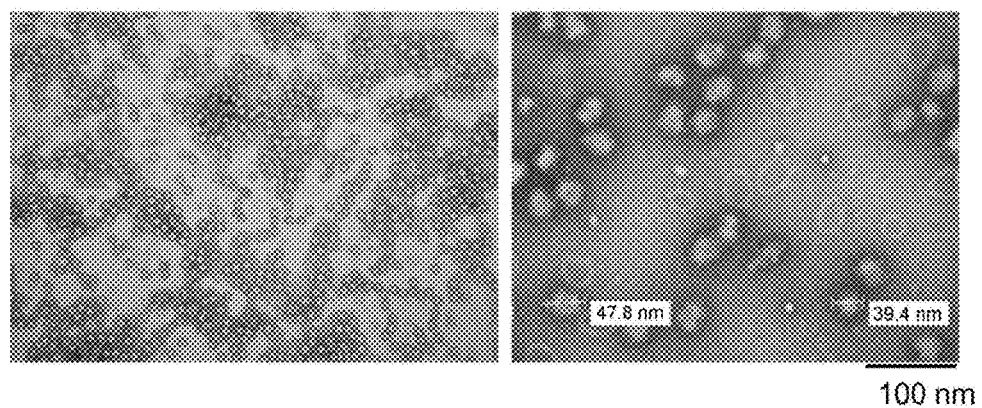
FIG. 5 shows the Electron microscopic (EM) visualization of negatively stained VLPs (F108+K203N).

The supernatant was filtrated using 0.45 µm filter to obtain virus like particles. The virus like particles were concentrated using TFF column and purified using QXL column (GE Healthcare) to obtain purified virus like particles. The purified VLP was filed in 4% formaldehyde in PBS. Electron microscopic (EM) visualization of negatively stained VLPs was performed. Briefly, 1.0 µl of the sample was placed onto a carbon coated Formvar-filmed copper grid and allowed the VLPs to attach. Then, 2 µl 1% PTA solution was added to the grid and the grid was examined by electron microscope. The result is shown in FIG. 5. In the supernatant, virus like particles were observed.

EXAMPLE 3

Antibody Against Dengue Virus

Purified VLP obtained in Example 2 (K203N+F108A) was named as DEN1 VLP and used in this example. The purified virus like particles were further concentrated using spin column (Molecular Weight-cutoff: 100 kDa) to prepare the virus like particles for the immunization. Then, four (4) mice were immunized with DEN1 VLP 30 µg in PBS containing aluminum adjuvant (alhydrogel 2%, Sergeant Aduvants) by intramuscle injection two times at weeks 0 and 4.

Dengue virus specific IgG titers of the serum derived from the immunized mice were determined by ELISA system. The serum was assayed for neutralizing antibody to each of DENV-1, DENV-2, DENV-3, and DENV-4 virus. The following Dengue serotypes 1-4 were used:

DENV-1, Philippine-99St12A strain

DENV-2, Philippine-00St22A strain

DENV-3, Philipine-SLMC50 strain

DENV-4, Philippine-SLMC318 strain

JEV-JaOAr S-982 strain

Anti-DENV neutralizing antibodies in the immunized mice sera were detected by a previously described focus reduction neutralization test (FRNT) on Vero cells using $1.25 \times 10^8$ FFU of Vero-adapted DVs type 1-4. The endpoint titer was calculated as the highest serum dilution tested that reduced the number of FFU by at least 50% ($FRNT_{50}$). Vero cells at 100% confluence in 96 wells plates were used.

In house anti-Dengue rabbit IgG was used as the primary antibody, and anti-rabbit IgG-HRPO conjugate (102-PD) was used as the secondary antibody. The results are summarized in table below.

TABLE 1

| serotype | D-1 | D-2 | D-3 | D-4 | JE |
|---|---|---|---|---|---|
| DENV1 VLP | >10240 | 1043 | 604 | 270 | <80 |
| PBS | <80 | <80 | <80 | <80 | <80 |

As shown in table 1, the DENV1 VLP exhibited superior neutralizing effect on Dengue virus types 1, 2, 3 and 4. In view of the fact that the FRNT 50 value of neutralizing antibodies obtained with Dengue attenuated live vaccine is around 1000 (Tsai et al., Journal of Virology, 2015 89: 7348-7362.), the immunogenicity of DENV1 VLP is very strong and can provide about 10 times higher neutralizing antibody against Dengue virus than attenuated live vaccine.

EXAMPLE 4

Preparation of a Pharmaceutical Composition Comprising Dengue Virus Like Particle Dengue virus like particles were prepared according to Example 1. To prepare a pharmaceutical composition which is a vaccine composition, 80 μg of each of the prepared particles was mixed with 1 ml of Sucrose Phosphate Solution, pH 7.2, Endotoxin Free (Teknova, SP buffer).

EXAMPLE 5

Preparation of a Dengue Virus Type 2-4 Derived Virus Like Particles

Expression vectors for prM and Envelope proteins of Dengue virus type 2-4, wherein amino acid position 108 of the envelope region (corresponding to 289aa of SEQ ID NOs. 22-24) is replaced from F to A and C-terminal region of the Envelope protein (478-676aa or 476-674aa) is replaced with that corresponding to Dengue virus type 1 Envelope protein (478-676aa of SEQ ID NO. 22) are prepared. Proteins to be expressed by the vectors are those represented by SEQ ID NOs. 22-24. Virus like particles are obtained in the same manner as Example 1.

What is claimed is:

1. A virus like particle comprising a flavivirus envelope protein, wherein said envelope protein comprises an amino acid substitution at position 108 of SEQ ID NO: 20, or at a position determined as corresponding to position 108 of SEQ ID NO: 20 by alignment.

2. The virus like particle according to claim 1, wherein the flavivirus is West Nile virus, dengue virus, tick-borne encephalitis virus, yellow fever virus, or Japanese encephalitis virus.

3. The virus like particle according to claim 2, wherein said flavivirus is dengue virus.

4. The virus like particle according to claim 1, wherein said virus like particle is produced from a dengue virus structural protein comprising prM and envelope regions.

5. The virus like particle according to claim 4, wherein said structural protein comprises the amino acid sequence of residues 16-676 of an amino acid sequence selected from the group consisting of SEQ ID NOs: 2, 4, 8, 10, 14 and 16.

6. The virus like particle according to claim 4, wherein said structural protein is a protein consisting of an amino acid sequence selected from the group consisting of SEQ ID NOs: 2, 4, 8, 10, 14 and 16.

7. A composition comprising the virus like particle according to claim 1 and a pharmaceutically acceptable carrier.

8. The composition according to claim 7 for treating or preventing a disease or condition caused by flavivirus infection.

9. A method of producing a virus like particle, comprising culturing a cell which is transfected with a polynucleotide encoding the envelope protein contained in the virus like particle according to claim 1; and recovering the virus like particle from the cell culture.

10. A method of producing an antibody, comprising contacting the virus like particle according to claim 1 to a mammal.

11. The virus like particle according to claim 1, wherein said virus like particle further comprises a prM protein.

12. The virus like particle according to claim 1, wherein said envelope protein further comprises an amino acid substitution at position 203 of SEQ ID NO: 20, or at a position determined as corresponding to position 203 of SEQ ID NO: 20 by alignment.

13. The virus like particle according to claim 1, wherein said envelope protein further comprises an amino acid substitution at position 246 of SEQ ID NO: 20, or at a position determined as corresponding to position 246 of SEQ ID NO: 20 by alignment.

14. The virus like particle according to claim 1, wherein the substitution at position 108, or at the position corresponding to position 108, is the substitution of phenylalanine with alanine.

15. The virus like particle according to claim 12, wherein the substitution at position 203, or at the position corresponding to position 203, is the substitution of lysine with asparagine.

16. The virus like particle according to claim 13, wherein the substitution at position 246, or at the position corresponding to position 246, is the substitution of lysine with methionine.

* * * * *

SEQUENCE LISTING

```
<160> NUMBER OF SEQ ID NOS: 24

<210> SEQ ID NO 1
<211> LENGTH: 5498
<212> TYPE: DNA
<213> ORGANISM: Dengue virus
<220> FEATURE:
<221> NAME/KEY: misc_feature
<223> OTHER INFORMATION: DENV1 prM E (Env F108A)
<220> FEATURE:
<221> NAME/KEY: CDS
<222> LOCATION: (1046)..(3073)

<400> SEQUENCE: 1
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt gacgcgtttg acattgatta     420
ttgactagtt attaatagta atcaattacg gggtcattag ttcatagccc atatatggag     480
ttccgcgtta cataacttac ggtaaatggc ccgcctggct gaccgcccaa cgaccccgc      540 ccattgacgt caataatgac gtatgttccc atagtaacgc caatagggac tttccattga     600
cgtcaatggg tggagtattt acggtaaact gcccacttgg cagtacatca agtgtatcat     660
atgccaagta cgccccctat tgacgtcaat gacggtaaat ggcccgcctg gcattatgcc     720
cagtacatga ccttatggga ctttcctact tggcagtaca tctacgtatt agtcatcgct     780
attaccatgg tgatgcggtt ttggcagtac atcaatgggc gtggatagcg gtttgactca     840
cggggatttc caagtctcca ccccattgac gtcaatggga gtttgttttg gcaccaaaat     900
caacgggact ttccaaaatg tcgtaacaac tccgccccat tgacgcaaat gggcggtagg     960
cgtgtacggt gggaggtcta taagcaga gctcgtttag tgaaccgtca gataactgca     1020
ggtcgacgat atcgcggccg ccacc atg tcg gtg acc atg ctc ctc atg ctg     1072
                              Met Ser Val Thr Met Leu Leu Met Leu
                                1               5 ctg ccc aca gcc ctg gcg ttc cat ctg acc acc cga ggg gga gag ccg     1120
Leu Pro Thr Ala Leu Ala Phe His Leu Thr Thr Arg Gly Gly Glu Pro
 10              15                  20                  25
```

-continued

| | | | | | | | | | | | | | | | | |
|---|---|---|---|---|---|---|---|---|---|---|---|---|---|---|---|---|
| cac | atg | ata | gtt | agc | aag | cag | gaa | aga | gga | aaa | tca | ctt | ttg | ttt | aag | 1168 |
| His | Met | Ile | Val | Ser | Lys | Gln | Glu | Arg | Gly | Lys | Ser | Leu | Leu | Phe | Lys | |
| | | | 30 | | | | 35 | | | | | 40 | | | | |

| acc | tct | gca | ggt | gtc | aac | atg | tgc | acc | ctt | att | gca | atg | gat | ttg | gga | 1216 |
|---|---|---|---|---|---|---|---|---|---|---|---|---|---|---|---|---|
| Thr | Ser | Ala | Gly | Val | Asn | Met | Cys | Thr | Leu | Ile | Ala | Met | Asp | Leu | Gly | |
| | | | 45 | | | | 50 | | | | 55 | | | | | |

| gag | tta | tgt | gag | gac | aca | atg | acc | tac | aaa | tgc | ccc | cgg | atc | act | gag | 1264 |
|---|---|---|---|---|---|---|---|---|---|---|---|---|---|---|---|---|
| Glu | Leu | Cys | Glu | Asp | Thr | Met | Thr | Tyr | Lys | Cys | Pro | Arg | Ile | Thr | Glu | |
| | | 60 | | | | | 65 | | | | | 70 | | | | |

| acg | gaa | cca | gat | gac | gtt | gac | tgt | tgg | tgc | aat | gcc | acg | gag | aca | tgg | 1312 |
|---|---|---|---|---|---|---|---|---|---|---|---|---|---|---|---|---|
| Thr | Glu | Pro | Asp | Asp | Val | Asp | Cys | Trp | Cys | Asn | Ala | Thr | Glu | Thr | Trp | |
| | 75 | | | | | 80 | | | | | 85 | | | | | |

| gtg | acc | tat | gga | aca | tgt | tct | caa | act | ggt | gaa | cac | cga | cga | gac | aaa | 1360 |
|---|---|---|---|---|---|---|---|---|---|---|---|---|---|---|---|---|
| Val | Thr | Tyr | Gly | Thr | Cys | Ser | Gln | Thr | Gly | Glu | His | Arg | Arg | Asp | Lys | |
| 90 | | | | | 95 | | | | | 100 | | | | | 105 | |

| cgt | tcc | gtc | gca | ctg | gca | cca | cac | gta | ggg | ctt | ggt | cta | gaa | aca | aga | 1408 |
|---|---|---|---|---|---|---|---|---|---|---|---|---|---|---|---|---|
| Arg | Ser | Val | Ala | Leu | Ala | Pro | His | Val | Gly | Leu | Gly | Leu | Glu | Thr | Arg | |
| | | | | 110 | | | | | 115 | | | | | 120 | | |

| acc | gaa | acg | tgg | atg | tcc | tct | gaa | ggc | gct | tgg | aaa | caa | ata | caa | aaa | 1456 |
|---|---|---|---|---|---|---|---|---|---|---|---|---|---|---|---|---|
| Thr | Glu | Thr | Trp | Met | Ser | Ser | Glu | Gly | Ala | Trp | Lys | Gln | Ile | Gln | Lys | |
| | | | 125 | | | | | 130 | | | | | 135 | | | |

| gtg | gag | acc | tgg | gct | ctg | aga | cac | cca | gga | ttc | acg | gtg | ata | gcc | ctt | 1504 |
|---|---|---|---|---|---|---|---|---|---|---|---|---|---|---|---|---|
| Val | Glu | Thr | Trp | Ala | Leu | Arg | His | Pro | Gly | Phe | Thr | Val | Ile | Ala | Leu | |
| | | 140 | | | | | 145 | | | | | 150 | | | | |

| ttt | cta | gca | cat | gcc | ata | gga | aca | tcc | atc | acc | cag | aaa | ggg | atc | att | 1552 |
|---|---|---|---|---|---|---|---|---|---|---|---|---|---|---|---|---|
| Phe | Leu | Ala | His | Ala | Ile | Gly | Thr | Ser | Ile | Thr | Gln | Lys | Gly | Ile | Ile | |
| | 155 | | | | | 160 | | | | | 165 | | | | | |

| ttt | att | ttg | ctg | atg | ctg | gta | act | cca | tcc | atg | gcc | atg | cgg | tgc | gtg | 1600 |
|---|---|---|---|---|---|---|---|---|---|---|---|---|---|---|---|---|
| Phe | Ile | Leu | Leu | Met | Leu | Val | Thr | Pro | Ser | Met | Ala | Met | Arg | Cys | Val | |
| 170 | | | | | 175 | | | | | 180 | | | | | 185 | |

| gga | ata | ggc | aac | aga | gac | ttc | gtg | gaa | gga | ctg | tca | gga | gct | acg | tgg | 1648 |
|---|---|---|---|---|---|---|---|---|---|---|---|---|---|---|---|---|
| Gly | Ile | Gly | Asn | Arg | Asp | Phe | Val | Glu | Gly | Leu | Ser | Gly | Ala | Thr | Trp | |
| | | | | 190 | | | | | 195 | | | | | 200 | | |

| gtg | gat | gtg | gta | ctg | gag | cat | gga | agt | tgc | gtc | act | acc | atg | gca | aaa | 1696 |
|---|---|---|---|---|---|---|---|---|---|---|---|---|---|---|---|---|
| Val | Asp | Val | Val | Leu | Glu | His | Gly | Ser | Cys | Val | Thr | Thr | Met | Ala | Lys | |
| | | | 205 | | | | | 210 | | | | | 215 | | | |

| gac | aaa | cca | aca | ctg | gac | att | gaa | ctc | ttg | aag | acg | gag | gtc | aca | aac | 1744 |
|---|---|---|---|---|---|---|---|---|---|---|---|---|---|---|---|---|
| Asp | Lys | Pro | Thr | Leu | Asp | Ile | Glu | Leu | Leu | Lys | Thr | Glu | Val | Thr | Asn | |
| | | 220 | | | | | 225 | | | | | 230 | | | | |

| cct | gcc | gtc | ctg | cgc | aaa | ctg | tgc | att | gaa | gct | aaa | ata | tca | aac | acc | 1792 |
|---|---|---|---|---|---|---|---|---|---|---|---|---|---|---|---|---|
| Pro | Ala | Val | Leu | Arg | Lys | Leu | Cys | Ile | Glu | Ala | Lys | Ile | Ser | Asn | Thr | |
| | 235 | | | | | 240 | | | | | 245 | | | | | |

| acc | acc | gat | tcg | aga | tgt | cca | aca | caa | gga | gaa | gcc | acg | ctg | gtg | gaa | 1840 |
|---|---|---|---|---|---|---|---|---|---|---|---|---|---|---|---|---|
| Thr | Thr | Asp | Ser | Arg | Cys | Pro | Thr | Gln | Gly | Glu | Ala | Thr | Leu | Val | Glu | |
| 250 | | | | | 255 | | | | | 260 | | | | | 265 | |

| gaa | cag | gac | acg | aac | ttt | gtg | tgt | cga | cga | acg | ttc | gtg | gac | aga | ggc | 1888 |
|---|---|---|---|---|---|---|---|---|---|---|---|---|---|---|---|---|
| Glu | Gln | Asp | Thr | Asn | Phe | Val | Cys | Arg | Arg | Thr | Phe | Val | Asp | Arg | Gly | |
| | | | | 270 | | | | | 275 | | | | | 280 | | |

| tgg | ggc | aat | ggt | tgt | ggg | cta | gcc | gga | aaa | ggt | agc | tta | ata | acg | tgt | 1936 |
|---|---|---|---|---|---|---|---|---|---|---|---|---|---|---|---|---|
| Trp | Gly | Asn | Gly | Cys | Gly | Leu | Ala | Gly | Lys | Gly | Ser | Leu | Ile | Thr | Cys | |
| | | | 285 | | | | | 290 | | | | | 295 | | | |

| gct | aag | ttt | aag | tgt | gtg | aca | aaa | ctg | gaa | gga | aag | ata | gtc | caa | tat | 1984 |
|---|---|---|---|---|---|---|---|---|---|---|---|---|---|---|---|---|
| Ala | Lys | Phe | Lys | Cys | Val | Thr | Lys | Leu | Glu | Gly | Lys | Ile | Val | Gln | Tyr | |
| | | 300 | | | | | 305 | | | | | 310 | | | | |

| gaa | aac | tta | aaa | tat | tca | gtg | ata | gtc | acc | gta | cac | act | gga | gac | cag | 2032 |
|---|---|---|---|---|---|---|---|---|---|---|---|---|---|---|---|---|
| Glu | Asn | Leu | Lys | Tyr | Ser | Val | Ile | Val | Thr | Val | His | Thr | Gly | Asp | Gln | |
| | 315 | | | | | 320 | | | | | 325 | | | | | |

| cac | caa | gtt | gga | aat | gag | acc | aca | gaa | cat | gga | aca | act | gca | acc | ata | 2080 |
|---|---|---|---|---|---|---|---|---|---|---|---|---|---|---|---|---|
| His | Gln | Val | Gly | Asn | Glu | Thr | Thr | Glu | His | Gly | Thr | Thr | Ala | Thr | Ile | |

-continued

```
            330                 335                 340                 345
aca cct caa gct ccc acg tcg gaa ata cag ctg aca gac tac gga gct         2128
Thr Pro Gln Ala Pro Thr Ser Glu Ile Gln Leu Thr Asp Tyr Gly Ala
                    350                 355                 360 cta aca ttg gat tgt tca cct aga aca ggg cta gac ttt aat gag atg         2176
Leu Thr Leu Asp Cys Ser Pro Arg Thr Gly Leu Asp Phe Asn Glu Met
            365                 370                 375 gtg ttg ttg aca atg gaa aaa aaa tca tgg ctc gtc cac aaa caa tgg         2224
Val Leu Leu Thr Met Glu Lys Lys Ser Trp Leu Val His Lys Gln Trp
        380                 385                 390 ttt cta gac tta cca ctg cct tgg acc tcg ggg gct tca aca tcc caa         2272
Phe Leu Asp Leu Pro Leu Pro Trp Thr Ser Gly Ala Ser Thr Ser Gln
    395                 400                 405 gag act tgg aat aga caa gac ttg ctg gtc aca ttt aag aca gct cat         2320
Glu Thr Trp Asn Arg Gln Asp Leu Leu Val Thr Phe Lys Thr Ala His
410                 415                 420                 425 gca aaa aag cag gaa gta gtc gta cta gga tca caa gaa gga gca atg         2368
Ala Lys Lys Gln Glu Val Val Val Leu Gly Ser Gln Glu Gly Ala Met
                430                 435                 440 cac act gcg ttg act gga gcg aca gaa atc caa acg tct gga acg aca         2416
His Thr Ala Leu Thr Gly Ala Thr Glu Ile Gln Thr Ser Gly Thr Thr
            445                 450                 455 aca att ttt gca gga cac ctg aaa tgc aga cta aaa atg gat aaa ctg         2464
Thr Ile Phe Ala Gly His Leu Lys Cys Arg Leu Lys Met Asp Lys Leu
        460                 465                 470 act tta aaa ggg atg tca tat gta atg tgc aca ggg tca ttc aag tta         2512
Thr Leu Lys Gly Met Ser Tyr Val Met Cys Thr Gly Ser Phe Lys Leu
    475                 480                 485 gag aag gaa gtg gct gag acc cag cat gga act gtt cta gtg cag gtt         2560
Glu Lys Glu Val Ala Glu Thr Gln His Gly Thr Val Leu Val Gln Val
490                 495                 500                 505 aaa tac gaa gga aca gat gca cca tgc aag atc ccc ttc tcg tcc caa         2608
Lys Tyr Glu Gly Thr Asp Ala Pro Cys Lys Ile Pro Phe Ser Ser Gln
                510                 515                 520 gat gag aag gga gta acc cag aat ggg aga ttg ata aca gcc aac ccc         2656
Asp Glu Lys Gly Val Thr Gln Asn Gly Arg Leu Ile Thr Ala Asn Pro
            525                 530                 535 ata gtc act gac aaa gaa aaa cca gtc aac att gaa gcg gag cca cct         2704
Ile Val Thr Asp Lys Glu Lys Pro Val Asn Ile Glu Ala Glu Pro Pro
        540                 545                 550 ttt ggt gag agc tac att gtg gta gga gca ggt gaa aaa gct ttg aaa         2752
Phe Gly Glu Ser Tyr Ile Val Val Gly Ala Gly Glu Lys Ala Leu Lys
    555                 560                 565 cta agc tgg ttc aag aag gga agc agt ata ggg aaa atg ttt gaa gca         2800
Leu Ser Trp Phe Lys Lys Gly Ser Ser Ile Gly Lys Met Phe Glu Ala
570                 575                 580                 585 act gcc cgt gga gca cga agg atg gcc atc ctg gga gac act gca tgg         2848
Thr Ala Arg Gly Ala Arg Arg Met Ala Ile Leu Gly Asp Thr Ala Trp
                590                 595                 600 gac ttc ggt tct ata gga ggg gtg ttc acg tct gtg gga aaa ctg ata         2896
Asp Phe Gly Ser Ile Gly Gly Val Phe Thr Ser Val Gly Lys Leu Ile
            605                 610                 615 cac cag att ttt ggg act gcg tat gga gtt ttg ttc agc ggt gtt tct         2944
His Gln Ile Phe Gly Thr Ala Tyr Gly Val Leu Phe Ser Gly Val Ser
        620                 625                 630 tgg acc atg aag ata gga ata ggg att ctg ctg aca tgg cta gga tta         2992
Trp Thr Met Lys Ile Gly Ile Gly Ile Leu Leu Thr Trp Leu Gly Leu
    635                 640                 645 aac tca agg agc acg tcc ctt tca atg acg tgt atc gca gtt ggc atg         3040
Asn Ser Arg Ser Thr Ser Leu Ser Met Thr Cys Ile Ala Val Gly Met
```

```
Asn Ser Arg Ser Thr Ser Leu Ser Met Thr Cys Ile Ala Val Gly Met
650                 655                 660                 665 gtc acg ctg tac cta gga gtc atg gtt cag gcg taataaagat ctgctgtgcc    3093
Val Thr Leu Tyr Leu Gly Val Met Val Gln Ala
                670                 675 ttctagttgc cagccatctg ttgtttgccc ctcccccgtg ccttccttga ccctggaagg    3153
tgccactccc actgtccttt cctaataaaa tgaggaaatt gcatcgcatt gtctgagtag    3213
gtgtcattct attctggggg gtggggtggg gcaggacagc aaggggggagg attgggaaga   3273 caatagcagg catgctgggg atgcggtggg ctctatggct cgagcatggt catagctgtt    3333
tcctgtgtga aattgttatc cgctcacaat tccacacaac atacgagccg aagcataaa     3393 gtgtaaagcc tggggtgcct aatgagtgag ctaactcaca ttaattgcgt tgcgctcact    3453
gcccgctttc cagtcgggaa acctgtcgtg ccagctgcat taatgaatcg ccaacgcgc     3513 ggggagaggc ggtttgcgta ttgggcgctc ttccgcttcc tcgctcactg actcgctgcg    3573
ctcggtcgtt cggctgcggc gagcggtatc agctcactca aaggcggtaa tacggttatc    3633
cacagaatca ggggataacg caggaaagaa catgtgagca aaaggccagc aaaaggccag    3693
gaaccgtaaa aaggccgcgt tgctggcgtt tttccatagg ctccgccccc ctgacgagca    3753
tcacaaaaat cgacgctcaa gtcagaggtg gcgaaacccg acaggactat aaagatacca    3813
ggcgtttccc cctggaagct ccctcgtgcg ctctcctgtt ccgaccctgc cgcttaccgg    3873
atacctgtcc gcctttctcc cttcgggaag cgtggcgctt tctcatagct cacgctgtag    3933
gtatctcagt tcggtgtagg tcgttcgctc caagctgggc tgtgtgcacg aaccccccgt    3993
tcagcccgac cgctgcgcct tatccggtaa ctatcgtctt gagtccaacc cggtaagaca    4053
cgacttatcg ccactggcag cagccactgg taacaggatt agcagagcga ggtatgtagg    4113
cggtgctaca gagttcttga agtggtggcc taactacggc tacactagaa gaacagtatt    4173
tggtatctgc gctctgctga agccagttac cttcggaaaa agagttggta gctcttgatc    4233
cggcaaacaa accaccgctg gtagcggtgg ttttttttgtt tgcaagcagc agattacgcg    4293
cagaaaaaaa ggatctcaag aagatccttt gatcttttct acggggtctg acgctcagtg    4353
gaacgaaaac tcacgttaag ggattttggt catgagatta tcaaaaagga tcttcaccta    4413 gatccttta aattaaaaat gaagttttaa atcaatctaa agtatatatg agtaaacttg     4473
gtctgacagt tagaaaaact catcgagcat caaatgaaac tgcaatttat tcatatcagg    4533
attatcaata ccatattttt gaaaagccg tttctgtaat gaaggagaaa actcaccgag     4593
gcagttccat aggatggcaa gatcctggta tcggtctgcg attccgactc gtccaacatc    4653 aatacaaccct attaatttcc cctcgtcaaa aataaggtta tcaagtgaga atcaccatg    4713 agtgacgact gaatccggtg agaatggcaa aagtttatgc atttctttcc agacttgttc    4773
aacaggccag ccattacgct cgtcatcaaa atcactcgca tcaaccaaac cgttattcat    4833
tcgtgattgc gcctgagcga cgcgaatac gcgatcgctg ttaaaaggac aattacaaac     4893
aggaatcgaa tgcaaccggc gcaggaacac tgccagcgca tcaacaatat tttcacctga    4953
atcaggatat tcttctaata cctggaatgc tgttttccca gggatcgcag tggtgagtaa    5013
ccatgcatca tcaggagtac ggataaaatg cttgatggtc ggaagaggca taaattccgt    5073
cagccagttt agtctgacca tctcatctgt aacatcattg gcaacgctac ctttgccatg    5133
tttcagaaac aactctggcg catcgggctt cccatacaat cgatagattg tcgcacctga    5193
ttgcccgaca ttatcgcgag cccatttata cccatataaa tcagcatcca tgttggaatt    5253
```

-continued

```
taatcgcggc ctagagcaag acgtttcccg ttgaatatgg ctcatactct tccttttca      5313 atattattga agcatttatc agggttattg tctcatgagc ggatacatat ttgaatgtat      5373
ttagaaaaat aaacaaatag gggttccgcg cacatttccc cgaaaagtgc cacctgacgt      5433
ctaagaaacc attattatca tgacattaac ctataaaaat aggcgtatca cgaggccctt      5493
tcgtc                                                                  5498
```

<210> SEQ ID NO 2
<211> LENGTH: 676
<212> TYPE: PRT
<213> ORGANISM: Dengue virus

<400> SEQUENCE: 2

```
Met Ser Val Thr Met Leu Leu Met Leu Leu Pro Thr Ala Leu Ala Phe
1               5                   10                  15

His Leu Thr Thr Arg Gly Gly Glu Pro His Met Ile Val Ser Lys Gln
            20                  25                  30

Glu Arg Gly Lys Ser Leu Leu Phe Lys Thr Ser Ala Gly Val Asn Met
        35                  40                  45

Cys Thr Leu Ile Ala Met Asp Leu Gly Glu Leu Cys Glu Asp Thr Met
    50                  55                  60

Thr Tyr Lys Cys Pro Arg Ile Thr Glu Thr Glu Pro Asp Asp Val Asp
65                  70                  75                  80

Cys Trp Cys Asn Ala Thr Glu Thr Trp Val Thr Tyr Gly Thr Cys Ser
                85                  90                  95

Gln Thr Gly Glu His Arg Arg Asp Lys Arg Ser Val Ala Leu Ala Pro
            100                 105                 110

His Val Gly Leu Gly Leu Glu Thr Arg Thr Glu Thr Trp Met Ser Ser
        115                 120                 125

Glu Gly Ala Trp Lys Gln Ile Gln Lys Val Glu Thr Trp Ala Leu Arg
130                 135                 140

His Pro Gly Phe Thr Val Ile Ala Leu Phe Leu Ala His Ala Ile Gly
145                 150                 155                 160

Thr Ser Ile Thr Gln Lys Gly Ile Ile Phe Ile Leu Leu Met Leu Val
                165                 170                 175

Thr Pro Ser Met Ala Met Arg Cys Val Gly Ile Gly Asn Arg Asp Phe
            180                 185                 190

Val Glu Gly Leu Ser Gly Ala Thr Trp Val Asp Val Leu Glu His
        195                 200                 205

Gly Ser Cys Val Thr Thr Met Ala Lys Asp Lys Pro Thr Leu Asp Ile
210                 215                 220

Glu Leu Leu Lys Thr Glu Val Thr Asn Pro Ala Val Leu Arg Lys Leu
225                 230                 235                 240

Cys Ile Glu Ala Lys Ile Ser Asn Thr Thr Thr Asp Ser Arg Cys Pro
                245                 250                 255

Thr Gln Gly Glu Ala Thr Leu Val Glu Glu Gln Asp Thr Asn Phe Val
            260                 265                 270

Cys Arg Arg Thr Phe Val Asp Arg Gly Trp Gly Asn Gly Cys Gly Leu
        275                 280                 285

Ala Gly Lys Gly Ser Leu Ile Thr Cys Ala Lys Phe Lys Cys Val Thr
    290                 295                 300

Lys Leu Glu Gly Lys Ile Val Gln Tyr Glu Asn Leu Lys Tyr Ser Val
305                 310                 315                 320

Ile Val Thr Val His Thr Gly Asp Gln His Gln Val Gly Asn Glu Thr
```

|     |     |     |     |     | 325 |     |     |     |     | 330 |     |     |     |     | 335 |
| --- | --- | --- | --- | --- | --- | --- | --- | --- | --- | --- | --- | --- | --- | --- | --- |

Thr Glu His Gly Thr Thr Ala Thr Ile Thr Pro Gln Ala Pro Thr Ser
                340                 345                 350

Glu Ile Gln Leu Thr Asp Tyr Gly Ala Leu Thr Leu Asp Cys Ser Pro
                355                 360                 365

Arg Thr Gly Leu Asp Phe Asn Glu Met Val Leu Leu Thr Met Glu Lys
                370                 375                 380

Lys Ser Trp Leu Val His Lys Gln Trp Phe Leu Asp Leu Pro Leu Pro
385                 390                 395                 400

Trp Thr Ser Gly Ala Ser Thr Ser Gln Glu Thr Trp Asn Arg Gln Asp
                405                 410                 415

Leu Leu Val Thr Phe Lys Thr Ala His Ala Lys Lys Gln Glu Val Val
                420                 425                 430

Val Leu Gly Ser Gln Glu Gly Ala Met His Thr Ala Leu Thr Gly Ala
                435                 440                 445

Thr Glu Ile Gln Thr Ser Gly Thr Thr Thr Ile Phe Ala Gly His Leu
                450                 455                 460

Lys Cys Arg Leu Lys Met Asp Lys Leu Thr Leu Lys Gly Met Ser Tyr
465                 470                 475                 480

Val Met Cys Thr Gly Ser Phe Lys Leu Glu Lys Glu Val Ala Glu Thr
                485                 490                 495

Gln His Gly Thr Val Leu Val Gln Val Lys Tyr Glu Gly Thr Asp Ala
                500                 505                 510

Pro Cys Lys Ile Pro Phe Ser Ser Gln Asp Glu Lys Gly Val Thr Gln
                515                 520                 525

Asn Gly Arg Leu Ile Thr Ala Asn Pro Ile Val Thr Asp Lys Glu Lys
530                 535                 540

Pro Val Asn Ile Glu Ala Glu Pro Pro Phe Gly Glu Ser Tyr Ile Val
545                 550                 555                 560

Val Gly Ala Gly Glu Lys Ala Leu Lys Leu Ser Trp Phe Lys Lys Gly
                565                 570                 575

Ser Ser Ile Gly Lys Met Phe Glu Ala Thr Ala Arg Gly Ala Arg Arg
                580                 585                 590

Met Ala Ile Leu Gly Asp Thr Ala Trp Asp Phe Gly Ser Ile Gly Gly
                595                 600                 605

Val Phe Thr Ser Val Gly Lys Leu Ile His Gln Ile Phe Gly Thr Ala
                610                 615                 620

Tyr Gly Val Leu Phe Ser Gly Val Ser Trp Thr Met Lys Ile Gly Ile
625                 630                 635                 640

Gly Ile Leu Leu Thr Trp Leu Gly Leu Asn Ser Arg Ser Thr Ser Leu
                645                 650                 655

Ser Met Thr Cys Ile Ala Val Gly Met Val Thr Leu Tyr Leu Gly Val
                660                 665                 670

Met Val Gln Ala
        675

<210> SEQ ID NO 3
<211> LENGTH: 5498
<212> TYPE: DNA
<213> ORGANISM: Dengue virus
<220> FEATURE:
<221> NAME/KEY: misc_feature
<223> OTHER INFORMATION: DENV1 prM E (Env K203N)
<220> FEATURE:
<221> NAME/KEY: CDS
<222> LOCATION: (1046)..(3073)

<400> SEQUENCE: 3

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg  cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt gacgcgtttg acattgatta     420
ttgactagtt attaatagta atcaattacg ggtcattag  ttcatagccc atatatggag     480
ttccgcgtta cataacttac ggtaaatggc ccgcctggct gaccgcccaa cgaccccgc      540
ccattgacgt caataatgac gtatgttccc atagtaacgc caatagggac tttccattga     600
cgtcaatggg tggagtattt acggtaaact gcccacttgg cagtacatca agtgtatcat     660
atgccaagta cgccccctat tgacgtcaat gacggtaaat ggcccgcctg gcattatgcc     720
cagtacatga ccttatggga ctttcctact tggcagtaca tctacgtatt agtcatcgct     780
attaccatgg tgatgcggtt ttggcagtac atcaatgggc gtggatagcg gtttgactca     840
cggggatttc caagtctcca ccccattgac gtcaatggga gtttgttttg gcaccaaaat     900
caacgggact ttccaaaatg tcgtaacaac tccgccccat tgacgcaaat gggcggtagg     960
cgtgtacggt gggaggtcta tataagcaga gctcgtttag tgaaccgtca gataactgca    1020
ggtcgacgat atcgcggccg ccacc atg tcg gtg acc atg ctc ctc atg ctg      1072
                              Met Ser Val Thr Met Leu Leu Met Leu
                                1               5
ctg ccc aca gcc ctg gcg ttc cat ctg acc acc cga ggg gga gag ccg      1120
Leu Pro Thr Ala Leu Ala Phe His Leu Thr Thr Arg Gly Gly Glu Pro
 10              15                  20                  25
cac atg ata gtt agc aag cag gaa aga gga aaa tca ctt ttg ttt aag      1168
His Met Ile Val Ser Lys Gln Glu Arg Gly Lys Ser Leu Leu Phe Lys
             30                  35                  40
acc tct gca ggt gtc aac atg tgc acc ctt att gca atg gat ttg gga      1216
Thr Ser Ala Gly Val Asn Met Cys Thr Leu Ile Ala Met Asp Leu Gly
         45                  50                  55
gag tta tgt gag gac aca atg acc tac aaa tgc ccc cgg atc act gag      1264
Glu Leu Cys Glu Asp Thr Met Thr Tyr Lys Cys Pro Arg Ile Thr Glu
     60                  65                  70
acg gaa cca gat gac gtt gac tgt tgg tgc aat gcc acg gag aca tgg      1312
Thr Glu Pro Asp Asp Val Asp Cys Trp Cys Asn Ala Thr Glu Thr Trp
 75                  80                  85
gtg acc tat gga aca tgt tct caa act ggt gaa cac cga cga gac aaa      1360
Val Thr Tyr Gly Thr Cys Ser Gln Thr Gly Glu His Arg Arg Asp Lys
 90                  95                 100                 105
cgt tcc gtc gca ctg gca cca cac gta ggg ctt ggt cta gaa aca aga      1408
Arg Ser Val Ala Leu Ala Pro His Val Gly Leu Gly Leu Glu Thr Arg
                110                 115                 120
acc gaa acg tgg atg tcc tct gaa ggc gct tgg aaa caa ata caa aaa      1456
Thr Glu Thr Trp Met Ser Ser Glu Gly Ala Trp Lys Gln Ile Gln Lys
                125                 130                 135
gtg gag acc tgg gct ctg aga cac cca gga ttc acg gtg ata gcc ctt      1504
Val Glu Thr Trp Ala Leu Arg His Pro Gly Phe Thr Val Ile Ala Leu
            140                 145                 150
ttt cta gca cat gcc ata gga aca tcc atc acc cag aaa ggg atc att      1552
Phe Leu Ala His Ala Ile Gly Thr Ser Ile Thr Gln Lys Gly Ile Ile
```

-continued

| | | | | | | | | | | | | | | | | |
|---|---|---|---|---|---|---|---|---|---|---|---|---|---|---|---|---|
| | | 155 | | | | 160 | | | | | 165 | | | | | |
| ttt | att | ttg | ctg | atg | ctg | gta | act | cca | tcc | atg | gcc | atg | cgg | tgc | gtg | 1600 |
| Phe | Ile | Leu | Leu | Met | Leu | Val | Thr | Pro | Ser | Met | Ala | Met | Arg | Cys | Val | |
| 170 | | | | | 175 | | | | | 180 | | | | | 185 | |
| gga | ata | ggc | aac | aga | gac | ttc | gtg | gaa | gga | ctg | tca | gga | gct | acg | tgg | 1648 |
| Gly | Ile | Gly | Asn | Arg | Asp | Phe | Val | Glu | Gly | Leu | Ser | Gly | Ala | Thr | Trp | |
| | | | | | 190 | | | | | 195 | | | | | 200 | |
| gtg | gat | gtg | gta | ctg | gag | cat | gga | agt | tgc | gtc | act | acc | atg | gca | aaa | 1696 |
| Val | Asp | Val | Val | Leu | Glu | His | Gly | Ser | Cys | Val | Thr | Thr | Met | Ala | Lys | |
| | | | | 205 | | | | | 210 | | | | | 215 | | |
| gac | aaa | cca | aca | ctg | gac | att | gaa | ctc | ttg | aag | acg | gag | gtc | aca | aac | 1744 |
| Asp | Lys | Pro | Thr | Leu | Asp | Ile | Glu | Leu | Leu | Lys | Thr | Glu | Val | Thr | Asn | |
| | | | 220 | | | | | 225 | | | | | 230 | | | |
| cct | gcc | gtc | ctg | cgc | aaa | ctg | tgc | att | gaa | gct | aaa | ata | tca | aac | acc | 1792 |
| Pro | Ala | Val | Leu | Arg | Lys | Leu | Cys | Ile | Glu | Ala | Lys | Ile | Ser | Asn | Thr | |
| | | 235 | | | | | 240 | | | | | 245 | | | | |
| acc | acc | gat | tcg | aga | tgt | cca | aca | caa | gga | gaa | gcc | acg | ctg | gtg | gaa | 1840 |
| Thr | Thr | Asp | Ser | Arg | Cys | Pro | Thr | Gln | Gly | Glu | Ala | Thr | Leu | Val | Glu | |
| 250 | | | | | 255 | | | | | 260 | | | | | 265 | |
| gaa | cag | gac | acg | aac | ttt | gtg | tgt | cga | cga | acg | ttc | gtg | gac | aga | ggc | 1888 |
| Glu | Gln | Asp | Thr | Asn | Phe | Val | Cys | Arg | Arg | Thr | Phe | Val | Asp | Arg | Gly | |
| | | | | 270 | | | | | 275 | | | | | 280 | | |
| tgg | ggc | aat | ggt | tgt | ggg | cta | ttc | gga | aaa | ggt | agc | tta | ata | acg | tgt | 1936 |
| Trp | Gly | Asn | Gly | Cys | Gly | Leu | Phe | Gly | Lys | Gly | Ser | Leu | Ile | Thr | Cys | |
| | | | 285 | | | | | 290 | | | | | 295 | | | |
| gct | aag | ttt | aag | tgt | gtg | aca | aaa | ctg | gaa | gga | aag | ata | gtc | caa | tat | 1984 |
| Ala | Lys | Phe | Lys | Cys | Val | Thr | Lys | Leu | Glu | Gly | Lys | Ile | Val | Gln | Tyr | |
| | | 300 | | | | | 305 | | | | | 310 | | | | |
| gaa | aac | tta | aaa | tat | tca | gtg | ata | gtc | acc | gta | cac | act | gga | gac | cag | 2032 |
| Glu | Asn | Leu | Lys | Tyr | Ser | Val | Ile | Val | Thr | Val | His | Thr | Gly | Asp | Gln | |
| | 315 | | | | | 320 | | | | | 325 | | | | | |
| cac | caa | gtt | gga | aat | gag | acc | aca | gaa | cat | gga | aca | act | gca | acc | ata | 2080 |
| His | Gln | Val | Gly | Asn | Glu | Thr | Thr | Glu | His | Gly | Thr | Thr | Ala | Thr | Ile | |
| 330 | | | | | 335 | | | | | 340 | | | | | 345 | |
| aca | cct | caa | gct | ccc | acg | tcg | gaa | ata | cag | ctg | aca | gac | tac | gga | gct | 2128 |
| Thr | Pro | Gln | Ala | Pro | Thr | Ser | Glu | Ile | Gln | Leu | Thr | Asp | Tyr | Gly | Ala | |
| | | | | 350 | | | | | 355 | | | | | 360 | | |
| cta | aca | ttg | gat | tgt | tca | cct | aga | aca | ggg | cta | gac | ttt | aat | gag | atg | 2176 |
| Leu | Thr | Leu | Asp | Cys | Ser | Pro | Arg | Thr | Gly | Leu | Asp | Phe | Asn | Glu | Met | |
| | | | 365 | | | | | 370 | | | | | 375 | | | |
| gtg | ttg | ttg | aca | atg | gaa | aat | aaa | tca | tgg | ctc | gtc | cac | aaa | caa | tgg | 2224 |
| Val | Leu | Leu | Thr | Met | Glu | Asn | Lys | Ser | Trp | Leu | Val | His | Lys | Gln | Trp | |
| | | 380 | | | | | 385 | | | | | 390 | | | | |
| ttt | cta | gac | tta | cca | ctg | cct | tgg | acc | tcg | ggg | gct | tca | aca | tcc | caa | 2272 |
| Phe | Leu | Asp | Leu | Pro | Leu | Pro | Trp | Thr | Ser | Gly | Ala | Ser | Thr | Ser | Gln | |
| | 395 | | | | | 400 | | | | | 405 | | | | | |
| gag | act | tgg | aat | aga | caa | gac | ttg | ctg | gtc | aca | ttt | aag | aca | gct | cat | 2320 |
| Glu | Thr | Trp | Asn | Arg | Gln | Asp | Leu | Leu | Val | Thr | Phe | Lys | Thr | Ala | His | |
| 410 | | | | | 415 | | | | | 420 | | | | | 425 | |
| gca | aaa | aag | cag | gaa | gta | gtc | gta | cta | gga | tca | caa | gaa | gga | gca | atg | 2368 |
| Ala | Lys | Lys | Gln | Glu | Val | Val | Val | Leu | Gly | Ser | Gln | Glu | Gly | Ala | Met | |
| | | | | 430 | | | | | 435 | | | | | 440 | | |
| cac | act | gcg | ttg | act | gga | gcg | aca | gaa | atc | caa | acg | tct | gga | acg | aca | 2416 |
| His | Thr | Ala | Leu | Thr | Gly | Ala | Thr | Glu | Ile | Gln | Thr | Ser | Gly | Thr | Thr | |
| | | | 445 | | | | | 450 | | | | | 455 | | | |
| aca | att | ttt | gca | gga | cac | ctg | aaa | tgc | aga | cta | aaa | atg | gat | aaa | ctg | 2464 |
| Thr | Ile | Phe | Ala | Gly | His | Leu | Lys | Cys | Arg | Leu | Lys | Met | Asp | Lys | Leu | |
| | | 460 | | | | | 465 | | | | | 470 | | | | |
| act | tta | aaa | ggg | atg | tca | tat | gta | atg | tgc | aca | ggg | tca | ttc | aag | tta | 2512 |

```
                Thr Leu Lys Gly Met Ser Tyr Val Met Cys Thr Gly Ser Phe Lys Leu
                    475                 480                 485 gag aag gaa gtg gct gag acc cag cat gga act gtt cta gtg cag gtt          2560
Glu Lys Glu Val Ala Glu Thr Gln His Gly Thr Val Leu Val Gln Val
490                 495                 500                 505 aaa tac gaa gga aca gat gca cca tgc aag atc ccc ttc tcg tcc caa          2608
Lys Tyr Glu Gly Thr Asp Ala Pro Cys Lys Ile Pro Phe Ser Ser Gln
                510                 515                 520 gat gag aag gga gta acc cag aat ggg aga ttg ata aca gcc aac ccc          2656
Asp Glu Lys Gly Val Thr Gln Asn Gly Arg Leu Ile Thr Ala Asn Pro
            525                 530                 535 ata gtc act gac aaa gaa aaa cca gtc aac att gaa gcg gag cca cct          2704
Ile Val Thr Asp Lys Glu Lys Pro Val Asn Ile Glu Ala Glu Pro Pro
        540                 545                 550 ttt ggt gag agc tac att gtg gta gga gca ggt gaa aaa gct ttg aaa          2752
Phe Gly Glu Ser Tyr Ile Val Val Gly Ala Gly Glu Lys Ala Leu Lys
    555                 560                 565 cta agc tgg ttc aag aag gga agc agt ata ggg aaa atg ttt gaa gca          2800
Leu Ser Trp Phe Lys Lys Gly Ser Ser Ile Gly Lys Met Phe Glu Ala
570                 575                 580                 585 act gcc cgt gga gca cga agg atg gcc atc ctg gga gac act gca tgg          2848
Thr Ala Arg Gly Ala Arg Arg Met Ala Ile Leu Gly Asp Thr Ala Trp
                590                 595                 600 gac ttc ggt tct ata gga ggg gtg ttc acg tct gtg gga aaa ctg ata          2896
Asp Phe Gly Ser Ile Gly Gly Val Phe Thr Ser Val Gly Lys Leu Ile
                605                 610                 615 cac cag att ttt ggg act gcg tat gga gtt ttg ttc agc ggt gtt tct          2944
His Gln Ile Phe Gly Thr Ala Tyr Gly Val Leu Phe Ser Gly Val Ser
            620                 625                 630 tgg acc atg aag ata gga ata ggg att ctg ctg aca tgg cta gga tta          2992
Trp Thr Met Lys Ile Gly Ile Gly Ile Leu Leu Thr Trp Leu Gly Leu
        635                 640                 645 aac tca agg agc acg tcc ctt tca atg acg tgt atc gca gtt ggc atg          3040
Asn Ser Arg Ser Thr Ser Leu Ser Met Thr Cys Ile Ala Val Gly Met
650                 655                 660                 665 gtc acg ctg tac cta gga gtc atg gtt cag gcg taataaagat ctgctgtgcc        3093
Val Thr Leu Tyr Leu Gly Val Met Val Gln Ala
                670                 675 ttctagttgc cagccatctg ttgtttgccc ctcccccgtg ccttccttga ccctggaagg        3153
tgccactccc actgtccttt cctaataaaa tgaggaaatt gcatcgcatt gtctgagtag        3213
gtgtcattct attctggggg gtggggtggg gcaggacagc aaggggagg attgggaaga         3273 caatagcagg catgctgggg atgcggtggg ctctatggct cgagcatggt catagctgtt        3333
tcctgtgtga aattgttatc cgctcacaat tccacacaac atacgagccg gaagcataaa       3393
gtgtaaagcc tggggtgcct aatgagtgag ctaactcaca ttaattgcgt tgcgctcact        3453
gcccgctttc cagtcgggaa acctgtcgtg ccagctgcat taatgaatcg gccaacgcgc        3513
ggggagaggc ggtttgcgta ttgggcgctc ttccgcttcc tcgctcactg actcgctgcg       3573
ctcggtcgtt cggctgcggc gagcggtatc agctcactca aaggcggtaa tacggttatc        3633
cacagaatca ggggataacg caggaaagaa catgtgagca aaaggccagc aaaaggccag        3693
gaaccgtaaa aaggccgcgt tgctggcgtt tttccatagg ctccgccccc ctgacgagca        3753
tcacaaaaat cgacgctcaa gtcagaggtg gcgaaacccg acaggactat aaagatacca        3813
ggcgtttccc cctggaagct ccctcgtgcg ctctcctgtt ccgaccctgc cgcttaccgg        3873
atacctgtcc gcctttctcc cttcgggaag cgtggcgctt tctcatagct cacgctgtag        3933
```

-continued

| | |
|---|---|
| gtatctcagt tcggtgtagg tcgttcgctc caagctgggc tgtgtgcacg aacccccgt | 3993 |
| tcagcccgac cgctgcgcct tatccggtaa ctatcgtctt gagtccaacc cggtaagaca | 4053 |
| cgacttatcg ccactggcag cagccactgg taacaggatt agcagagcga ggtatgtagg | 4113 |
| cggtgctaca gagttcttga agtggtggcc taactacggc tacactagaa gaacagtatt | 4173 |
| tggtatctgc gctctgctga agccagttac cttcggaaaa agagttggta gctcttgatc | 4233 |
| cggcaaacaa accaccgctg gtagcggtgg ttttttttgtt tgcaagcagc agattacgcg | 4293 |
| cagaaaaaaa ggatctcaag aagatccttt gatcttttct acggggtctg acgctcagtg | 4353 |
| gaacgaaaac tcacgttaag ggattttggt catgagatta tcaaaaagga tcttcaccta | 4413 |
| gatccttta aattaaaaat gaagttttaa atcaatctaa agtatatatg agtaaacttg | 4473 |
| gtctgacagt tagaaaaact catcgagcat caaatgaaac tgcaatttat tcatatcagg | 4533 |
| attatcaata ccatattttt gaaaaagccg tttctgtaat gaaggagaaa actcaccgag | 4593 |
| gcagttccat aggatggcaa gatcctggta tcggtctgcg attccgactc gtccaacatc | 4653 |
| aatacaacct attaatttcc cctcgtcaaa ataaggtta tcaagtgaga atcaccatg | 4713 |
| agtgacgact gaatccggtg agaatggcaa aagtttatgc atttctttcc agacttgttc | 4773 |
| aacaggccag ccattacgct cgtcatcaaa atcactcgca tcaaccaaac cgttattcat | 4833 |
| tcgtgattgc gcctgagcga gacgaaatac gcgatcgctg ttaaaaggac aattacaaac | 4893 |
| aggaatcgaa tgcaaccggc gcaggaacac tgccagcgca tcaacaatat tttcacctga | 4953 |
| atcaggatat tcttctaata cctggaatgc tgttttccca gggatcgcag tggtgagtaa | 5013 |
| ccatgcatca tcaggagtac ggataaaatg cttgatggtc ggaagaggca taaattccgt | 5073 |
| cagccagttt agtctgacca tctcatctgt aacatcattg caacgctac ctttgccatg | 5133 |
| tttcagaaac aactctggcg catcgggctt cccatacaat cgatagattg tcgcacctga | 5193 |
| ttgcccgaca ttatcgcgag cccatttata cccatataaa tcagcatcca tgttggaatt | 5253 |
| taatcgcggc ctagagcaag acgtttcccg ttgaatatgg ctcatactct cctttttca | 5313 |
| atattattga agcatttatc agggttattg tctcatgagc ggatacatat ttgaatgtat | 5373 |
| ttagaaaaat aaacaaatag gggttccgcg cacatttccc cgaaaagtgc cacctgacgt | 5433 |
| ctaagaaacc attattatca tgacattaac ctataaaaat aggcgtatca cgaggccctt | 5493 |
| tcgtc | 5498 |

<210> SEQ ID NO 4
<211> LENGTH: 676
<212> TYPE: PRT
<213> ORGANISM: Dengue virus

<400> SEQUENCE: 4

```
Met Ser Val Thr Met Leu Leu Met Leu Leu Pro Thr Ala Leu Ala Phe
1               5                   10                  15

His Leu Thr Thr Arg Gly Gly Glu Pro His Met Ile Val Ser Lys Gln
            20                  25                  30

Glu Arg Gly Lys Ser Leu Leu Phe Lys Thr Ser Ala Gly Val Asn Met
        35                  40                  45

Cys Thr Leu Ile Ala Met Asp Leu Gly Glu Leu Cys Glu Asp Thr Met
    50                  55                  60

Thr Tyr Lys Cys Pro Arg Ile Thr Glu Thr Glu Pro Asp Asp Val Asp
65                  70                  75                  80

Cys Trp Cys Asn Ala Thr Glu Thr Trp Val Thr Tyr Gly Thr Cys Ser
                85                  90                  95
```

```
Gln Thr Gly Glu His Arg Arg Asp Lys Arg Ser Val Ala Leu Ala Pro
            100                 105                 110

His Val Gly Leu Gly Leu Glu Thr Arg Thr Glu Thr Trp Met Ser Ser
            115                 120                 125

Glu Gly Ala Trp Lys Gln Ile Gln Lys Val Glu Thr Trp Ala Leu Arg
            130                 135                 140

His Pro Gly Phe Thr Val Ile Ala Leu Phe Leu Ala His Ala Ile Gly
145                 150                 155                 160

Thr Ser Ile Thr Gln Lys Gly Ile Ile Phe Ile Leu Leu Met Leu Val
                165                 170                 175

Thr Pro Ser Met Ala Met Arg Cys Val Gly Ile Gly Asn Arg Asp Phe
            180                 185                 190

Val Glu Gly Leu Ser Gly Ala Thr Trp Val Asp Val Val Leu Glu His
            195                 200                 205

Gly Ser Cys Val Thr Thr Met Ala Lys Asp Lys Pro Thr Leu Asp Ile
            210                 215                 220

Glu Leu Leu Lys Thr Glu Val Thr Asn Pro Ala Val Leu Arg Lys Leu
225                 230                 235                 240

Cys Ile Glu Ala Lys Ile Ser Asn Thr Thr Thr Asp Ser Arg Cys Pro
                245                 250                 255

Thr Gln Gly Glu Ala Thr Leu Val Glu Glu Gln Asp Thr Asn Phe Val
            260                 265                 270

Cys Arg Arg Thr Phe Val Asp Arg Gly Trp Gly Asn Gly Cys Gly Leu
            275                 280                 285

Phe Gly Lys Gly Ser Leu Ile Thr Cys Ala Lys Phe Lys Cys Val Thr
            290                 295                 300

Lys Leu Glu Gly Lys Ile Val Gln Tyr Glu Asn Leu Lys Tyr Ser Val
305                 310                 315                 320

Ile Val Thr Val His Thr Gly Asp Gln His Gln Val Gly Asn Glu Thr
                325                 330                 335

Thr Glu His Gly Thr Thr Ala Thr Ile Thr Pro Gln Ala Pro Thr Ser
            340                 345                 350

Glu Ile Gln Leu Thr Asp Tyr Gly Ala Leu Thr Leu Asp Cys Ser Pro
            355                 360                 365

Arg Thr Gly Leu Asp Phe Asn Glu Met Val Leu Leu Thr Met Glu Asn
370                 375                 380

Lys Ser Trp Leu Val His Lys Gln Trp Phe Leu Asp Leu Pro Leu Pro
385                 390                 395                 400

Trp Thr Ser Gly Ala Ser Thr Ser Gln Glu Thr Trp Asn Arg Gln Asp
            405                 410                 415

Leu Leu Val Thr Phe Lys Thr Ala His Ala Lys Lys Gln Glu Val Val
            420                 425                 430

Val Leu Gly Ser Gln Glu Gly Ala Met His Thr Ala Leu Thr Gly Ala
            435                 440                 445

Thr Glu Ile Gln Thr Ser Gly Thr Thr Thr Ile Phe Ala Gly His Leu
            450                 455                 460

Lys Cys Arg Leu Lys Met Asp Lys Leu Thr Leu Lys Gly Met Ser Tyr
465                 470                 475                 480

Val Met Cys Thr Gly Ser Phe Lys Leu Glu Lys Glu Val Ala Glu Thr
            485                 490                 495

Gln His Gly Thr Val Leu Val Gln Val Lys Tyr Glu Gly Thr Asp Ala
            500                 505                 510
```

```
Pro Cys Lys Ile Pro Phe Ser Ser Gln Asp Glu Lys Gly Val Thr Gln
        515                 520                 525

Asn Gly Arg Leu Ile Thr Ala Asn Pro Ile Val Thr Asp Lys Glu Lys
    530                 535                 540

Pro Val Asn Ile Glu Ala Glu Pro Pro Phe Gly Glu Ser Tyr Ile Val
545                 550                 555                 560
Val Gly Ala Gly Glu Lys Ala Leu Lys Leu Ser Trp Phe Lys Lys Gly
                565                 570                 575
Ser Ser Ile Gly Lys Met Phe Glu Ala Thr Ala Arg Gly Ala Arg Arg
            580                 585                 590
Met Ala Ile Leu Gly Asp Thr Ala Trp Asp Phe Gly Ser Ile Gly Gly
        595                 600                 605
Val Phe Thr Ser Val Gly Lys Leu Ile His Gln Ile Phe Gly Thr Ala
    610                 615                 620
Tyr Gly Val Leu Phe Ser Gly Val Ser Trp Thr Met Lys Ile Gly Ile
625                 630                 635                 640
Gly Ile Leu Leu Thr Trp Leu Gly Leu Asn Ser Arg Ser Thr Ser Leu
                645                 650                 655
Ser Met Thr Cys Ile Ala Val Gly Met Val Thr Leu Tyr Leu Gly Val
            660                 665                 670
Met Val Gln Ala
        675

<210> SEQ ID NO 5
<211> LENGTH: 3770
<212> TYPE: DNA
<213> ORGANISM: Dengue virus
<220> FEATURE:
<221> NAME/KEY: misc_feature
<223> OTHER INFORMATION: DENV1 capsid K85A_K86A mutant
<220> FEATURE:
<221> NAME/KEY: CDS
<222> LOCATION: (1046)..(1345)

<400> SEQUENCE: 5
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt gacgcgtttg acattgatta     420
ttgactagtt attaatagta atcaattacg gggtcattag ttcatagccc atatatggag     480
ttccgcgtta cataacttac ggtaaatggc ccgcctggct gaccgcccaa cgacccccgc     540
ccattgacgt caataatgac gtatgttccc atagtaacgc caatagggac tttccattga     600
cgtcaatggg tggagtattt acggtaaact gcccacttgg cagtacatca agtgtatcat     660
atgccaagta cgccccctat tgacgtcaat gacggtaaat ggcccgcctg gcattatgcc     720
cagtacatga ccttatggga ctttcctact tggcagtaca tctacgtatt agtcatcgct     780
attaccatgg tgatgcggtt ttggcagtac atcaatgggc gtggatagcg gtttgactca     840
cggggatttc caagtctcca ccccattgac gtcaatggga gtttgttttg gcaccaaaat     900
caacgggact ttccaaaatg tcgtaacaac tccgccccat tgacgcaaat gggcggtagg     960
```

```
cgtgtacggt gggaggtcta tataagcaga gctcgtttag tgaaccgtca gataactgca        1020
ggtcgacgat atcgcggccg ccacc atg aac aac caa cgg aaa aag acg ggt         1072
                            Met Asn Asn Gln Arg Lys Lys Thr Gly
                            1               5 cga ccg tct ttc aat atg ctg aaa cgc gcg aga aac cgc gtg tca act         1120
Arg Pro Ser Phe Asn Met Leu Lys Arg Ala Arg Asn Arg Val Ser Thr
10              15                  20                  25 gtt tca cag ttg gcg aag aga ttc tca aaa gga ttg ctt tca ggc caa         1168
Val Ser Gln Leu Ala Lys Arg Phe Ser Lys Gly Leu Leu Ser Gly Gln
            30                  35                  40 gga ccc atg aaa ttg gtg atg gct ttt ata gca ttc cta aga ttt cta         1216
Gly Pro Met Lys Leu Val Met Ala Phe Ile Ala Phe Leu Arg Phe Leu
        45                  50                  55 gcc ata cct cca aca gca gga att ttg gct aga tgg ggc tca ttc aag         1264
Ala Ile Pro Pro Thr Ala Gly Ile Leu Ala Arg Trp Gly Ser Phe Lys
60              65                  70 aag aat gga gcg atc aaa gtg tta cgg ggt ttc gcg gca gaa atc tca         1312
Lys Asn Gly Ala Ile Lys Val Leu Arg Gly Phe Ala Ala Glu Ile Ser
75                  80                  85 aac atg ttg aac ata atg aac agg agg aaa aga taataaagat ctgctgtgcc       1365
Asn Met Leu Asn Ile Met Asn Arg Arg Lys Arg
90              95                  100 ttctagttgc cagccatctg ttgtttgccc ctccccgtg ccttccttga ccctggaagg        1425
tgccactccc actgtccttt cctaataaaa tgaggaaatt gcatcgcatt gtctgagtag       1485
gtgtcattct attctggggg gtggggtggg gcaggacagc aaggggagg attgggaaga        1545
caatagcagg catgctgggg atgcgtgggg ctctatggct cgagcatggt catagctgtt       1605
tcctgtgtga aattgttatc cgctcacaat tccacacaac atacgagccg gaagcataaa       1665
gtgtaaagcc tggggtgcct aatgagtgag ctaactcaca ttaattgcgt tgcgctcact       1725
gcccgctttc cagtcgggaa acctgtcgtg ccagctgcat taatgaatcg gccaacgcgc       1785
ggggagaggc ggtttgcgta ttgggcgctc ttccgcttcc tcgctcactg actcgctgcg       1845
ctcggtcgtt cggctgcggc gagcggtatc agctcactca aaggcggtaa tacggttatc       1905
cacagaatca gggataacg caggaaagaa catgtgagca aaaggccagc aaaaggccag        1965
gaaccgtaaa aaggccgcgt tgctggcgtt tttccatagg ctccgccccc ctgacgagca       2025
tcacaaaaat cgacgctcaa gtcagaggtg gcgaaacccg acaggactat aaagatacca       2085
ggcgtttccc cctggaagct ccctcgtgcg ctctcctgtt ccgaccctgc cgcttaccgg       2145
atacctgtcc gcctttctcc cttcgggaag cgtggcgctt tctcatagct cacgctgtag       2205
gtatctcagt tcggtgtagg tcgttcgctc caagctgggc tgtgtgcacg aaccccccgt       2265
tcagcccgac cgctgcgcct tatccggtaa ctatcgtctt gagtccaacc cggtaagaca       2325
cgacttatcg ccactggcag cagccactgg taacaggatt agcagagcga ggtatgtagg       2385
cggtgctaca gagttcttga agtggtggcc taactacggc tacactagaa gaacagtatt       2445
tggtatctgc gctctgctga agccagttac cttcggaaaa agagttggta gctcttgatc       2505
cggcaaacaa accaccgctg gtagcggtgg tttttttgtt tgcaagcagc agattacgcg       2565
cagaaaaaaa ggatctcaag aagatccttt gatcttttct acggggtctg acgctcagtg       2625
gaacgaaaac tcacgttaag ggattttggt catgagatta tcaaaaagga tcttcaccta       2685
gatcctttta aattaaaaat gaagttttaa atcaatctaa agtatatatg agtaaacttg       2745
gtctgacagt tagaaaaact catcgagcat caaatgaaac tgcaatttat tcatatcagg       2805
attatcaata ccatattttt gaaaaagccg tttctgtaat gaaggagaaa actcaccgag       2865
```

-continued

```
gcagttccat aggatggcaa gatcctggta tcggtctgcg attccgactc gtccaacatc    2925
aatacaacct attaatttcc cctcgtcaaa aataaggtta tcaagtgaga atcaccatg     2985 agtgacgact gaatccggtg agaatggcaa aagtttatgc atttctttcc agacttgttc   3045
aacaggccag ccattacgct cgtcatcaaa atcactcgca tcaaccaaac cgttattcat   3105
tcgtgattgc gcctgagcga gacgaaatac gcgatcgctg ttaaaaggac aattacaaac   3165
aggaatcgaa tgcaaccggc gcaggaacac tgccagcgca tcaacaatat tttcacctga   3225
atcaggatat tcttctaata cctggaatgc tgttttccca gggatcgcag tggtgagtaa   3285
ccatgcatca tcaggagtac ggataaaatg cttgatggtc ggaagaggca taaattccgt   3345
cagccagttt agtctgacca tctcatctgt aacatcattg caacgctac ctttgccatg    3405 tttcagaaac aactctggcg catcgggctt cccatacaat cgatagattg tcgcacctga   3465 ttgccccgaca ttatcgcgag cccatttata cccatataaa tcagcatcca tgttggaatt   3525
taatcgcggc ctagagcaag acgtttcccg ttgaatatgg ctcatactct tcctttttca   3585
atattattga agcatttatc agggttattg tctcatgagc ggatacatat ttgaatgtat   3645
ttagaaaaat aaacaaatag gggttccgcg cacatttccc cgaaaagtgc cacctgacgt   3705
ctaagaaacc attattatca tgacattaac ctataaaaat aggcgtatca cgaggccctt   3765
tcgtc                                                              3770
```

<210> SEQ ID NO 6
<211> LENGTH: 100
<212> TYPE: PRT
<213> ORGANISM: Dengue virus

<400> SEQUENCE: 6

```
Met Asn Asn Gln Arg Lys Lys Thr Gly Arg Pro Ser Phe Asn Met Leu
1               5                   10                  15

Lys Arg Ala Arg Asn Arg Val Ser Thr Val Ser Gln Leu Ala Lys Arg
            20                  25                  30

Phe Ser Lys Gly Leu Leu Ser Gly Gln Gly Pro Met Lys Leu Val Met
        35                  40                  45

Ala Phe Ile Ala Phe Leu Arg Phe Leu Ala Ile Pro Pro Thr Ala Gly
    50                  55                  60

Ile Leu Ala Arg Trp Gly Ser Phe Lys Lys Asn Gly Ala Ile Lys Val
65                  70                  75                  80

Leu Arg Gly Phe Ala Ala Glu Ile Ser Asn Met Leu Asn Ile Met Asn
                85                  90                  95

Arg Arg Lys Arg
            100
```

<210> SEQ ID NO 7
<211> LENGTH: 6679
<212> TYPE: DNA
<213> ORGANISM: Dengue virus
<220> FEATURE:
<221> NAME/KEY: misc_feature
<223> OTHER INFORMATION: Chimera DENV2 prM E_chimeric DENV1 E
<220> FEATURE:
<221> NAME/KEY: CDS
<222> LOCATION: (906)..(2933)
<220> FEATURE:
<221> NAME/KEY: misc_feature
<222> LOCATION: (906)..(2336)
<223> OTHER INFORMATION: DENV2 prM E region
<220> FEATURE:
<221> NAME/KEY: misc_feature
<222> LOCATION: (2337)..(2933)
<223> OTHER INFORMATION: DENV1 E region

<400> SEQUENCE: 7

```
gaattcccat tgcatacgtt gtatccatat cataatatgt acatttatat tggctcatgt      60
ccaacattac cgccatgttg acattgatta ttgactagtt attaatagta atcaattacg     120
gggtcattag ttcatagccc atatatggag ttccgcgtta cataacttac ggtaaatggc     180
ccgcctggct gaccgcccaa cgaccccgc ccattgacgt caataatgac gtatgttccc      240
atagtaacgc caatagggac tttccattga cgtcaatggg tggagtattt acggtaaact     300
gcccacttgg cagtacatca agtgtatcat atgccaagta cgccccctat tgacgtcaat     360
gacggtaaat ggcccgcctg gcattatgcc cagtacatga ccttatggga ctttcctact     420
tggcagtaca tctacgtatt agtcatcgct attaccatgg tgatgcggtt ttggcagtac     480
atcaatgggc gtggatagcg gtttgactca cggggatttc caagtctcca ccccattgac     540
gtcaatggga gtttgttttg gcaccaaaat caacgggact ttccaaaatg tcgtaacaac     600
tccgccccat tgacgcaaat gggcggtagg cgtgtacggt gggaggtcta tataagcaga     660
gctcgtttag tgaaccgtca gatcgcctgg agacgccatc cacgctgttt tgacctccat     720
agaagacacc gggaccgatc cagcctccgt taacggtgga gggcagtgta gtctgagcag     780
tactcgttgc tgccgcgcgc gccaccagac ataatagctg acagactaac agactgttcc     840
tttccatggg tcttttctgc agtcaccgtc gtcgacacgt gtgatcagat atcgcggccg     900
ccacc atg act gca ggc atg atc atc atg ctg att cca aca gtg atg gcg     950
      Met Thr Ala Gly Met Ile Ile Met Leu Ile Pro Thr Val Met Ala
      1               5                   10                  15
ttt cat ctg acc aca cgc aac gga gaa cca cac atg atc gtc agt aga      998
Phe His Leu Thr Thr Arg Asn Gly Glu Pro His Met Ile Val Ser Arg
                20                  25                  30
caa gaa aaa ggg aaa agc ctt ctg ttt aag aca aag gac ggc acg aac     1046
Gln Glu Lys Gly Lys Ser Leu Leu Phe Lys Thr Lys Asp Gly Thr Asn
            35                  40                  45
atg tgt acc ctc atg gcc atg gac ctt ggt gag ttg tgt gaa gac aca     1094
Met Cys Thr Leu Met Ala Met Asp Leu Gly Glu Leu Cys Glu Asp Thr
        50                  55                  60
atc acg tat aaa tgt ccc ttt ctc aag cag aac gaa cca gaa gac ata     1142
Ile Thr Tyr Lys Cys Pro Phe Leu Lys Gln Asn Glu Pro Glu Asp Ile
    65                  70                  75
gat tgt tgg tgc aac tcc acg tcc aca tgg gta act tat ggg aca tgt     1190
Asp Cys Trp Cys Asn Ser Thr Ser Thr Trp Val Thr Tyr Gly Thr Cys
80                  85                  90                  95
acc acc aca gga gag cac aga aga gaa aaa aga tca gtg gcg ctt gtt     1238
Thr Thr Thr Gly Glu His Arg Arg Glu Lys Arg Ser Val Ala Leu Val
                100                 105                 110
cca cac gtg gga atg gga ttg gag aca cga act gaa aca tgg atg tca     1286
Pro His Val Gly Met Gly Leu Glu Thr Arg Thr Glu Thr Trp Met Ser
            115                 120                 125
tca gaa ggg gcc tgg aaa cat gcc cag aga att gaa act tgg att ctg     1334
Ser Glu Gly Ala Trp Lys His Ala Gln Arg Ile Glu Thr Trp Ile Leu
        130                 135                 140
aga cat cca ggc ttt acc ata atg gcc gca atc ctg gca tac acc ata     1382
Arg His Pro Gly Phe Thr Ile Met Ala Ala Ile Leu Ala Tyr Thr Ile
    145                 150                 155
gga acg acg cat ttc caa aga gtc ctg ata ttc atc cta ctg aca gcc     1430
Gly Thr Thr His Phe Gln Arg Val Leu Ile Phe Ile Leu Leu Thr Ala
160                 165                 170                 175
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| atc | gct | cct | tca | atg | aca | atg | cgc | tgc | ata | gga | ata | tca | aat | agg | gac | 1478 |
| Ile | Ala | Pro | Ser | Met | Thr | Met | Arg | Cys | Ile | Gly | Ile | Ser | Asn | Arg | Asp |      |
|     |     |     | 180 |     |     |     |     | 185 |     |     |     |     | 190 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ttt | gtg | gaa | gga | gtg | tca | gga | ggg | agt | tgg | gtt | gac | ata | gtt | tta | gaa | 1526 |
| Phe | Val | Glu | Gly | Val | Ser | Gly | Gly | Ser | Trp | Val | Asp | Ile | Val | Leu | Glu |      |
|     |     |     | 195 |     |     |     |     | 200 |     |     |     |     | 205 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cat | gga | agt | tgt | gtg | acg | acg | atg | gca | aaa | aat | aaa | cca | aca | ctg | gac | 1574 |
| His | Gly | Ser | Cys | Val | Thr | Thr | Met | Ala | Lys | Asn | Lys | Pro | Thr | Leu | Asp |      |
|     |     | 210 |     |     |     |     | 215 |     |     |     |     | 220 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ttt | gaa | ctg | ata | aaa | aca | gaa | gcc | aaa | caa | ccc | gcc | acc | tta | agg | aag | 1622 |
| Phe | Glu | Leu | Ile | Lys | Thr | Glu | Ala | Lys | Gln | Pro | Ala | Thr | Leu | Arg | Lys |      |
|     | 225 |     |     |     |     | 230 |     |     |     |     | 235 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tac | tgt | ata | gag | gct | aaa | ctg | acc | aac | acg | aca | aca | gac | tcg | cgc | tgc | 1670 |
| Tyr | Cys | Ile | Glu | Ala | Lys | Leu | Thr | Asn | Thr | Thr | Thr | Asp | Ser | Arg | Cys |      |
| 240 |     |     |     |     | 245 |     |     |     |     | 250 |     |     |     |     | 255 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cca | aca | caa | ggg | gaa | ccc | acc | ctg | aat | gaa | gag | cag | gac | aaa | agg | ttt | 1718 |
| Pro | Thr | Gln | Gly | Glu | Pro | Thr | Leu | Asn | Glu | Glu | Gln | Asp | Lys | Arg | Phe |      |
|     |     |     | 260 |     |     |     |     | 265 |     |     |     |     | 270 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtc | tgc | aaa | cat | tcc | atg | gta | gac | aga | gga | tgg | gga | aat | gga | tgt | gga | 1766 |
| Val | Cys | Lys | His | Ser | Met | Val | Asp | Arg | Gly | Trp | Gly | Asn | Gly | Cys | Gly |      |
|     |     |     | 275 |     |     |     |     | 280 |     |     |     |     | 285 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tta | ttt | gga | aaa | gga | ggc | atc | gtg | acc | tgt | gcc | atg | ttc | aca | tgc | aaa | 1814 |
| Leu | Phe | Gly | Lys | Gly | Gly | Ile | Val | Thr | Cys | Ala | Met | Phe | Thr | Cys | Lys |      |
|     |     | 290 |     |     |     |     | 295 |     |     |     |     | 300 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aag | aac | atg | gag | gga | aaa | att | gtg | cag | cca | gaa | aac | ctg | gaa | tac | act | 1862 |
| Lys | Asn | Met | Glu | Gly | Lys | Ile | Val | Gln | Pro | Glu | Asn | Leu | Glu | Tyr | Thr |      |
|     | 305 |     |     |     |     | 310 |     |     |     |     | 315 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtc | gtt | ata | aca | cct | cat | tca | ggg | gaa | gaa | cat | gca | gtc | gga | aat | gac | 1910 |
| Val | Val | Ile | Thr | Pro | His | Ser | Gly | Glu | Glu | His | Ala | Val | Gly | Asn | Asp |      |
| 320 |     |     |     |     | 325 |     |     |     |     | 330 |     |     |     |     | 335 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aca | gga | aaa | cat | ggt | aaa | gaa | gtc | aag | ata | aca | cca | cag | agc | tcc | atc | 1958 |
| Thr | Gly | Lys | His | Gly | Lys | Glu | Val | Lys | Ile | Thr | Pro | Gln | Ser | Ser | Ile |      |
|     |     |     | 340 |     |     |     |     | 345 |     |     |     |     | 350 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aca | gag | gcg | gaa | ctg | aca | ggc | tat | ggc | act | gtt | acg | atg | gag | tgc | tct | 2006 |
| Thr | Glu | Ala | Glu | Leu | Thr | Gly | Tyr | Gly | Thr | Val | Thr | Met | Glu | Cys | Ser |      |
|     |     | 355 |     |     |     |     | 360 |     |     |     |     | 365 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cca | aga | acg | ggc | ctc | gac | ttc | aat | gag | atg | gtg | ttg | ctg | caa | atg | aaa | 2054 |
| Pro | Arg | Thr | Gly | Leu | Asp | Phe | Asn | Glu | Met | Val | Leu | Leu | Gln | Met | Lys |      |
|     | 370 |     |     |     |     | 375 |     |     |     |     | 380 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gac | aaa | gct | tgg | ctg | gtg | cac | aga | caa | tgg | ttc | cta | gac | cta | ccg | ttg | 2102 |
| Asp | Lys | Ala | Trp | Leu | Val | His | Arg | Gln | Trp | Phe | Leu | Asp | Leu | Pro | Leu |      |
| 385 |     |     |     |     | 390 |     |     |     |     | 395 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cca | tgg | ctg | ccc | gga | gca | gac | aca | caa | gga | tca | aat | tgg | ata | cag | aaa | 2150 |
| Pro | Trp | Leu | Pro | Gly | Ala | Asp | Thr | Gln | Gly | Ser | Asn | Trp | Ile | Gln | Lys |      |
| 400 |     |     |     |     | 405 |     |     |     |     | 410 |     |     |     |     | 415 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gag | aca | ctg | gtc | acc | ttc | aaa | aat | ccc | cat | gcg | aaa | aaa | cag | gat | gtt | 2198 |
| Glu | Thr | Leu | Val | Thr | Phe | Lys | Asn | Pro | His | Ala | Lys | Lys | Gln | Asp | Val |      |
|     |     |     |     | 420 |     |     |     |     | 425 |     |     |     |     | 430 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtt | gtc | tta | ggc | tcc | caa | gag | ggg | gcc | atg | cat | aca | gca | ctc | aca | ggg | 2246 |
| Val | Val | Leu | Gly | Ser | Gln | Glu | Gly | Ala | Met | His | Thr | Ala | Leu | Thr | Gly |      |
|     |     |     | 435 |     |     |     |     | 440 |     |     |     |     | 445 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gct | acg | gaa | atc | cag | atg | tca | tca | gga | aac | ctg | ctg | ttc | aca | gga | cat | 2294 |
| Ala | Thr | Glu | Ile | Gln | Met | Ser | Ser | Gly | Asn | Leu | Leu | Phe | Thr | Gly | His |      |
|     |     | 450 |     |     |     |     | 455 |     |     |     |     | 460 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctt | aag | tgc | agg | ctg | aga | atg | gac | aaa | tta | caa | ctt | aaa | ggg | atg | tca | 2342 |
| Leu | Lys | Cys | Arg | Leu | Arg | Met | Asp | Lys | Leu | Gln | Leu | Lys | Gly | Met | Ser |      |
|     | 465 |     |     |     |     | 470 |     |     |     |     | 475 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tat | gta | atg | tgc | aca | ggg | tca | ttc | aag | tta | gag | aag | gaa | gtg | gct | gag | 2390 |
| Tyr | Val | Met | Cys | Thr | Gly | Ser | Phe | Lys | Leu | Glu | Lys | Glu | Val | Ala | Glu |      |
| 480 |     |     |     |     | 485 |     |     |     |     | 490 |     |     |     |     | 495 |      |

```
acc cag cat gga act gtt cta gtg cag gtt aaa tac gaa gga aca gat      2438
Thr Gln His Gly Thr Val Leu Val Gln Val Lys Tyr Glu Gly Thr Asp
            500                 505                 510 gca cca tgc aag atc ccc ttc tcg tcc caa gat gag aag gga gta acc      2486
Ala Pro Cys Lys Ile Pro Phe Ser Ser Gln Asp Glu Lys Gly Val Thr
        515                 520                 525 cag aat ggg aga ttg ata aca gcc aac ccc ata gtc act gac aaa gaa      2534
Gln Asn Gly Arg Leu Ile Thr Ala Asn Pro Ile Val Thr Asp Lys Glu
    530                 535                 540 aaa cca gtc aac att gaa gcg gag cca cct ttt ggt gag agc tac att      2582
Lys Pro Val Asn Ile Glu Ala Glu Pro Pro Phe Gly Glu Ser Tyr Ile
545                 550                 555 gtg gta gga gca ggt gaa aaa gct ttg aaa cta agc tgg ttc aag aag      2630
Val Val Gly Ala Gly Glu Lys Ala Leu Lys Leu Ser Trp Phe Lys Lys
560                 565                 570                 575 gga agc agt ata ggg aaa atg ttt gaa gca act gcc cgt gga gca cga      2678
Gly Ser Ser Ile Gly Lys Met Phe Glu Ala Thr Ala Arg Gly Ala Arg
            580                 585                 590 agg atg gcc atc ctg gga gac act gca tgg gac ttc ggt tct ata gga      2726
Arg Met Ala Ile Leu Gly Asp Thr Ala Trp Asp Phe Gly Ser Ile Gly
        595                 600                 605 ggg gtg ttc acg tct gtg gga aaa ctg ata cac cag att ttt ggg act      2774
Gly Val Phe Thr Ser Val Gly Lys Leu Ile His Gln Ile Phe Gly Thr
    610                 615                 620 gcg tat gga gtt ttg ttc agc ggt gtt tct tgg acc atg aag ata gga      2822
Ala Tyr Gly Val Leu Phe Ser Gly Val Ser Trp Thr Met Lys Ile Gly
625                 630                 635 ata ggg att ctg ctg aca tgg cta gga tta aac tca agg agc acg tcc      2870
Ile Gly Ile Leu Leu Thr Trp Leu Gly Leu Asn Ser Arg Ser Thr Ser
640                 645                 650                 655 ctt tca atg acg tgt atc gca gtt ggc atg gtc acg ctg tac cta gga      2918
Leu Ser Met Thr Cys Ile Ala Val Gly Met Val Thr Leu Tyr Leu Gly
            660                 665                 670 gtc atg gtt cag gcg taataaagat ctgctgtgcc ttctagttgc cagccatctg      2973
Val Met Val Gln Ala
            675 ttgtttgccc ctcccccgtg ccttccttga ccctggaagg tgccactccc actgtccttt      3033 cctaataaaa tgaggaaatt gcatcgcatt gtctgagtag gtgtcattct attctggggg      3093 gtggggtggg gcaggacagc aaggggagg attgggaaga caatagcagg catgctgggg      3153 atgcggtggg ctctatgggt acccaggtgc tgaagaattg acccggttcc tcctgggcca      3213 gaaagaagca ggcacatccc cttctctgtg acacaccctg tccacgcccc tggttcttag      3273 ttccagcccc actcatagga cactcatagc tcaggagggc tccgccttca atcccacccg      3333 ctaaagtact tggagcggtc tctccctccc tcatcagccc accaaaccaa acctagcctc      3393 caagagtggg aagaaattaa agcaagatag gctattaagt gcagagggag agaaaatgcc      3453 tccaacatgt gaggaagtaa tgagagaaat catagaattt taaggccatg atttaaggcc      3513 atcatggcct aagcttgaaa ggagatagga tcaaagcttg gcgtaatcat ggtcatagct      3573 gtttcctgtg tgaaattgtt atccgctcac aattccacac aacatacgag ccggaagcat      3633 aaagtgtaaa gcctggggtg cctaatgagt gagctaactc acattaattg cgttgcgctc      3693 actgcccgct ttccagtcgg gaaacctgtc gtgccagctg cattaatgaa tcggccaacg      3753 cgcggggaga ggcggtttgc gtattgggcg ctcttccgct tcctcgctca ctgactcgct      3813 gcgctcggtc gttcggctgc ggcgagcggt atcagctcac tcaaaggcgg taatacggtt      3873
```

```
atccacagaa tcagggata  acgcaggaaa gaacatgtga gcaaaaggcc agcaaaaggc  3933
caggaaccgt aaaaaggccg cgttgctggc gttttttccat aggctccgcc ccctgacga   3993
gcatcacaaa aatcgacgct caagtcagag gtggcgaaac ccgacaggac tataaagata  4053
ccaggcgttt cccctggaa  gctccctcgt gcgctctcct gttccgaccc tgccgcttac  4113
cggatacctg tccgcctttc tcccttcggg aagcgtggcg ctttctcata gctcacgctg  4173
taggtatctc agttcggtgt aggtcgttcg ctccaagctg gctgtgtgc  acgaaccccc  4233
cgttcagccc gaccgctgcg ccttatccgg taactatcgt cttgagtcca acccggtaag  4293
acacgactta tcgccactgg cagcagccac tggtaacagg attagcagag cgaggtatgt  4353
aggcggtgct acagagttct tgaagtggtg gcctaactac ggctacacta agaacagt    4413
atttggtatc tgcgctctgc tgaagccagt taccttcgga aaagagttg  gtagctcttg  4473
atccggcaaa caaccaccg  ctggtagcgg tggttttttt gtttgcaagc agcagattac  4533
gcgcagaaaa aaaggatctc aagaagatcc tttgatcttt tctacggggt ctgacgctca  4593
gtggaacgaa aactcacgtt aagggatttt ggtcatgaga ttatcaaaaa ggatcttcac  4653
ctagatcctt ttaaattaaa aatgaagttt taaatcaatc taaagtatat atgagtaaac  4713
ttggtctgac agttaccaat gcttaatcag tgaggcacct atctcagcga tctgtctatt  4773
tcgttcatcc atagttgcct gactccccgt cgtgtagata actacgatac gggagggctt  4833
accatctggc cccagtgctg caatgatacc gcgagaacca cgctcaccgg ctccagattt  4893
atcagcaata aaccagccag ccggaagggc cgagcgcaga agtggtcctg caactttatc  4953
cgcctccatc cagtctatta ttgttgccg  ggaagctaga gtaagtagtt cgccagttaa  5013
tagtttgcgc aacgttgttg ccattgctac aggcatcgtg gtgtcacgct cgtcgtttgg  5073
tatggcttca ttcagctccg gttcccaacg atcaaggcga gttacatgat cccccatgtt  5133
gtgcaaaaaa gcggttagct ccttcggtcc tccgatcgtt gtcagaagta agttggccgc  5193
agtgttatca ctcatggtta tggcagcact gcataattct cttactgtca tgccatccgt  5253
aagatgcttt tctgtgactg gtgagtactc aaccaagtca ttctgagaat agtgtatgcg  5313
gcgaccgagt tgctcttgcc cggcgtcaat acgggataat accgcgccac atagcagaac  5373
tttaaaagtg ctcatcattg gaaaacgttc ttcggggcga aaactctcaa ggatcttacc  5433
gctgttgaga tccagttcga tgtaacccac tcgtgcaccc aactgatctt cagcatcttt  5493
tactttcacc agcgtttctg ggtgagcaaa aacaggaagg caaaatgccg caaaaaaggg  5553
aataagggcg acacggaaat gttgaatact catactcttc cttttcaat  attattgaag  5613
catttatcag ggttattgtc tcatgagcgg atacatattt gaatgtattt agaaaaataa  5673
acaaataggg gttccgcgca catttccccg aaaagtgcca cctgacgtct aagaaaccat  5733
tattatcatg acattaacct ataaaaatag gcgtatcacg aggcccttc  gggtcgcgcg  5793
tttcggtgat gacggtgaaa acctctgaca catgcagctc ccgttgacgg tcacagcttg  5853
tctgtaagcg gatgccggga gcagacaagc ccgtcagggc gcgtcagcgg tgttggcgg   5913
gtgtcgggc  tggcttaact atgcggcatc agagcagatt gtactgagag tgcaccataa  5973
aattgtaaac gttaatattt tgttaaaatt cgcgttaaat ttttgttaaa tcagctcatt  6033
ttttaaccaa taggccgaaa tcggcaaaat cccttataaa tcaaaagaat agcccgagat  6093
agggttgagt gttgttccag tttggaacaa gagtccacta ttaaagaacg tggactccaa  6153
cgtcaaaggg cgaaaaaccg tctatcaggg cgatggccca ctacgtgaac catcacccaa  6213
atcaagtttt ttggggtcga ggtgccgtaa agcactaaat cggaacccta agggagccc   6273
```

-continued

```
ccgatttaga gcttgacggg gaaagccggc gaacgtggcg agaaaggaag ggaagaaagc    6333
gaaaggagcg ggcgctaggg cgctggcaag tgtagcggtc acgctgcgcg taaccaccac    6393
acccgccgcg cttaatgcgc cgctacaggg cgcgtactat ggttgctttg acgtatgcgg    6453
tgtgaaatac cgcacagatg cgtaaggaga aataccgca tcaggcgcca ttcgccattc     6513
aggctgcgca actgttggga agggcgatcg gtgcgggcct cttcgctatt acgccagctg    6573
gcgaaagggg gatgtgctgc aaggcgatta agttgggtaa cgccagggtt ttcccagtca    6633
cgacgttgta aaacgacggc cagtgaattc catggtctca actttc                   6679
```

<210> SEQ ID NO 8
<211> LENGTH: 676
<212> TYPE: PRT
<213> ORGANISM: Dengue virus

<400> SEQUENCE: 8

```
Met Thr Ala Gly Met Ile Ile Met Leu Ile Pro Thr Val Met Ala Phe
 1               5                  10                  15

His Leu Thr Thr Arg Asn Gly Glu Pro His Met Ile Val Ser Arg Gln
             20                  25                  30

Glu Lys Gly Lys Ser Leu Leu Phe Lys Thr Lys Asp Gly Thr Asn Met
         35                  40                  45

Cys Thr Leu Met Ala Met Asp Leu Gly Glu Leu Cys Glu Asp Thr Ile
     50                  55                  60

Thr Tyr Lys Cys Pro Phe Leu Lys Gln Asn Glu Pro Glu Asp Ile Asp
 65                  70                  75                  80

Cys Trp Cys Asn Ser Thr Ser Thr Trp Val Thr Tyr Gly Thr Cys Thr
                 85                  90                  95

Thr Thr Gly Glu His Arg Arg Glu Lys Arg Ser Val Ala Leu Val Pro
            100                 105                 110

His Val Gly Met Gly Leu Glu Thr Arg Thr Glu Thr Trp Met Ser Ser
        115                 120                 125

Glu Gly Ala Trp Lys His Ala Gln Arg Ile Glu Thr Trp Ile Leu Arg
    130                 135                 140

His Pro Gly Phe Thr Ile Met Ala Ala Ile Leu Ala Tyr Thr Ile Gly
145                 150                 155                 160

Thr Thr His Phe Gln Arg Val Leu Ile Phe Ile Leu Leu Thr Ala Ile
                165                 170                 175

Ala Pro Ser Met Thr Met Arg Cys Ile Gly Ile Ser Asn Arg Asp Phe
            180                 185                 190

Val Glu Gly Val Ser Gly Gly Ser Trp Val Asp Ile Val Leu Glu His
        195                 200                 205

Gly Ser Cys Val Thr Thr Met Ala Lys Asn Lys Pro Thr Leu Asp Phe
    210                 215                 220

Glu Leu Ile Lys Thr Glu Ala Lys Gln Pro Ala Thr Leu Arg Lys Tyr
225                 230                 235                 240

Cys Ile Glu Ala Lys Leu Thr Asn Thr Thr Thr Asp Ser Arg Cys Pro
                245                 250                 255

Thr Gln Gly Glu Pro Thr Leu Asn Glu Glu Gln Asp Lys Arg Phe Val
            260                 265                 270

Cys Lys His Ser Met Val Asp Arg Gly Trp Gly Asn Gly Cys Gly Leu
        275                 280                 285

Phe Gly Lys Gly Gly Ile Val Thr Cys Ala Met Phe Thr Cys Lys Lys
    290                 295                 300
```

Asn Met Glu Gly Lys Ile Val Gln Pro Glu Asn Leu Glu Tyr Thr Val
305                 310                 315                 320

Val Ile Thr Pro His Ser Gly Glu Glu His Ala Val Gly Asn Asp Thr
            325                 330                 335

Gly Lys His Gly Lys Glu Val Lys Ile Thr Pro Gln Ser Ser Ile Thr
            340                 345                 350

Glu Ala Glu Leu Thr Gly Tyr Gly Thr Val Thr Met Glu Cys Ser Pro
            355                 360                 365

Arg Thr Gly Leu Asp Phe Asn Glu Met Val Leu Leu Gln Met Lys Asp
    370                 375                 380

Lys Ala Trp Leu Val His Arg Gln Trp Phe Leu Asp Leu Pro Leu Pro
385                 390                 395                 400

Trp Leu Pro Gly Ala Asp Thr Gln Gly Ser Asn Trp Ile Gln Lys Glu
            405                 410                 415

Thr Leu Val Thr Phe Lys Asn Pro His Ala Lys Lys Gln Asp Val Val
            420                 425                 430

Val Leu Gly Ser Gln Glu Gly Ala Met His Thr Ala Leu Thr Gly Ala
            435                 440                 445

Thr Glu Ile Gln Met Ser Ser Gly Asn Leu Leu Phe Thr Gly His Leu
450                 455                 460

Lys Cys Arg Leu Arg Met Asp Lys Leu Gln Leu Lys Gly Met Ser Tyr
465                 470                 475                 480

Val Met Cys Thr Gly Ser Phe Lys Leu Glu Lys Glu Val Ala Glu Thr
            485                 490                 495

Gln His Gly Thr Val Leu Val Gln Val Lys Tyr Glu Gly Thr Asp Ala
            500                 505                 510

Pro Cys Lys Ile Pro Phe Ser Ser Gln Asp Glu Lys Gly Val Thr Gln
            515                 520                 525

Asn Gly Arg Leu Ile Thr Ala Asn Pro Ile Val Thr Asp Lys Glu Lys
530                 535                 540

Pro Val Asn Ile Glu Ala Glu Pro Pro Phe Gly Glu Ser Tyr Ile Val
545                 550                 555                 560

Val Gly Ala Gly Glu Lys Ala Leu Lys Leu Ser Trp Phe Lys Lys Gly
            565                 570                 575

Ser Ser Ile Gly Lys Met Phe Glu Ala Thr Ala Arg Gly Ala Arg Arg
            580                 585                 590

Met Ala Ile Leu Gly Asp Thr Ala Trp Asp Phe Gly Ser Ile Gly Gly
            595                 600                 605

Val Phe Thr Ser Val Gly Lys Leu Ile His Gln Ile Phe Gly Thr Ala
            610                 615                 620

Tyr Gly Val Leu Phe Ser Gly Val Ser Trp Thr Met Lys Ile Gly Ile
625                 630                 635                 640

Gly Ile Leu Leu Thr Trp Leu Gly Leu Asn Ser Arg Ser Thr Ser Leu
            645                 650                 655

Ser Met Thr Cys Ile Ala Val Gly Met Val Thr Leu Tyr Leu Gly Val
            660                 665                 670

Met Val Gln Ala
        675

<210> SEQ ID NO 9
<211> LENGTH: 6679
<212> TYPE: DNA
<213> ORGANISM: Dengue virus
<220> FEATURE:

-continued

<221> NAME/KEY: misc_feature
<223> OTHER INFORMATION: Chimera DENV2 prM E (Env F108A)_chimeric DENV1
      E
<220> FEATURE:
<221> NAME/KEY: CDS
<222> LOCATION: (906)..(2933)
<220> FEATURE:
<221> NAME/KEY: misc_feature
<222> LOCATION: (906)..(2336)
<223> OTHER INFORMATION: DENV2 prM E region
<220> FEATURE:
<221> NAME/KEY: misc_feature
<222> LOCATION: (2337)..(2933)
<223> OTHER INFORMATION: DENV1 region (F108A)

<400> SEQUENCE: 9

```
gaattcccat tgcatacgtt gtatccatat cataatatgt acatttatat tggctcatgt      60
ccaacattac cgccatgttg acattgatta ttgactagtt attaatagta atcaattacg     120
gggtcattag ttcatagccc atatatggag ttccgcgtta cataacttac ggtaaatggc     180
ccgcctggct gaccgcccaa cgaccccgc ccattgacgt caataatgac gtatgttccc      240
atagtaacgc caatagggac tttccattga cgtcaatggg tggagtattt acggtaaact     300
gcccacttgg cagtacatca agtgtatcat atgccaagta cgccccctat tgacgtcaat     360
gacggtaaat ggcccgcctg gcattatgcc cagtacatga ccttatggga ctttcctact     420
tggcagtaca tctacgtatt agtcatcgct attaccatgg tgatgcggtt ttggcagtac     480
atcaatgggc gtggatagcg gtttgactca cggggatttc caagtctcca ccccattgac     540
gtcaatggga gtttgttttg gcaccaaaat caacgggact ttccaaaatg tcgtaacaac     600
tccgccccat tgacgcaaat gggcggtagg cgtgtacggt gggaggtcta tataagcaga     660
gctcgtttag tgaaccgtca gatcgcctgg agacgccatc cacgctgttt tgacctccat     720
agaagacacc gggaccgatc cagcctccgt taacggtgga gggcagtgta gtctgagcag     780
tactcgttgc tgccgcgcgc gccaccagac ataaatagctg acagactaac agactgttcc     840
tttccatggg tcttttctgc agtcaccgtc gtcgacacgt gtgatcagat atcgcggccg     900 ccacc atg act gca ggc atg atc atc atg ctg att cca aca gtg atg gcg     950
      Met Thr Ala Gly Met Ile Ile Met Leu Ile Pro Thr Val Met Ala
      1               5                  10                 15 ttt cat ctg acc aca cgc aac gga gaa cca cac atg atc gtc agt aga       998
Phe His Leu Thr Thr Arg Asn Gly Glu Pro His Met Ile Val Ser Arg
             20                  25                  30 caa gaa aaa ggg aaa agc ctt ctg ttt aag aca aag gac ggc acg aac      1046
Gln Glu Lys Gly Lys Ser Leu Leu Phe Lys Thr Lys Asp Gly Thr Asn
         35                  40                  45 atg tgt acc ctc atg gcc atg gac ctt ggt gag ttg tgt gaa gac aca      1094
Met Cys Thr Leu Met Ala Met Asp Leu Gly Glu Leu Cys Glu Asp Thr
     50                  55                  60 atc acg tat aaa tgt ccc ttt ctc aag cag aac gaa cca gaa gac ata      1142
Ile Thr Tyr Lys Cys Pro Phe Leu Lys Gln Asn Glu Pro Glu Asp Ile
 65                  70                  75 gat tgt tgg tgc aac tcc acg tcc aca tgg gta act tat ggg aca tgt      1190
Asp Cys Trp Cys Asn Ser Thr Ser Thr Trp Val Thr Tyr Gly Thr Cys
 80                  85                  90                  95 acc acc aca gga gag cac aga aga gaa aaa aga tca gtg gcg ctt gtt      1238
Thr Thr Thr Gly Glu His Arg Arg Glu Lys Arg Ser Val Ala Leu Val
                100                 105                 110 cca cac gtg gga atg gga ttg gag aca cga act gaa aca tgg atg tca      1286
Pro His Val Gly Met Gly Leu Glu Thr Arg Thr Glu Thr Trp Met Ser
            115                 120                 125
```

|   |   |   |   |   |   |   |   |   |   |   |   |   |   |   |   |   |
|---|---|---|---|---|---|---|---|---|---|---|---|---|---|---|---|---|
| tca | gaa | ggg | gcc | tgg | aaa | cat | gcc | cag | aga | att | gaa | act | tgg | att | ctg | 1334 |
| Ser | Glu | Gly | Ala | Trp | Lys | His | Ala | Gln | Arg | Ile | Glu | Thr | Trp | Ile | Leu |   |
|   |   | 130 |   |   |   |   | 135 |   |   |   |   | 140 |   |   |   |   |
| aga | cat | cca | ggc | ttt | acc | ata | atg | gcc | gca | atc | ctg | gca | tac | acc | ata | 1382 |
| Arg | His | Pro | Gly | Phe | Thr | Ile | Met | Ala | Ala | Ile | Leu | Ala | Tyr | Thr | Ile |   |
|   | 145 |   |   |   |   | 150 |   |   |   |   | 155 |   |   |   |   |   |
| gga | acg | acg | cat | ttc | caa | aga | gtc | ctg | ata | ttc | atc | cta | ctg | aca | gcc | 1430 |
| Gly | Thr | Thr | His | Phe | Gln | Arg | Val | Leu | Ile | Phe | Ile | Leu | Leu | Thr | Ala |   |
| 160 |   |   |   |   | 165 |   |   |   |   | 170 |   |   |   |   | 175 |   |
| atc | gct | cct | tca | atg | aca | atg | cgc | tgc | ata | gga | ata | tca | aat | agg | gac | 1478 |
| Ile | Ala | Pro | Ser | Met | Thr | Met | Arg | Cys | Ile | Gly | Ile | Ser | Asn | Arg | Asp |   |
|   |   |   |   | 180 |   |   |   |   | 185 |   |   |   |   | 190 |   |   |
| ttt | gtg | gaa | gga | gtg | tca | gga | ggg | agt | tgg | gtt | gac | ata | gtt | tta | gaa | 1526 |
| Phe | Val | Glu | Gly | Val | Ser | Gly | Gly | Ser | Trp | Val | Asp | Ile | Val | Leu | Glu |   |
|   |   |   | 195 |   |   |   |   | 200 |   |   |   |   | 205 |   |   |   |
| cat | gga | agt | tgt | gtg | acg | acg | atg | gca | aaa | aat | aaa | cca | aca | ctg | gac | 1574 |
| His | Gly | Ser | Cys | Val | Thr | Thr | Met | Ala | Lys | Asn | Lys | Pro | Thr | Leu | Asp |   |
|   |   | 210 |   |   |   |   | 215 |   |   |   |   | 220 |   |   |   |   |
| ttt | gaa | ctg | ata | aaa | aca | gaa | gcc | aaa | caa | ccc | gcc | acc | tta | agg | aag | 1622 |
| Phe | Glu | Leu | Ile | Lys | Thr | Glu | Ala | Lys | Gln | Pro | Ala | Thr | Leu | Arg | Lys |   |
|   | 225 |   |   |   |   | 230 |   |   |   |   | 235 |   |   |   |   |   |
| tac | tgt | ata | gag | gct | aaa | ctg | acc | aac | acg | aca | aca | gac | tcg | cgc | tgc | 1670 |
| Tyr | Cys | Ile | Glu | Ala | Lys | Leu | Thr | Asn | Thr | Thr | Thr | Asp | Ser | Arg | Cys |   |
| 240 |   |   |   |   | 245 |   |   |   |   | 250 |   |   |   |   | 255 |   |
| cca | aca | caa | ggg | gaa | ccc | acc | ctg | aat | gaa | gag | cag | gac | aaa | agg | ttt | 1718 |
| Pro | Thr | Gln | Gly | Glu | Pro | Thr | Leu | Asn | Glu | Glu | Gln | Asp | Lys | Arg | Phe |   |
|   |   |   |   | 260 |   |   |   |   | 265 |   |   |   |   | 270 |   |   |
| gtc | tgc | aaa | cat | tcc | atg | gta | gac | aga | gga | tgg | gga | aat | gga | tgt | gga | 1766 |
| Val | Cys | Lys | His | Ser | Met | Val | Asp | Arg | Gly | Trp | Gly | Asn | Gly | Cys | Gly |   |
|   |   |   | 275 |   |   |   |   | 280 |   |   |   |   | 285 |   |   |   |
| tta | gct | gga | aaa | gga | ggc | atc | gtg | acc | tgt | gcc | atg | ttc | aca | tgc | aaa | 1814 |
| Leu | Ala | Gly | Lys | Gly | Gly | Ile | Val | Thr | Cys | Ala | Met | Phe | Thr | Cys | Lys |   |
|   |   | 290 |   |   |   |   | 295 |   |   |   |   | 300 |   |   |   |   |
| aag | aac | atg | gag | gga | aaa | att | gtg | cag | cca | gaa | aac | ctg | gaa | tac | act | 1862 |
| Lys | Asn | Met | Glu | Gly | Lys | Ile | Val | Gln | Pro | Glu | Asn | Leu | Glu | Tyr | Thr |   |
|   | 305 |   |   |   |   | 310 |   |   |   |   | 315 |   |   |   |   |   |
| gtc | gtt | ata | aca | cct | cat | tca | ggg | gaa | gaa | cat | gca | gtc | gga | aat | gac | 1910 |
| Val | Val | Ile | Thr | Pro | His | Ser | Gly | Glu | Glu | His | Ala | Val | Gly | Asn | Asp |   |
| 320 |   |   |   |   | 325 |   |   |   |   | 330 |   |   |   |   | 335 |   |
| aca | gga | aaa | cat | ggt | aaa | gaa | gtc | aag | ata | aca | cca | cag | agc | tcc | atc | 1958 |
| Thr | Gly | Lys | His | Gly | Lys | Glu | Val | Lys | Ile | Thr | Pro | Gln | Ser | Ser | Ile |   |
|   |   |   |   | 340 |   |   |   |   | 345 |   |   |   |   | 350 |   |   |
| aca | gag | gcg | gaa | ctg | aca | ggc | tat | ggc | act | gtt | acg | atg | gag | tgc | tct | 2006 |
| Thr | Glu | Ala | Glu | Leu | Thr | Gly | Tyr | Gly | Thr | Val | Thr | Met | Glu | Cys | Ser |   |
|   |   | 355 |   |   |   |   | 360 |   |   |   |   | 365 |   |   |   |   |
| cca | aga | acg | ggc | ctc | gac | ttc | aat | gag | atg | gtg | ttg | ctg | caa | atg | aaa | 2054 |
| Pro | Arg | Thr | Gly | Leu | Asp | Phe | Asn | Glu | Met | Val | Leu | Leu | Gln | Met | Lys |   |
|   | 370 |   |   |   |   | 375 |   |   |   |   | 380 |   |   |   |   |   |
| gac | aaa | gct | tgg | ctg | gtg | cac | aga | caa | tgg | ttc | cta | gac | cta | ccg | ttg | 2102 |
| Asp | Lys | Ala | Trp | Leu | Val | His | Arg | Gln | Trp | Phe | Leu | Asp | Leu | Pro | Leu |   |
| 385 |   |   |   |   | 390 |   |   |   |   | 395 |   |   |   |   |   |   |
| cca | tgg | ctg | ccc | gga | gca | gac | aca | caa | gga | tca | aat | tgg | ata | cag | aaa | 2150 |
| Pro | Trp | Leu | Pro | Gly | Ala | Asp | Thr | Gln | Gly | Ser | Asn | Trp | Ile | Gln | Lys |   |
| 400 |   |   |   |   | 405 |   |   |   |   | 410 |   |   |   |   | 415 |   |
| gag | aca | ctg | gtc | acc | ttc | aaa | aat | ccc | cat | gcg | aaa | aaa | cag | gat | gtt | 2198 |
| Glu | Thr | Leu | Val | Thr | Phe | Lys | Asn | Pro | His | Ala | Lys | Lys | Gln | Asp | Val |   |
|   |   |   |   | 420 |   |   |   |   | 425 |   |   |   |   | 430 |   |   |
| gtt | gtc | tta | ggc | tcc | caa | gag | ggg | gcc | atg | cat | aca | gca | ctc | aca | ggg | 2246 |
| Val | Val | Leu | Gly | Ser | Gln | Glu | Gly | Ala | Met | His | Thr | Ala | Leu | Thr | Gly |   |
|   |   |   | 435 |   |   |   |   | 440 |   |   |   |   | 445 |   |   |   |

| | | |
|---|---|---|
| gct acg gaa atc cag atg tca tca gga aac ctg ctg ttc aca gga cat<br>Ala Thr Glu Ile Gln Met Ser Ser Gly Asn Leu Leu Phe Thr Gly His<br>450 455 460 | | 2294 |
| ctt aag tgc agg ctg aga atg gac aaa tta caa ctt aaa ggg atg tca<br>Leu Lys Cys Arg Leu Arg Met Asp Lys Leu Gln Leu Lys Gly Met Ser<br>465 470 475 | | 2342 |
| tat gta atg tgc aca ggg tca ttc aag tta gag aag gaa gtg gct gag<br>Tyr Val Met Cys Thr Gly Ser Phe Lys Leu Glu Lys Glu Val Ala Glu<br>480 485 490 495 | | 2390 |
| acc cag cat gga act gtt cta gtg cag gtt aaa tac gaa gga aca gat<br>Thr Gln His Gly Thr Val Leu Val Gln Val Lys Tyr Glu Gly Thr Asp<br>500 505 510 | | 2438 |
| gca cca tgc aag atc ccc ttc tcg tcc caa gat gag aag gga gta acc<br>Ala Pro Cys Lys Ile Pro Phe Ser Ser Gln Asp Glu Lys Gly Val Thr<br>515 520 525 | | 2486 |
| cag aat ggg aga ttg ata aca gcc aac ccc ata gtc act gac aaa gaa<br>Gln Asn Gly Arg Leu Ile Thr Ala Asn Pro Ile Val Thr Asp Lys Glu<br>530 535 540 | | 2534 |
| aaa cca gtc aac att gaa gcg gag cca cct ttt ggt gag agc tac att<br>Lys Pro Val Asn Ile Glu Ala Glu Pro Pro Phe Gly Glu Ser Tyr Ile<br>545 550 555 | | 2582 |
| gtg gta gga gca ggt gaa aaa gct ttg aaa cta agc tgg ttc aag aag<br>Val Val Gly Ala Gly Glu Lys Ala Leu Lys Leu Ser Trp Phe Lys Lys<br>560 565 570 575 | | 2630 |
| gga agc agt ata ggg aaa atg ttt gaa gca act gcc cgt gga gca cga<br>Gly Ser Ser Ile Gly Lys Met Phe Glu Ala Thr Ala Arg Gly Ala Arg<br>580 585 590 | | 2678 |
| agg atg gcc atc ctg gga gac act gca tgg gac ttc ggt tct ata gga<br>Arg Met Ala Ile Leu Gly Asp Thr Ala Trp Asp Phe Gly Ser Ile Gly<br>595 600 605 | | 2726 |
| ggg gtg ttc acg tct gtg gga aaa ctg ata cac cag att ttt ggg act<br>Gly Val Phe Thr Ser Val Gly Lys Leu Ile His Gln Ile Phe Gly Thr<br>610 615 620 | | 2774 |
| gcg tat gga gtt ttg ttc agc ggt gtt tct tgg acc atg aag ata gga<br>Ala Tyr Gly Val Leu Phe Ser Gly Val Ser Trp Thr Met Lys Ile Gly<br>625 630 635 | | 2822 |
| ata ggg att ctg ctg aca tgg cta gga tta aac tca agg agc acg tcc<br>Ile Gly Ile Leu Leu Thr Trp Leu Gly Leu Asn Ser Arg Ser Thr Ser<br>640 645 650 655 | | 2870 |
| ctt tca atg acg tgt atc gca gtt ggc atg gtc acg ctg tac cta gga<br>Leu Ser Met Thr Cys Ile Ala Val Gly Met Val Thr Leu Tyr Leu Gly<br>660 665 670 | | 2918 |
| gtc atg gtt cag gcg taataaagat ctgctgtgcc ttctagttgc cagccatctg<br>Val Met Val Gln Ala<br>675 | | 2973 |
| ttgtttgccc ctcccccgtg ccttccttga ccctggaagg tgccactccc actgtccttt | | 3033 |
| cctaataaaa tgaggaaatt gcatcgcatt gtctgagtag gtgtcattct attctggggg | | 3093 |
| gtggggtggg gcaggacagc aaggggagg attgggaaga caatagcagg catgctgggg | | 3153 |
| atgcggtggg ctctatgggt acccaggtgc tgaagaattg acccggttcc tcctgggcca | | 3213 |
| gaaagaagca ggcacatccc cttctctgtg acacaccctg tccacgcccc tggttcttag | | 3273 |
| ttccagcccc actcatagga cactcatagc tcaggagggc tccgcttca atcccacccg | | 3333 |
| ctaaagtact tggagcggtc tctccctccc tcatcagccc accaaaccaa acctagcctc | | 3393 |
| caagagtggg aagaaattaa agcaagatag gctattaagt gcagggggag agaaaatgcc | | 3453 |
| tccaacatgt gaggaagtaa tgagagaaat catagaattt taaggccatg atttaaggcc | | 3513 |

```
atcatggcct aagcttgaaa ggagatagga tcaaagcttg gcgtaatcat ggtcatagct      3573
gtttcctgtg tgaaattgtt atccgctcac aattccacac aacatacgag ccggaagcat      3633
aaagtgtaaa gcctggggtg cctaatgagt gagctaactc acattaattg cgttgcgctc      3693
actgcccgct ttccagtcgg gaaacctgtc gtgccagctg cattaatgaa tcggccaacg      3753
cgcggggaga ggcggtttgc gtattgggcg ctcttccgct tcctcgctca ctgactcgct      3813
gcgctcggtc gttcggctgc ggcgagcggt atcagctcac tcaaaggcgg taatacggtt      3873
atccacagaa tcaggggata acgcaggaaa gaacatgtga gcaaaaggcc agcaaaaggc      3933
caggaaccgt aaaaaggccg cgttgctggc gtttttccat aggctccgcc ccctgacga      3993
gcatcacaaa aatcgacgct caagtcagag gtggcgaaac ccgacaggac tataaagata      4053
ccaggcgttt ccccctggaa gctccctcgt gcgctctcct gttccgaccc tgccgcttac      4113
cggatacctg tccgcctttc tcccttcggg aagcgtggcg ctttctcata gctcacgctg      4173
taggtatctc agttcggtgt aggtcgttcg ctccaagctg ggctgtgtgc acgaaccccc      4233
cgttcagccc gaccgctgcg ccttatccgg taactatcgt cttgagtcca acccggtaag      4293
acacgactta tcgccactgg cagcagccac tggtaacagg attagcagag cgaggtatgt      4353
aggcggtgct acagagttct tgaagtggtg gcctaactac ggctacacta agaacagt       4413
atttggtatc tgcgctctgc tgaagccagt taccttcgga aaaagagttg gtagctcttg      4473
atccggcaaa caaccaccg ctggtagcgg tggtttttt gtttgcaagc agcagattac        4533
gcgcagaaaa aaaggatctc aagaagatcc tttgatcttt tctacggggt ctgacgctca      4593
gtggaacgaa aactcacgtt aagggatttt ggtcatgaga ttatcaaaaa ggatcttcac      4653
ctagatcctt ttaaattaaa aatgaagttt taaatcaatc taagtatat atgagtaaac       4713
ttggtctgac agttaccaat gcttaatcag tgaggcacct atctcagcga tctgtctatt      4773
tcgttcatcc atagttgcct gactccccgt cgtgtagata actacgatac gggagggctt      4833
accatctggc cccagtgctg caatgatacc gcgagaacca cgctcaccgg ctccagattt      4893
atcagcaata aaccagccag ccggaagggc cgagcgcaga agtggtcctg caactttatc      4953
cgcctccatc cagtctatta attgttgccg ggaagctaga gtaagtagtt cgccagttaa      5013
tagtttcgc aacgttgttg ccattgctac aggcatcgtg gtgtcacgct cgtcgtttgg       5073
tatggcttca ttcagctccg gttcccaacg atcaaggcga gttacatgat cccccatgtt      5133
gtgcaaaaaa gcggttagct ccttcggtcc tccgatcgtt gtcagaagta agttggccgc      5193
agtgttatca ctcatggtta tggcagcact gcataattct cttactgtca tgccatccgt      5253
aagatgcttt tctgtgactg gtgagtactc aaccaagtca ttctgagaat agtgtatgcg      5313
gcgaccgagt tgctcttgcc cggcgtcaat acgggataat accgcgccac atagcagaac      5373
tttaaaagtg ctcatcattg gaaaacgttc ttcggggcga aaactctcaa ggatcttacc      5433
gctgttgaga tccagttcga tgtaacccac tcgtgcaccc aactgatctt cagcatcttt      5493
tactttcacc agcgtttctg ggtgagcaaa aacaggaagg caaaatgccg caaaaaggg      5553
aataagggcg acacggaaat gttgaatact catactcttc ctttttcaat attattgaag     5613
catttatcag ggttattgtc tcatgagcgg atacatattt gaatgtattt agaaaaataa     5673
acaaataggg gttccgcgca catttccccg aaaagtgcca cctgacgtct aagaaaccat     5733
tattatcatg acattaacct ataaaaatag gcgtatcacg aggccctttc gggtcgcgcg     5793
tttcggtgat gacggtgaaa acctctgaca catgcagctc ccgttgacgg tcacagcttg     5853
tctgtaagcg gatgccggga gcagacaagc ccgtcagggc gcgtcagcgg gtgttggcgg     5913
```

```
gtgtcggggc tggcttaact atgcggcatc agagcagatt gtactgagag tgcaccataa  5973
aattgtaaac gttaatattt tgttaaaatt cgcgttaaat ttttgttaaa tcagctcatt  6033
ttttaaccaa taggccgaaa tcggcaaaat cccttataaa tcaaaagaat agcccgagat  6093
agggttgagt gttgttccag tttgaacaa gagtccacta ttaaagaacg tggactccaa  6153
cgtcaaaggg cgaaaaaccg tctatcaggg cgatggccca ctacgtgaac catcacccaa  6213
atcaagtttt tgggggtcga ggtgccgtaa agcactaaat cggaacccta aagggagccc  6273
ccgatttaga gcttgacggg gaaagccggc gaacgtggcg agaaaggaag ggaagaaagc  6333
gaaaggagcg ggcgctaggg cgctggcaag tgtagcggtc acgctgcgcg taaccaccac  6393
acccgccgcg cttaatgcgc cgctacaggg cgcgtactat ggttgctttg acgtatgcgg  6453
tgtgaaatac cgcacagatg cgtaaggaga aataccgca tcaggcgcca ttcgccattc  6513
aggctgcgca actgttggga agggcgatcg gtgcgggcct cttcgctatt acgccagctg  6573
gcgaaagggg gatgtgctgc aaggcgatta agttgggtaa cgccagggtt ttcccagtca  6633
cgacgttgta aaacgacggc cagtgaattc catggtctca actttc       6679
```

<210> SEQ ID NO 10
<211> LENGTH: 676
<212> TYPE: PRT
<213> ORGANISM: Dengue virus

<400> SEQUENCE: 10

```
Met Thr Ala Gly Met Ile Ile Met Leu Ile Pro Thr Val Met Ala Phe
1               5                   10                  15

His Leu Thr Thr Arg Asn Gly Glu Pro His Met Ile Val Ser Arg Gln
            20                  25                  30

Glu Lys Gly Lys Ser Leu Leu Phe Lys Thr Lys Asp Gly Thr Asn Met
        35                  40                  45

Cys Thr Leu Met Ala Met Asp Leu Gly Glu Leu Cys Glu Asp Thr Ile
    50                  55                  60

Thr Tyr Lys Cys Pro Phe Leu Lys Gln Asn Glu Pro Glu Asp Ile Asp
65                  70                  75                  80

Cys Trp Cys Asn Ser Thr Ser Thr Trp Val Thr Tyr Gly Thr Cys Thr
                85                  90                  95

Thr Thr Gly Glu His Arg Arg Glu Lys Arg Ser Val Ala Leu Val Pro
            100                 105                 110

His Val Gly Met Gly Leu Glu Thr Arg Thr Glu Thr Trp Met Ser Ser
        115                 120                 125

Glu Gly Ala Trp Lys His Ala Gln Arg Ile Glu Thr Trp Ile Leu Arg
    130                 135                 140

His Pro Gly Phe Thr Ile Met Ala Ala Ile Leu Ala Tyr Thr Ile Gly
145                 150                 155                 160

Thr Thr His Phe Gln Arg Val Leu Ile Phe Ile Leu Leu Thr Ala Ile
                165                 170                 175

Ala Pro Ser Met Thr Met Arg Cys Ile Gly Ile Ser Asn Arg Asp Phe
            180                 185                 190

Val Glu Gly Val Ser Gly Gly Ser Trp Val Asp Ile Val Leu Glu His
        195                 200                 205

Gly Ser Cys Val Thr Thr Met Ala Lys Asn Lys Pro Thr Leu Asp Phe
    210                 215                 220

Glu Leu Ile Lys Thr Glu Ala Lys Gln Pro Ala Thr Leu Arg Lys Tyr
225                 230                 235                 240
```

```
            Cys Ile Glu Ala Lys Leu Thr Asn Thr Thr Thr Asp Ser Arg Cys Pro
                        245                 250                 255

Thr Gln Gly Glu Pro Thr Leu Asn Glu Gln Asp Lys Arg Phe Val
                        260                 265                 270

Cys Lys His Ser Met Val Asp Arg Gly Trp Gly Asn Gly Cys Gly Leu
                        275                 280                 285

Ala Gly Lys Gly Gly Ile Val Thr Cys Ala Met Phe Thr Cys Lys Lys
                        290                 295                 300

Asn Met Glu Gly Lys Ile Val Gln Pro Glu Asn Leu Glu Tyr Thr Val
            305                 310                 315                 320

Val Ile Thr Pro His Ser Gly Glu His Ala Val Gly Asn Asp Thr
                            325                 330                 335

Gly Lys His Gly Lys Glu Val Lys Ile Thr Pro Gln Ser Ser Ile Thr
                        340                 345                 350

Glu Ala Glu Leu Thr Gly Tyr Gly Thr Val Thr Met Glu Cys Ser Pro
                        355                 360                 365

Arg Thr Gly Leu Asp Phe Asn Glu Met Val Leu Leu Gln Met Lys Asp
                370                 375                 380

Lys Ala Trp Leu Val His Arg Gln Trp Phe Leu Asp Leu Pro Leu Pro
            385                 390                 395                 400

Trp Leu Pro Gly Ala Asp Thr Gln Gly Ser Asn Trp Ile Gln Lys Glu
                            405                 410                 415

Thr Leu Val Thr Phe Lys Asn Pro His Ala Lys Lys Gln Asp Val Val
                        420                 425                 430

Val Leu Gly Ser Gln Glu Gly Ala Met His Thr Ala Leu Thr Gly Ala
                        435                 440                 445

Thr Glu Ile Gln Met Ser Ser Gly Asn Leu Leu Phe Thr Gly His Leu
                        450                 455                 460

Lys Cys Arg Leu Arg Met Asp Lys Leu Gln Leu Lys Gly Met Ser Tyr
            465                 470                 475                 480

Val Met Cys Thr Gly Ser Phe Lys Leu Glu Lys Glu Val Ala Glu Thr
                            485                 490                 495

Gln His Gly Thr Val Leu Val Gln Val Lys Tyr Glu Gly Thr Asp Ala
                        500                 505                 510

Pro Cys Lys Ile Pro Phe Ser Ser Gln Asp Glu Lys Gly Val Thr Gln
                        515                 520                 525

Asn Gly Arg Leu Ile Thr Ala Asn Pro Ile Val Thr Asp Lys Glu Lys
            530                 535                 540

Pro Val Asn Ile Glu Ala Glu Pro Pro Phe Gly Glu Ser Tyr Ile Val
            545                 550                 555                 560

Val Gly Ala Gly Glu Lys Ala Leu Lys Leu Ser Trp Phe Lys Lys Gly
                            565                 570                 575

Ser Ser Ile Gly Lys Met Phe Glu Ala Thr Ala Arg Gly Ala Arg Arg
                        580                 585                 590

Met Ala Ile Leu Gly Asp Thr Ala Trp Asp Phe Gly Ser Ile Gly Gly
                        595                 600                 605

Val Phe Thr Ser Val Gly Lys Leu Ile His Gln Ile Phe Gly Thr Ala
                        610                 615                 620

Tyr Gly Val Leu Phe Ser Gly Val Ser Trp Thr Met Lys Ile Gly Ile
            625                 630                 635                 640

Gly Ile Leu Leu Thr Trp Leu Gly Leu Asn Ser Arg Ser Thr Ser Leu
                            645                 650                 655
```

Ser Met Thr Cys Ile Ala Val Gly Met Val Thr Leu Tyr Leu Gly Val
            660                 665                 670

Met Val Gln Ala
        675

<210> SEQ ID NO 11
<211> LENGTH: 3770
<212> TYPE: DNA
<213> ORGANISM: Dengue virus
<220> FEATURE:
<221> NAME/KEY: misc_feature
<223> OTHER INFORMATION: DENV2 capsid R85A K86A mutant
<220> FEATURE:
<221> NAME/KEY: CDS
<222> LOCATION: (1046)..(1345)

<400> SEQUENCE: 11

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt gacgcgtttg acattgatta     420
ttgactagtt attaatagta atcaattacg ggtcattag ttcatagccc atatatggag      480
ttccgcgtta cataacttac ggtaaatggc ccgcctggct gaccgcccaa cgaccccgc      540 ccattgacgt caataatgac gtatgttccc atagtaacgc caatagggac tttccattga     600
cgtcaatggg tggagtattt acggtaaact gcccacttgg cagtacatca agtgtatcat     660
atgccaagta cgccccctat tgacgtcaat gacggtaaat ggcccgcctg gcattatgcc     720
cagtacatga cctatgggga ctttcctact tggcagtaca tctacgtatt agtcatcgct     780
attaccatgg tgatgcggtt ttggcagtac atcaatgggc gtggatagcg gtttgactca     840
cggggatttc caagtctcca ccccattgac gtcaatggga gtttgttttg gcaccaaaat     900
caacgggact ttccaaaatg tcgtaacaac tccgccccat tgacgcaaat gggcggtagg     960
cgtgtacggt gggaggtcta taagcaga gctcgtttag tgaaccgtca gataactgca     1020
ggtcgacgat atcgcggccg ccacc atg aat gac caa cgg aaa aag gcg aga     1072
                             Met Asn Asp Gln Arg Lys Lys Ala Arg
                               1               5 aac acg cct ttc aat atg ctg aaa cgc gag aga aac cgc gtg tca act     1120
Asn Thr Pro Phe Asn Met Leu Lys Arg Glu Arg Asn Arg Val Ser Thr
 10              15                  20                  25 gta caa cag ttg aca aag aga ttc tca ctt gga atg ctg cag gga cga     1168
Val Gln Gln Leu Thr Lys Arg Phe Ser Leu Gly Met Leu Gln Gly Arg
                 30                  35                  40 gga cca cta aaa ttg ttc atg gcc ctg gtg gca ttc ctt cgt ttc cta     1216
Gly Pro Leu Lys Leu Phe Met Ala Leu Val Ala Phe Leu Arg Phe Leu
             45                  50                  55 aca atc cca cca aca gca ggg ata tta aaa aga tgg gga aca att aaa     1264
Thr Ile Pro Pro Thr Ala Gly Ile Leu Lys Arg Trp Gly Thr Ile Lys
         60                  65                  70 aaa tca aag gct att aat gtt ctg aga ggc ttc gcg gca gag att gga     1312
Lys Ser Lys Ala Ile Asn Val Leu Arg Gly Phe Ala Ala Glu Ile Gly
     75                  80                  85 agg atg ctg aat atc tta aac agg aga cgt aga taataaagat ctgctgtgcc     1365
Arg Met Leu Asn Ile Leu Asn Arg Arg Arg Arg
```

```
Arg Met Leu Asn Ile Leu Asn Arg Arg Arg Arg
 90              95                  100
```

| | | | | |
|---|---|---|---|---|
| ttctagttgc | cagccatctg | ttgtttgccc | ctccccgtg | ccttccttga | ccctggaagg | 1425 |
| tgccactccc | actgtcctt | cctaataaaa | tgaggaaatt | gcatcgcatt | gtctgagtag | 1485 |
| gtgtcattct | attctggggg | gtggggtggg | gcaggacagc | aagggggagg | attgggaaga | 1545 |
| caatagcagg | catgctgggg | atgcggtggg | ctctatggct | cgagcatggt | catagctgtt | 1605 |
| tcctgtgtga | aattgttatc | cgctcacaat | tccacacaac | atacgagccg | aagcataaa | 1665 |
| gtgtaaagcc | tggggtgcct | aatgagtgag | ctaactcaca | ttaattgcgt | tgcgctcact | 1725 |
| gcccgctttc | cagtcgggaa | acctgtcgtg | ccagctgcat | taatgaatcg | gccaacgcgc | 1785 |
| ggggagaggc | ggtttgcgta | ttgggcgctc | ttccgcttcc | tcgctcactg | actcgctgcg | 1845 |
| ctcggtcgtt | cggctgcggc | gagcggtatc | agctcactca | aaggcggtaa | tacgttatc | 1905 |
| cacagaatca | ggggataacg | caggaaagaa | catgtgagca | aaaggccagc | aaaaggccag | 1965 |
| gaaccgtaaa | aaggccgcgt | tgctggcgtt | tttccatagg | ctccgccccc | ctgacgagca | 2025 |
| tcacaaaaat | cgacgctcaa | gtcagaggtg | gcgaaacccg | acaggactat | aaagatacca | 2085 |
| ggcgtttccc | cctggaagct | ccctcgtgcg | ctctcctgtt | ccgaccctgc | cgcttaccgg | 2145 |
| atacctgtcc | gcctttctcc | cttcgggaag | cgtggcgctt | tctcatagct | cacgctgtag | 2205 |
| gtatctcagt | tcggtgtagg | tcgttcgctc | caagctgggc | tgtgtgcacg | aaccccccgt | 2265 |
| tcagcccgac | cgctgcgcct | tatccggtaa | ctatcgtctt | gagtccaacc | cggtaagaca | 2325 |
| cgacttatcg | ccactggcag | cagccactgg | taacaggatt | agcagagcga | ggtatgtagg | 2385 |
| cggtgctaca | gagttcttga | agtggtggcc | taactacggc | tacactagaa | gaacagtatt | 2445 |
| tggtatctgc | gctctgctga | agccagttac | cttcggaaaa | agagttggta | gctcttgatc | 2505 |
| cggcaaacaa | accaccgctg | gtagcggtgg | tttttttgtt | tgcaagcagc | agattacgcg | 2565 |
| cagaaaaaaa | ggatctcaag | aagatccttt | gatcttttct | acggggtctg | acgctcagtg | 2625 |
| gaacgaaaac | tcacgttaag | ggattttggt | catgagatta | tcaaaaagga | tcttcaccta | 2685 |
| gatccttta | aattaaaaat | gaagttttaa | atcaatctaa | agtatatatg | agtaaacttg | 2745 |
| gtctgacagt | tagaaaaact | catcgagcat | caaatgaaac | tgcaatttat | tcatatcagg | 2805 |
| attatcaata | ccatattttt | gaaaaagccg | tttctgtaat | gaaggagaaa | actcaccgag | 2865 |
| gcagttccat | aggatggcaa | gatcctggta | tcggtctgcg | attccgactc | gtccaacatc | 2925 |
| aatacaacct | attaatttcc | cctcgtcaaa | aataaggtta | tcaagtgaga | aatcaccatg | 2985 |
| agtgacgact | gaatccggtg | agaatggcaa | aagtttatgc | atttctttcc | agacttgttc | 3045 |
| aacaggccag | ccattacgct | cgtcatcaaa | atcactcgca | tcaaccaaac | cgttattcat | 3105 |
| tcgtgattgc | gcctgagcga | gacgaaatac | gcgatcgctg | ttaaaaggac | aattacaaac | 3165 |
| aggaatcgaa | tgcaaccggc | gcaggaacac | tgccagcgca | tcaacaatat | tttcacctga | 3225 |
| atcaggatat | tcttctaata | cctggaatgc | tgttttccca | gggatcgcag | tggtgagtaa | 3285 |
| ccatgcatca | tcaggagtac | ggataaaatg | cttgatggtc | ggaagaggca | taaattccgt | 3345 |
| cagccagttt | agtctgacca | tctcatctgt | aacatcattg | gcaacgctac | ctttgccatg | 3405 |
| tttcagaaac | aactctggcg | catcgggctt | cccatacaat | cgatagattg | tcgcacctga | 3465 |
| ttgcccgaca | ttatcgcgag | cccatttata | cccatataaa | tcagcatcca | tgttggaatt | 3525 |
| taatcgcggc | ctagagcaag | acgtttcccg | ttgaatatgg | ctcatactct | tcctttttca | 3585 |
| atattattga | agcatttatc | agggttattg | tctcatgagc | ggatacatat | ttgaatgtat | 3645 |

-continued

```
ttagaaaaat aaacaaatag gggttccgcg cacatttccc cgaaaagtgc cacctgacgt    3705
ctaagaaacc attattatca tgacattaac ctataaaaat aggcgtatca cgaggccctt    3765
tcgtc                                                                3770
```

```
<210> SEQ ID NO 12
<211> LENGTH: 100
<212> TYPE: PRT
<213> ORGANISM: Dengue virus

<400> SEQUENCE: 12
```

```
Met Asn Asp Gln Arg Lys Lys Ala Arg Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Ala Ala Glu Ile Gly Arg Met Leu Asn Ile Leu Asn
                85                  90                  95

Arg Arg Arg Arg
            100
```

```
<210> SEQ ID NO 13
<211> LENGTH: 6910
<212> TYPE: DNA
<213> ORGANISM: Dengue virus
<220> FEATURE:
<221> NAME/KEY: misc_feature
<223> OTHER INFORMATION: DENV1 prM E (F108A K246M)
<220> FEATURE:
<221> NAME/KEY: CDS
<222> LOCATION: (1137)..(3164)

<400> SEQUENCE: 13
```

```
gaattcccat tgcatacgtt gtatccatat cataatatgt acatttatat tggctcatgt     60
ccaacattac cgccatgttg acattgatta ttgactagtt attaatagta atcaattacg    120
gggtcattag ttcatagccc atatatggag ttccgcgtta cataacttac ggtaaatggc    180
ccgcctggct gaccgcccaa cgacccccgc ccattgacgt caataatgac gtatgttccc    240
atagtaacgc caatagggac tttccattga cgtcaatggg tggagtattt acggtaaact    300
gcccacttgg cagtacatca agtgtatcat atgccaagta cgccccctat tgacgtcaat    360
gacggtaaat ggcccgcctg gcattatgcc cagtacatga ccttatggga ctttcctact    420
tggcagtaca tctacgtatt agtcatcgct attaccatgg tgatgcggtt ttggcagtac    480
atcaatgggc gtggatagcg gtttgactca cggggatttc caagtctcca ccccattgac    540
gtcaatggga gtttgttttg gcaccaaaat caacgggact ttccaaaatg tcgtaacaac    600
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccat cggctcgcat ctctccttca cgcgcccgcc    780
gccctacctg aggccgccat ccacgccggt tgagtcgcgt tctgccgcct ccgcctgtg     840 gtgcctcctg aactgcgtcc gccgtctagg taagtttaaa gctcaggtcg agaccgggcc    900
```

-continued

```
tttgtccggc gctcccttgg agcctaccta gactcagccg gctctccacg ctttgcctga    960
ccctgcttgc tcaactctag ttaacggtgg agggcagtgt agtctgagca gtactcgttg   1020
ctgccgcgcg cgccaccaga cataatagct gacagactaa cagactgttc ctttccatgg   1080
gtcttttctg cagtcaccgt cgtcgacacg tgtgatcaga tatcgcggcc gccacc atg   1139
                                                                 Met
                                                                  1
```

| | | | | | | | | | | | | | | | | |
|---|---|---|---|---|---|---|---|---|---|---|---|---|---|---|---|---|
| tcg | gtg | acc | atg | ctc | ctc | atg | ctg | ctg | ccc | aca | gcc | ctg | gcg | ttc | cat | 1187 |
| Ser | Val | Thr | Met | Leu | Leu | Met | Leu | Leu | Pro | Thr | Ala | Leu | Ala | Phe | His | |
| | | 5 | | | | 10 | | | | | 15 | | | | | |
| ctg | acc | acc | cga | ggg | gga | gag | ccg | cac | atg | ata | gtt | agc | aag | cag | gaa | 1235 |
| Leu | Thr | Thr | Arg | Gly | Gly | Glu | Pro | His | Met | Ile | Val | Ser | Lys | Gln | Glu | |
| | | 20 | | | | 25 | | | | 30 | | | | | | |
| aga | gga | aaa | tca | ctt | ttg | ttt | aag | acc | tct | gca | ggt | gtc | aac | atg | tgc | 1283 |
| Arg | Gly | Lys | Ser | Leu | Leu | Phe | Lys | Thr | Ser | Ala | Gly | Val | Asn | Met | Cys | |
| | 35 | | | | 40 | | | | | 45 | | | | | | |
| acc | ctt | att | gca | atg | gat | ttg | gga | gag | tta | tgt | gag | gac | aca | atg | acc | 1331 |
| Thr | Leu | Ile | Ala | Met | Asp | Leu | Gly | Glu | Leu | Cys | Glu | Asp | Thr | Met | Thr | |
| 50 | | | | 55 | | | | 60 | | | | 65 | | | | |
| tac | aaa | tgc | ccc | cgg | atc | act | gag | acg | gaa | cca | gat | gac | gtt | gac | tgt | 1379 |
| Tyr | Lys | Cys | Pro | Arg | Ile | Thr | Glu | Thr | Glu | Pro | Asp | Asp | Val | Asp | Cys | |
| | | | 70 | | | | 75 | | | | | 80 | | | | |
| tgg | tgc | aat | gcc | acg | gag | aca | tgg | gtg | acc | tat | gga | aca | tgt | tct | caa | 1427 |
| Trp | Cys | Asn | Ala | Thr | Glu | Thr | Trp | Val | Thr | Tyr | Gly | Thr | Cys | Ser | Gln | |
| | | 85 | | | | 90 | | | | | 95 | | | | | |
| act | ggt | gaa | cac | cga | cga | gac | aaa | cgt | tcc | gtc | gca | ctg | gca | cca | cac | 1475 |
| Thr | Gly | Glu | His | Arg | Arg | Asp | Lys | Arg | Ser | Val | Ala | Leu | Ala | Pro | His | |
| | 100 | | | | 105 | | | | | 110 | | | | | | |
| gta | ggg | ctt | ggt | cta | gaa | aca | aga | acc | gaa | acg | tgg | atg | tcc | tct | gaa | 1523 |
| Val | Gly | Leu | Gly | Leu | Glu | Thr | Arg | Thr | Glu | Thr | Trp | Met | Ser | Ser | Glu | |
| | 115 | | | | | 120 | | | | | 125 | | | | | |
| ggc | gct | tgg | aaa | caa | ata | caa | aaa | gtg | gag | acc | tgg | gct | ctg | aga | cac | 1571 |
| Gly | Ala | Trp | Lys | Gln | Ile | Gln | Lys | Val | Glu | Thr | Trp | Ala | Leu | Arg | His | |
| 130 | | | | 135 | | | | 140 | | | | | 145 | | | |
| cca | gga | ttc | acg | gtg | ata | gcc | ctt | ttt | cta | gca | cat | gcc | ata | gga | aca | 1619 |
| Pro | Gly | Phe | Thr | Val | Ile | Ala | Leu | Phe | Leu | Ala | His | Ala | Ile | Gly | Thr | |
| | | | | 150 | | | | | 155 | | | | | 160 | | |
| tcc | atc | acc | cag | aaa | ggg | atc | att | ttt | att | ttg | ctg | atg | ctg | gta | act | 1667 |
| Ser | Ile | Thr | Gln | Lys | Gly | Ile | Ile | Phe | Ile | Leu | Leu | Met | Leu | Val | Thr | |
| | | 165 | | | | | 170 | | | | 175 | | | | | |
| cca | tcc | atg | gcc | atg | cgg | tgc | gtg | gga | ata | ggc | aac | aga | gac | ttc | gtg | 1715 |
| Pro | Ser | Met | Ala | Met | Arg | Cys | Val | Gly | Ile | Gly | Asn | Arg | Asp | Phe | Val | |
| | | 180 | | | | 185 | | | | | 190 | | | | | |
| gaa | gga | ctg | tca | gga | gct | acg | tgg | gtg | gat | gtg | gta | ctg | gag | cat | gga | 1763 |
| Glu | Gly | Leu | Ser | Gly | Ala | Thr | Trp | Val | Asp | Val | Val | Leu | Glu | His | Gly | |
| | 195 | | | | 200 | | | | | 205 | | | | | | |
| agt | tgc | gtc | act | acc | atg | gca | aaa | gac | aaa | cca | aca | ctg | gac | att | gaa | 1811 |
| Ser | Cys | Val | Thr | Thr | Met | Ala | Lys | Asp | Lys | Pro | Thr | Leu | Asp | Ile | Glu | |
| 210 | | | | 215 | | | | 220 | | | | | 225 | | | |
| ctc | ttg | aag | acg | gag | gtc | aca | aac | cct | gcc | gtc | ctg | cgc | aaa | ctg | tgc | 1859 |
| Leu | Leu | Lys | Thr | Glu | Val | Thr | Asn | Pro | Ala | Val | Leu | Arg | Lys | Leu | Cys | |
| | | | 230 | | | | 235 | | | | | 240 | | | | |
| att | gaa | gct | aaa | ata | tca | aac | acc | acc | gat | tcg | aga | tgt | cca | aca | | 1907 |
| Ile | Glu | Ala | Lys | Ile | Ser | Asn | Thr | Thr | Thr | Asp | Ser | Arg | Cys | Pro | Thr | |
| | | 245 | | | | | 250 | | | | 255 | | | | | |
| caa | gga | gaa | gcc | acg | ctg | gtg | gaa | gaa | cag | gac | acg | aac | ttt | gtg | tgt | 1955 |
| Gln | Gly | Glu | Ala | Thr | Leu | Val | Glu | Glu | Gln | Asp | Thr | Asn | Phe | Val | Cys | |
| | 260 | | | | 265 | | | | | 270 | | | | | | |
| cga | cga | acg | ttc | gtg | gac | aga | ggc | tgg | ggc | aat | ggt | tgt | ggg | cta | gcc | 2003 |

|     |     |     |     |     |     |     |     |     |     |     |     |     |     |     |      |
|-----|-----|-----|-----|-----|-----|-----|-----|-----|-----|-----|-----|-----|-----|-----|------|
| Arg | Arg | Thr | Phe | Val | Asp | Arg | Gly | Trp | Gly | Asn | Gly | Cys | Gly | Leu | Ala  |
|     | 275 |     |     |     | 280 |     |     |     | 285 |     |     |     |     |     |      |

| gga | aaa | ggt | agc | tta | ata | acg | tgt | gct | aag | ttt | aag | tgt | gta | aca | aaa | 2051 |
|-----|-----|-----|-----|-----|-----|-----|-----|-----|-----|-----|-----|-----|-----|-----|-----|------|
| Gly | Lys | Gly | Ser | Leu | Ile | Thr | Cys | Ala | Lys | Phe | Lys | Cys | Val | Thr | Lys |      |
| 290 |     |     |     |     | 295 |     |     |     |     | 300 |     |     |     |     | 305 |      |

| ctg | gaa | gga | aag | ata | gtc | caa | tat | gaa | aac | tta | aaa | tat | tca | gtg | ata | 2099 |
|-----|-----|-----|-----|-----|-----|-----|-----|-----|-----|-----|-----|-----|-----|-----|-----|------|
| Leu | Glu | Gly | Lys | Ile | Val | Gln | Tyr | Glu | Asn | Leu | Lys | Tyr | Ser | Val | Ile |      |
|     |     |     |     | 310 |     |     |     |     | 315 |     |     |     |     | 320 |     |      |

| gtc | acc | gta | cac | act | gga | gac | cag | cac | caa | gtt | gga | aat | gag | acc | aca | 2147 |
|-----|-----|-----|-----|-----|-----|-----|-----|-----|-----|-----|-----|-----|-----|-----|-----|------|
| Val | Thr | Val | His | Thr | Gly | Asp | Gln | His | Gln | Val | Gly | Asn | Glu | Thr | Thr |      |
|     |     |     | 325 |     |     |     |     | 330 |     |     |     |     | 335 |     |     |      |

| gaa | cat | gga | aca | act | gca | acc | ata | aca | cct | caa | gct | ccc | acg | tcg | gaa | 2195 |
|-----|-----|-----|-----|-----|-----|-----|-----|-----|-----|-----|-----|-----|-----|-----|-----|------|
| Glu | His | Gly | Thr | Thr | Ala | Thr | Ile | Thr | Pro | Gln | Ala | Pro | Thr | Ser | Glu |      |
|     |     | 340 |     |     |     |     | 345 |     |     |     |     | 350 |     |     |     |      |

| ata | cag | ctg | aca | gac | tac | gga | gct | cta | aca | ttg | gat | tgt | tca | cct | aga | 2243 |
|-----|-----|-----|-----|-----|-----|-----|-----|-----|-----|-----|-----|-----|-----|-----|-----|------|
| Ile | Gln | Leu | Thr | Asp | Tyr | Gly | Ala | Leu | Thr | Leu | Asp | Cys | Ser | Pro | Arg |      |
| 355 |     |     |     |     | 360 |     |     |     |     | 365 |     |     |     |     |     |      |

| aca | ggg | cta | gac | ttt | aat | gag | atg | gtg | ttg | ttg | aca | atg | gaa | aat | aaa | 2291 |
|-----|-----|-----|-----|-----|-----|-----|-----|-----|-----|-----|-----|-----|-----|-----|-----|------|
| Thr | Gly | Leu | Asp | Phe | Asn | Glu | Met | Val | Leu | Leu | Thr | Met | Glu | Asn | Lys |      |
| 370 |     |     |     |     | 375 |     |     |     |     | 380 |     |     |     |     | 385 |      |

| tca | tgg | ctc | gtc | cac | aaa | caa | tgg | ttt | cta | gac | tta | cca | ctg | cct | tgg | 2339 |
|-----|-----|-----|-----|-----|-----|-----|-----|-----|-----|-----|-----|-----|-----|-----|-----|------|
| Ser | Trp | Leu | Val | His | Lys | Gln | Trp | Phe | Leu | Asp | Leu | Pro | Leu | Pro | Trp |      |
|     |     |     |     | 390 |     |     |     |     | 395 |     |     |     |     | 400 |     |      |

| acc | tcg | ggg | gct | tca | aca | tcc | caa | gag | act | tgg | aat | aga | caa | gac | ttg | 2387 |
|-----|-----|-----|-----|-----|-----|-----|-----|-----|-----|-----|-----|-----|-----|-----|-----|------|
| Thr | Ser | Gly | Ala | Ser | Thr | Ser | Gln | Glu | Thr | Trp | Asn | Arg | Gln | Asp | Leu |      |
|     |     |     | 405 |     |     |     |     | 410 |     |     |     |     | 415 |     |     |      |

| ctg | gtc | aca | ttt | aag | aca | gct | cat | gca | aaa | aag | cag | gaa | gta | gtc | gta | 2435 |
|-----|-----|-----|-----|-----|-----|-----|-----|-----|-----|-----|-----|-----|-----|-----|-----|------|
| Leu | Val | Thr | Phe | Lys | Thr | Ala | His | Ala | Lys | Lys | Gln | Glu | Val | Val | Val |      |
|     |     | 420 |     |     |     |     | 425 |     |     |     |     | 430 |     |     |     |      |

| cta | gga | tca | caa | gaa | gga | gca | atg | cac | act | gcg | ttg | act | gga | gcg | aca | 2483 |
|-----|-----|-----|-----|-----|-----|-----|-----|-----|-----|-----|-----|-----|-----|-----|-----|------|
| Leu | Gly | Ser | Gln | Glu | Gly | Ala | Met | His | Thr | Ala | Leu | Thr | Gly | Ala | Thr |      |
| 435 |     |     |     |     | 440 |     |     |     |     | 445 |     |     |     |     |     |      |

| gaa | atc | caa | acg | tct | gga | acg | aca | aca | att | ttt | gca | gga | cac | ctg | aaa | 2531 |
|-----|-----|-----|-----|-----|-----|-----|-----|-----|-----|-----|-----|-----|-----|-----|-----|------|
| Glu | Ile | Gln | Thr | Ser | Gly | Thr | Thr | Thr | Ile | Phe | Ala | Gly | His | Leu | Lys |      |
| 450 |     |     |     |     | 455 |     |     |     |     | 460 |     |     |     |     | 465 |      |

| tgc | aga | cta | aaa | atg | gat | aaa | ctg | act | tta | aaa | ggg | atg | tca | tat | gta | 2579 |
|-----|-----|-----|-----|-----|-----|-----|-----|-----|-----|-----|-----|-----|-----|-----|-----|------|
| Cys | Arg | Leu | Lys | Met | Asp | Lys | Leu | Thr | Leu | Lys | Gly | Met | Ser | Tyr | Val |      |
|     |     |     |     | 470 |     |     |     |     | 475 |     |     |     |     | 480 |     |      |

| atg | tgc | aca | ggg | tca | ttc | aag | tta | gag | aag | gaa | gtg | gct | gag | acc | cag | 2627 |
|-----|-----|-----|-----|-----|-----|-----|-----|-----|-----|-----|-----|-----|-----|-----|-----|------|
| Met | Cys | Thr | Gly | Ser | Phe | Lys | Leu | Glu | Lys | Glu | Val | Ala | Glu | Thr | Gln |      |
|     |     |     | 485 |     |     |     |     | 490 |     |     |     |     | 495 |     |     |      |

| cat | gga | act | gtt | cta | gtg | cag | gtt | aaa | tac | gaa | gga | aca | gat | gca | cca | 2675 |
|-----|-----|-----|-----|-----|-----|-----|-----|-----|-----|-----|-----|-----|-----|-----|-----|------|
| His | Gly | Thr | Val | Leu | Val | Gln | Val | Lys | Tyr | Glu | Gly | Thr | Asp | Ala | Pro |      |
|     |     | 500 |     |     |     |     | 505 |     |     |     |     | 510 |     |     |     |      |

| tgc | aag | atc | ccc | ttc | tcg | tcc | caa | gat | gag | aag | gga | gta | acc | cag | aat | 2723 |
|-----|-----|-----|-----|-----|-----|-----|-----|-----|-----|-----|-----|-----|-----|-----|-----|------|
| Cys | Lys | Ile | Pro | Phe | Ser | Ser | Gln | Asp | Glu | Lys | Gly | Val | Thr | Gln | Asn |      |
| 515 |     |     |     |     | 520 |     |     |     |     | 525 |     |     |     |     |     |      |

| ggg | aga | ttg | ata | aca | gcc | aac | ccc | ata | gtc | act | gac | aaa | gaa | aaa | cca | 2771 |
|-----|-----|-----|-----|-----|-----|-----|-----|-----|-----|-----|-----|-----|-----|-----|-----|------|
| Gly | Arg | Leu | Ile | Thr | Ala | Asn | Pro | Ile | Val | Thr | Asp | Lys | Glu | Lys | Pro |      |
| 530 |     |     |     |     | 535 |     |     |     |     | 540 |     |     |     |     | 545 |      |

| gtc | aac | att | gaa | gcg | gag | cca | cct | ttt | ggt | gag | agc | tac | att | gtg | gta | 2819 |
|-----|-----|-----|-----|-----|-----|-----|-----|-----|-----|-----|-----|-----|-----|-----|-----|------|
| Val | Asn | Ile | Glu | Ala | Glu | Pro | Pro | Phe | Gly | Glu | Ser | Tyr | Ile | Val | Val |      |
|     |     |     | 550 |     |     |     |     | 555 |     |     |     |     | 560 |     |     |      |

| gga | gca | ggt | gaa | aaa | gct | ttg | aaa | cta | agc | tgg | ttc | aag | aag | gga | agc | 2867 |
|-----|-----|-----|-----|-----|-----|-----|-----|-----|-----|-----|-----|-----|-----|-----|-----|------|
| Gly | Ala | Gly | Glu | Lys | Ala | Leu | Lys | Leu | Ser | Trp | Phe | Lys | Lys | Gly | Ser |      |
|     |     |     | 565 |     |     |     |     | 570 |     |     |     |     | 575 |     |     |      |

| agt | ata | ggg | aaa | atg | ttt | gaa | gca | act | gcc | cgt | gga | gca | cga | agg | atg | 2915 |
|-----|-----|-----|-----|-----|-----|-----|-----|-----|-----|-----|-----|-----|-----|-----|-----|------|
| Ser | Ile | Gly | Lys | Met | Phe | Glu | Ala | Thr | Ala | Arg | Gly | Ala | Arg | Arg | Met |      |
|     |     | 580 |     |     |     |     | 585 |     |     |     |     | 590 |     |     |     |      |

```
gcc atc ctg gga gac act gca tgg gac ttc ggt tct ata gga ggg gtg    2963
Ala Ile Leu Gly Asp Thr Ala Trp Asp Phe Gly Ser Ile Gly Gly Val
        595                 600                 605 ttc acg tct gtg gga aaa ctg ata cac cag att ttt ggg act gcg tat    3011
Phe Thr Ser Val Gly Lys Leu Ile His Gln Ile Phe Gly Thr Ala Tyr
610                 615                 620                 625 gga gtt ttg ttc agc ggt gtt tct tgg acc atg aag ata gga ata ggg    3059
Gly Val Leu Phe Ser Gly Val Ser Trp Thr Met Lys Ile Gly Ile Gly
                630                 635                 640 att ctg ctg aca tgg cta gga tta aac tca agg agc acg tcc ctt tca    3107
Ile Leu Leu Thr Trp Leu Gly Leu Asn Ser Arg Ser Thr Ser Leu Ser
            645                 650                 655 atg acg tgt atc gca gtt ggc atg gtc acg ctg tac cta gga gtc atg    3155
Met Thr Cys Ile Ala Val Gly Met Val Thr Leu Tyr Leu Gly Val Met
        660                 665                 670 gtt cag gcg taataaagat ctgctgtgcc ttctagttgc cagccatctg            3204
Val Gln Ala
675 ttgtttgccc ctccccgtg ccttccttga ccctggaagg tgccactccc actgtccttt    3264 cctaataaaa tgaggaaatt gcatcgcatt gtctgagtag gtgtcattct attctggggg    3324 gtggggtggg gcaggacagc aaggggagg attgggaaga caatagcagg catgctgggg     3384 atgcggtggg ctctatgggt acccaggtgc tgaagaattg acccggttcc tcctgggcca    3444 gaaagaagca ggcacatccc cttctctgtg acacaccctg tccacgcccc tggttcttag    3504 ttccagcccc actcatagga cactcatagc tcaggagggc tccgccttca atcccacccg    3564 ctaaagtact tggagcggtc tctccctccc tcatcagccc accaaaccaa acctagcctc    3624 caagagtggg aagaaattaa agcaagatag gctattaagt gcagagggag agaaaatgcc    3684 tccaacatgt gaggaagtaa tgagagaaat catagaattt taaggccatg atttaaggcc    3744 atcatggcct aagcttgaaa ggagatagga tcaaagcttg gcgtaatcat ggtcatagct    3804 gtttcctgtg tgaaattgtt atccgctcac aattccacac aacatacgag ccggaagcat    3864 aaagtgtaaa gcctggggtg cctaatgagt gagctaactc acattaattg cgttgcgctc    3924 actgcccgct ttccagtcgg gaaacctgtc gtgccagctg cattaatgaa tcggccaacg    3984 cgcggggaga ggcggtttgc gtattgggcg ctcttccgct tcctcgctca ctgactcgct    4044 gcgctcggtc gttcggctgc ggcgagcggt atcagctcac tcaaaggcgg taatacggtt    4104 atccacagaa tcaggggata acgcaggaaa gaacatgtga gcaaaaggcc agcaaaaggc    4164 caggaaccgt aaaaaggccg cgttgctggc gtttttccat aggctccgcc cccctgacga    4224 gcatcacaaa aatcgacgct caagtcagag gtggcgaaac ccgacaggac tataaagata    4284 ccaggcgttt ccccctggaa gctccctcgt gcgctctcct gttccgaccc tgccgcttac    4344 cggatacctg tccgcctttc tcccttcggg aagcgtggcg ctttctcata gctcacgctg    4404 taggtatctc agttcggtgt aggtcgttcg ctccaagctg ggctgtgtgc acgaaccccc    4464 cgttcagccc gaccgctgcg ccttatccgg taactatcgt cttgagtcca acccggtaag    4524 acacgactta tcgccactgg cagcagccac tggtaacagg attagcagag cgaggtatgt    4584 aggcggtgct acagagttct tgaagtggtg gcctaactac ggctacacta agaacagt     4644 atttggtatc tgcgctctgc tgaagccagt taccttcgga aaagagttg gtagctcttg     4704 atccggcaaa caaccaccg ctggtagcgg tggttttttt gtttgcaagc agcagattac     4764 gcgcagaaaa aaaggatctc aagaagatcc tttgatcttt tctacggggt ctgacgctca    4824 gtggaacgaa aactcacgtt aagggatttt ggtcatgaga ttatcaaaaa ggatcttcac    4884
```

-continued

```
ctagatcctt ttaaattaaa aatgaagttt taaatcaatc taaagtatat atgagtaaac   4944
ttggtctgac agttaccaat gcttaatcag tgaggcacct atctcagcga tctgtctatt   5004
tcgttcatcc atagttgcct gactccccgt cgtgtagata actacgatac gggagggctt   5064
accatctggc cccagtgctg caatgatacc gcgagaacca cgctcaccgg ctccagattt   5124
atcagcaata aaccagccag ccggaagggc cgagcgcaga agtggtcctg caactttatc   5184
cgcctccatc cagtctatta attgttgccg ggaagctaga gtaagtagtt cgccagttaa   5244
tagtttgcgc aacgttgttg ccattgctac aggcatcgtg gtgtcacgct cgtcgtttgg   5304
tatggcttca ttcagctccg gttcccaacg atcaaggcga gttacatgat cccccatgtt   5364
gtgcaaaaaa gcggttagct ccttcggtcc tccgatcgtt gtcagaagta agttggccgc   5424
agtgttatca ctcatggtta tggcagcact gcataattct cttactgtca tgccatccgt   5484
aagatgcttt tctgtgactg gtgagtactc aaccaagtca ttctgagaat agtgtatgcg   5544
gcgaccgagt tgctcttgcc cggcgtcaat acgggataat accgcgccac atagcagaac   5604
tttaaaagtg ctcatcattg gaaaacgttc ttcggggcga aaactctcaa ggatcttacc   5664
gctgttgaga tccagttcga tgtaacccac tcgtgcaccc aactgatctt cagcatcttt   5724
tactttcacc agcgtttctg ggtgagcaaa aacaggaagg caaaatgccg caaaaaaggg   5784
aataagggcg acacggaaat gttgaatact catactcttc ctttttcaat attattgaag   5844
catttatcag ggttattgtc tcatgagcgg atacatattt gaatgtattt agaaaaataa   5904
acaaataggg gttccgcgca catttccccg aaaagtgcca cctgacgtct aagaaaccat   5964
tattatcatg acattaacct ataaaaatag gcgtatcacg aggccctttc gggtcgcgcg   6024
tttcggtgat gacggtgaaa acctctgaca catgcagctc ccgttgacgg tcacagcttg   6084
tctgtaagcg gatgccggga gcagacaagc ccgtcagggc gcgtcagcgg gtgttggcgg   6144
gtgtcggggc tggcttaact atgcggcatc agagcagatt gtactgagag tgcaccataa   6204
aattgtaaac gttaatattt tgttaaaatt cgcgttaaat ttttgttaaa tcagctcatt   6264
ttttaaccaa taggccgaaa tcggcaaaat cccttataaa tcaaaagaat agcccgagat   6324
agggttgagt gttgttccag tttggaacaa gagtccacta ttaaagaacg tggactccaa   6384
cgtcaaaggg cgaaaaaccg tctatcaggg cgatggccca ctacgtgaac catcacccaa   6444
atcaagtttt ttggggtcga ggtgccgtaa agcactaaat cggaacccta aagggagccc   6504
ccgatttaga gcttgacggg gaaagccggc gaacgtggcg agaaaggaag ggaagaaagc   6564
gaaaggagcg ggcgctaggg cgctggcaag tgtagcggtc acgctgcgcg taaccaccac   6624
acccgccgcg cttaatgcgc cgctacaggg cgcgtactat ggttgctttg acgtatgcgg   6684
tgtgaaatac cgcacagatg cgtaaggaga aaataccgca tcaggcgcca ttcgccattc   6744
aggctgcgca actgttggga agggcgatcg gtgcgggcct cttcgctatt acgccagctg   6804
gcgaaagggg gatgtgctgc aaggcgatta agttgggtaa cgccagggtt ttcccagtca   6864
cgacgttgta aaacgacggc cagtgaattc catggtctca actttc                  6910

<210> SEQ ID NO 14
<211> LENGTH: 676
<212> TYPE: PRT
<213> ORGANISM: Dengue virus

<400> SEQUENCE: 14

Met Ser Val Thr Met Leu Leu Met Leu Leu Pro Thr Ala Leu Ala Phe
1               5                   10                  15
```

-continued

His Leu Thr Thr Arg Gly Gly Glu Pro His Met Ile Val Ser Lys Gln
              20                  25                  30

Glu Arg Gly Lys Ser Leu Leu Phe Lys Thr Ser Ala Gly Val Asn Met
              35                  40                  45

Cys Thr Leu Ile Ala Met Asp Leu Gly Glu Leu Cys Glu Asp Thr Met
 50                  55                  60

Thr Tyr Lys Cys Pro Arg Ile Thr Glu Thr Glu Pro Asp Asp Val Asp
 65                  70                  75                  80

Cys Trp Cys Asn Ala Thr Glu Thr Trp Val Thr Tyr Gly Thr Cys Ser
                 85                  90                  95

Gln Thr Gly Glu His Arg Arg Asp Lys Arg Ser Val Ala Leu Ala Pro
                100                 105                 110

His Val Gly Leu Gly Leu Glu Thr Arg Thr Glu Thr Trp Met Ser Ser
                115                 120                 125

Glu Gly Ala Trp Lys Gln Ile Gln Lys Val Glu Thr Trp Ala Leu Arg
130                 135                 140

His Pro Gly Phe Thr Val Ile Ala Leu Phe Leu Ala His Ala Ile Gly
145                 150                 155                 160

Thr Ser Ile Thr Gln Lys Gly Ile Ile Phe Ile Leu Leu Met Leu Val
                165                 170                 175

Thr Pro Ser Met Ala Met Arg Cys Val Gly Ile Gly Asn Arg Asp Phe
                180                 185                 190

Val Glu Gly Leu Ser Gly Ala Thr Trp Val Asp Val Val Leu Glu His
                195                 200                 205

Gly Ser Cys Val Thr Thr Met Ala Lys Asp Lys Pro Thr Leu Asp Ile
210                 215                 220

Glu Leu Leu Lys Thr Glu Val Thr Asn Pro Ala Val Leu Arg Lys Leu
225                 230                 235                 240

Cys Ile Glu Ala Lys Ile Ser Asn Thr Thr Thr Asp Ser Arg Cys Pro
                245                 250                 255

Thr Gln Gly Glu Ala Thr Leu Val Glu Glu Gln Asp Thr Asn Phe Val
                260                 265                 270

Cys Arg Arg Thr Phe Val Asp Arg Gly Trp Gly Asn Gly Cys Gly Leu
                275                 280                 285

Ala Gly Lys Gly Ser Leu Ile Thr Cys Ala Lys Phe Lys Cys Val Thr
                290                 295                 300

Lys Leu Glu Gly Lys Ile Val Gln Tyr Glu Asn Leu Lys Tyr Ser Val
305                 310                 315                 320

Ile Val Thr Val His Thr Gly Asp Gln His Gln Val Gly Asn Glu Thr
                325                 330                 335

Thr Glu His Gly Thr Thr Ala Thr Ile Thr Pro Gln Ala Pro Thr Ser
                340                 345                 350

Glu Ile Gln Leu Thr Asp Tyr Gly Ala Leu Thr Leu Asp Cys Ser Pro
                355                 360                 365

Arg Thr Gly Leu Asp Phe Asn Glu Met Val Leu Leu Thr Met Glu Asn
                370                 375                 380

Lys Ser Trp Leu Val His Lys Gln Trp Phe Leu Asp Leu Pro Leu Pro
385                 390                 395                 400

Trp Thr Ser Gly Ala Ser Thr Ser Gln Glu Thr Trp Asn Arg Gln Asp
                405                 410                 415

Leu Leu Val Thr Phe Lys Thr Ala His Ala Lys Lys Gln Glu Val Val
                420                 425                 430

Val Leu Gly Ser Gln Glu Gly Ala Met His Thr Ala Leu Thr Gly Ala
            435                 440                 445

Thr Glu Ile Gln Thr Ser Gly Thr Thr Thr Ile Phe Ala Gly His Leu
        450                 455                 460

Lys Cys Arg Leu Lys Met Asp Lys Leu Thr Leu Lys Gly Met Ser Tyr
465                 470                 475                 480

Val Met Cys Thr Gly Ser Phe Lys Leu Glu Lys Glu Val Ala Glu Thr
                485                 490                 495

Gln His Gly Thr Val Leu Val Gln Val Lys Tyr Glu Gly Thr Asp Ala
            500                 505                 510

Pro Cys Lys Ile Pro Phe Ser Ser Gln Asp Glu Lys Gly Val Thr Gln
        515                 520                 525

Asn Gly Arg Leu Ile Thr Ala Asn Pro Ile Val Thr Asp Lys Glu Lys
    530                 535                 540

Pro Val Asn Ile Glu Ala Glu Pro Pro Phe Gly Glu Ser Tyr Ile Val
545                 550                 555                 560

Val Gly Ala Gly Glu Lys Ala Leu Lys Leu Ser Trp Phe Lys Lys Gly
                565                 570                 575

Ser Ser Ile Gly Lys Met Phe Glu Ala Thr Ala Arg Gly Ala Arg Arg
            580                 585                 590

Met Ala Ile Leu Gly Asp Thr Ala Trp Asp Phe Gly Ser Ile Gly Gly
        595                 600                 605

Val Phe Thr Ser Val Gly Lys Leu Ile His Gln Ile Phe Gly Thr Ala
610                 615                 620

Tyr Gly Val Leu Phe Ser Gly Val Ser Trp Thr Met Lys Ile Gly Ile
625                 630                 635                 640

Gly Ile Leu Leu Thr Trp Leu Gly Leu Asn Ser Arg Ser Thr Ser Leu
                645                 650                 655

Ser Met Thr Cys Ile Ala Val Gly Met Val Thr Leu Tyr Leu Gly Val
            660                 665                 670

Met Val Gln Ala
        675

<210> SEQ ID NO 15
<211> LENGTH: 6910
<212> TYPE: DNA
<213> ORGANISM: Dengue virus
<220> FEATURE:
<221> NAME/KEY: misc_feature
<223> OTHER INFORMATION: DENV1 prM E (F108A K203N) VLP D01
<220> FEATURE:
<221> NAME/KEY: CDS
<222> LOCATION: (1137)..(3164)

<400> SEQUENCE: 15

```
gaattcccat tgcatacgtt gtatccatat cataatatgt acatttatat tggctcatgt     60
ccaacattac cgccatgttg acattgatta ttgactagtt attaatagta atcaattacg    120
gggtcattag ttcatagccc atatatggag ttccgcgtta cataacttac ggtaaatggc    180
ccgcctggct gaccgcccaa cgacccccgc ccattgacgt caataatgac gtatgttccc    240
atagtaacgc caatagggac tttccattga cgtcaatggg tggagtattt acggtaaact    300
gcccacttgg cagtacatca agtgtatcat atgccaagta cgccccctat tgacgtcaat    360
gacggtaaat ggcccgcctg gcattatgcc cagtacatga ccttatggga ctttcctact    420
tggcagtaca tctacgtatt agtcatcgct attaccatgg tgatgcggtt ttggcagtac    480
atcaatgggc gtggatagcg gtttgactca cggggatttc caagtctcca ccccattgac    540
```

-continued

```
gtcaatggga gtttgttttg gcaccaaaat caacgggact ttccaaaatg tcgtaacaac    600
tccgccccat tgacgcaaat gggcggtagg cgtgtacggt gggaggtcta tataagcaga    660
gctcgtttag tgaaccgtca gatcgcctgg agacgccatc cacgctgttt tgacctccat    720
agaagacacc gggaccgatc cagcctccat cggctcgcat ctctccttca cgcgcccgcc    780
gccctacctg aggccgccat ccacgccggt tgagtcgcgt tctgccgcct cccgcctgtg    840
gtgcctcctg aactgcgtcc gccgtctagg taagtttaaa gctcaggtcg agaccgggcc    900
tttgtccggc gctcccttgg agcctaccta gactcagccg gctctccacg ctttgcctga    960
ccctgcttgc tcaactctag ttaacggtgg agggcagtgt agtctgagca gtactcgttg   1020
ctgccgcgcg cgccaccaga cataatagct gacagactaa cagactgttc ctttccatgg   1080
gtcttttctg cagtcaccgt cgtcgacacg tgtgatcaga tatcgcggcc gccacc atg   1139
                                                               Met
                                                                 1
```

```
tcg gtg acc atg ctc ctc atg ctg ctg ccc aca gcc ctg gcg ttc cat    1187
Ser Val Thr Met Leu Leu Met Leu Leu Pro Thr Ala Leu Ala Phe His
         5                  10                  15 ctg acc acc cga ggg gga gag ccg cac atg ata gtt agc aag cag gaa    1235
Leu Thr Thr Arg Gly Gly Glu Pro His Met Ile Val Ser Lys Gln Glu
     20                  25                  30 aga gga aaa tca ctt ttg ttt aag acc tct gca ggt gtc aac atg tgc    1283
Arg Gly Lys Ser Leu Leu Phe Lys Thr Ser Ala Gly Val Asn Met Cys
 35                  40                  45 acc ctt att gca atg gat ttg gga gag tta tgt gag gac aca atg acc    1331
Thr Leu Ile Ala Met Asp Leu Gly Glu Leu Cys Glu Asp Thr Met Thr
 50                  55                  60                  65 tac aaa tgc ccc cgg atc act gag acg gaa cca gat gac gtt gac tgt    1379
Tyr Lys Cys Pro Arg Ile Thr Glu Thr Glu Pro Asp Asp Val Asp Cys
                 70                  75                  80 tgg tgc aat gcc acg gag aca tgg gtg acc tat gga aca tgt tct caa    1427
Trp Cys Asn Ala Thr Glu Thr Trp Val Thr Tyr Gly Thr Cys Ser Gln
             85                  90                  95 act ggt gaa cac cga cga gac aaa cgt tcc gtc gca ctg gca cca cac    1475
Thr Gly Glu His Arg Arg Asp Lys Arg Ser Val Ala Leu Ala Pro His
        100                 105                 110 gta ggg ctt ggt cta gaa aca aga acc gaa acg tgg atg tcc tct gaa    1523
Val Gly Leu Gly Leu Glu Thr Arg Thr Glu Thr Trp Met Ser Ser Glu
    115                 120                 125 ggc gct tgg aaa caa ata caa aaa gtg gag acc tgg gct ctg aga cac    1571
Gly Ala Trp Lys Gln Ile Gln Lys Val Glu Thr Trp Ala Leu Arg His
130                 135                 140                 145 cca gga ttc acg gtg ata gcc ctt ttt cta gca cat gcc ata gga aca    1619
Pro Gly Phe Thr Val Ile Ala Leu Phe Leu Ala His Ala Ile Gly Thr
                150                 155                 160 tcc atc acc cag aaa ggg atc att ttt att ttg ctg atg ctg gta act    1667
Ser Ile Thr Gln Lys Gly Ile Ile Phe Ile Leu Leu Met Leu Val Thr
            165                 170                 175 cca tcc atg gcc atg cgg tgc gtg gga ata ggc aac aga gac ttc gtg    1715
Pro Ser Met Ala Met Arg Cys Val Gly Ile Gly Asn Arg Asp Phe Val
        180                 185                 190 gaa gga ctg tca gga gct acg tgg gtg gat gtg gta ctg gag cat gga    1763
Glu Gly Leu Ser Gly Ala Thr Trp Val Asp Val Val Leu Glu His Gly
    195                 200                 205 agt tgc gtc act acc atg gca aaa gac aaa cca aca ctg gac att gaa    1811
Ser Cys Val Thr Thr Met Ala Lys Asp Lys Pro Thr Leu Asp Ile Glu
210                 215                 220                 225
```

| | | |
|---|---|---|
| ctc ttg aag acg gag gtc aca aac cct gcc gtc ctg cgc aaa ctg tgc<br>Leu Leu Lys Thr Glu Val Thr Asn Pro Ala Val Leu Arg Lys Leu Cys<br>230 235 240 | | 1859 |
| att gaa gct aaa ata tca aac acc acc acc gat tcg aga tgt cca aca<br>Ile Glu Ala Lys Ile Ser Asn Thr Thr Thr Asp Ser Arg Cys Pro Thr<br>245 250 255 | | 1907 |
| caa gga gaa gcc acg ctg gtg gaa gaa cag gac acg aac ttt gtg tgt<br>Gln Gly Glu Ala Thr Leu Val Glu Glu Gln Asp Thr Asn Phe Val Cys<br>260 265 270 | | 1955 |
| cga cga acg ttc gtg gac aga ggc tgg ggc aat ggt tgt ggg cta gcc<br>Arg Arg Thr Phe Val Asp Arg Gly Trp Gly Asn Gly Cys Gly Leu Ala<br>275 280 285 | | 2003 |
| gga aaa ggt agc tta ata acg tgt gct aag ttt aag tgt gtg aca aaa<br>Gly Lys Gly Ser Leu Ile Thr Cys Ala Lys Phe Lys Cys Val Thr Lys<br>290 295 300 305 | | 2051 |
| ctg gaa gga aag ata gtc caa tat gaa aac tta aaa tat tca gtg ata<br>Leu Glu Gly Lys Ile Val Gln Tyr Glu Asn Leu Lys Tyr Ser Val Ile<br>310 315 320 | | 2099 |
| gtc acc gta cac act gga gac cag cac caa gtt gga aat gag acc aca<br>Val Thr Val His Thr Gly Asp Gln His Gln Val Gly Asn Glu Thr Thr<br>325 330 335 | | 2147 |
| gaa cat gga aca act gca acc ata aca cct caa gct ccc acg tcg gaa<br>Glu His Gly Thr Thr Ala Thr Ile Thr Pro Gln Ala Pro Thr Ser Glu<br>340 345 350 | | 2195 |
| ata cag ctg aca gac tac gga gct cta aca ttg gat tgt tca cct aga<br>Ile Gln Leu Thr Asp Tyr Gly Ala Leu Thr Leu Asp Cys Ser Pro Arg<br>355 360 365 | | 2243 |
| aca ggg cta gac ttt aat gag atg gtg ttg ttg aca atg gaa aaa aaa<br>Thr Gly Leu Asp Phe Asn Glu Met Val Leu Leu Thr Met Glu Lys Lys<br>370 375 380 385 | | 2291 |
| tca tgg ctc gtc cac aaa caa tgg ttt cta gac tta cca ctg cct tgg<br>Ser Trp Leu Val His Lys Gln Trp Phe Leu Asp Leu Pro Leu Pro Trp<br>390 395 400 | | 2339 |
| acc tcg ggg gct tca aca tcc caa gag act tgg aat aga caa gac ttg<br>Thr Ser Gly Ala Ser Thr Ser Gln Glu Thr Trp Asn Arg Gln Asp Leu<br>405 410 415 | | 2387 |
| ctg gtc aca ttt aag aca gct cat gca atg aag cag gaa gta gtc gta<br>Leu Val Thr Phe Lys Thr Ala His Ala Met Lys Gln Glu Val Val Val<br>420 425 430 | | 2435 |
| cta gga tca caa gaa gga gca atg cac act gcg ttg act gga gcg aca<br>Leu Gly Ser Gln Glu Gly Ala Met His Thr Ala Leu Thr Gly Ala Thr<br>435 440 445 | | 2483 |
| gaa atc caa acg tct gga acg aca aca att ttt gca gga cac ctg aaa<br>Glu Ile Gln Thr Ser Gly Thr Thr Thr Ile Phe Ala Gly His Leu Lys<br>450 455 460 465 | | 2531 |
| tgc aga cta aaa atg gat aaa ctg act tta aaa ggg atg tca tat gta<br>Cys Arg Leu Lys Met Asp Lys Leu Thr Leu Lys Gly Met Ser Tyr Val<br>470 475 480 | | 2579 |
| atg tgc aca ggg tca ttc aag tta gag aag gaa gtg gct gag acc cag<br>Met Cys Thr Gly Ser Phe Lys Leu Glu Lys Glu Val Ala Glu Thr Gln<br>485 490 495 | | 2627 |
| cat gga act gtt cta gtg cag gtt aaa tac gaa gga aca gat gca cca<br>His Gly Thr Val Leu Val Gln Val Lys Tyr Glu Gly Thr Asp Ala Pro<br>500 505 510 | | 2675 |
| tgc aag atc ccc ttc tcg tcc caa gat gag aag gga gta acc cag aat<br>Cys Lys Ile Pro Phe Ser Ser Gln Asp Glu Lys Gly Val Thr Gln Asn<br>515 520 525 | | 2723 |
| ggg aga ttg ata aca gcc aac ccc ata gtc act gac aaa gaa aaa cca<br>Gly Arg Leu Ile Thr Ala Asn Pro Ile Val Thr Asp Lys Glu Lys Pro<br>530 535 540 545 | | 2771 |

| | |
|---|---|
| gtc aac att gaa gcg gag cca cct ttt ggt gag agc tac att gtg gta<br>Val Asn Ile Glu Ala Glu Pro Pro Phe Gly Glu Ser Tyr Ile Val Val<br>550 555 560 | 2819 |
| gga gca ggt gaa aaa gct ttg aaa cta agc tgg ttc aag aag gga agc<br>Gly Ala Gly Glu Lys Ala Leu Lys Leu Ser Trp Phe Lys Lys Gly Ser<br>565 570 575 | 2867 |
| agt ata ggg aaa atg ttt gaa gca act gcc cgt gga gca cga agg atg<br>Ser Ile Gly Lys Met Phe Glu Ala Thr Ala Arg Gly Ala Arg Arg Met<br>580 585 590 | 2915 |
| gcc atc ctg gga gac act gca tgg gac ttc ggt tct ata gga ggg gtg<br>Ala Ile Leu Gly Asp Thr Ala Trp Asp Phe Gly Ser Ile Gly Gly Val<br>595 600 605 | 2963 |
| ttc acg tct gtg gga aaa ctg ata cac cag att ttt ggg act gcg tat<br>Phe Thr Ser Val Gly Lys Leu Ile His Gln Ile Phe Gly Thr Ala Tyr<br>610 615 620 625 | 3011 |
| gga gtt ttg ttc agc ggt gtt tct tgg acc atg aag ata gga ata ggg<br>Gly Val Leu Phe Ser Gly Val Ser Trp Thr Met Lys Ile Gly Ile Gly<br>630 635 640 | 3059 |
| att ctg ctg aca tgg cta gga tta aac tca agg agc acg tcc ctt tca<br>Ile Leu Leu Thr Trp Leu Gly Leu Asn Ser Arg Ser Thr Ser Leu Ser<br>645 650 655 | 3107 |
| atg acg tgt atc gca gtt ggc atg gtc acg ctg tac cta gga gtc atg<br>Met Thr Cys Ile Ala Val Gly Met Val Thr Leu Tyr Leu Gly Val Met<br>660 665 670 | 3155 |
| gtt cag gcg taataaagat ctgctgtgcc ttctagttgc cagccatctg<br>Val Gln Ala<br>675 | 3204 |
| ttgtttgccc ctccccgtg ccttccttga ccctggaagg tgccactccc actgtccttt | 3264 |
| cctaataaaa tgaggaaatt gcatcgcatt gtctgagtag gtgtcattct attctggggg | 3324 |
| gtggggtggg gcaggacagc aaggggagg attgggaaga caatagcagg catgctgggg | 3384 |
| atgcggtggg ctctatgggt acccaggtgc tgaagaattg acccggttcc tcctgggcca | 3444 |
| gaaagaagca ggcacatccc cttctctgtg acacaccctg tccacgcccc tggttcttag | 3504 |
| ttccagcccc actcatagga cactcatagc tcaggagggc tccgccttca atcccacccg | 3564 |
| ctaaagtact tggagcggtc tctccctccc tcatcagccc accaaaccaa acctagcctc | 3624 |
| caagagtggg aagaaattaa agcaagatag gctattaagt gcagagggag agaaaatgcc | 3684 |
| tccaacatgt gaggaagtaa tgagagaaat catagaattt taaggccatg atttaaggcc | 3744 |
| atcatggcct aagcttgaaa ggagatagga tcaaagcttg gcgtaatcat ggtcatagct | 3804 |
| gtttcctgtg tgaaattgtt atccgctcac aattccacac aacatacgag ccggaagcat | 3864 |
| aaagtgtaaa gcctggggtg cctaatgagt gagctaactc acattaattg cgttgcgctc | 3924 |
| actgcccgct ttccagtcgg gaaacctgtc gtgccagctg cattaatgaa tcggccaacg | 3984 |
| cgcggggaga ggcggtttgc gtattgggcg ctcttccgct tcctcgctca ctgactcgct | 4044 |
| gcgctcggtc gttcggctgc ggcgagcggt atcagctcac tcaaaggcgg taatacggtt | 4104 |
| atccacagaa tcaggggata acgcaggaaa gaacatgtga gcaaaaggcc agcaaaaggc | 4164 |
| caggaaccgt aaaaaggccg cgttgctggc gtttttccat aggctccgcc ccctgacga | 4224 |
| gcatcacaaa aatcgacgct caagtcagag gtggcgaaac ccgacaggac tataaagata | 4284 |
| ccaggcgttt ccccctggaa gctccctcgt gcgctctcct gttccgaccc tgccgcttac | 4344 |
| cggatacctg tccgcctttc tcccttcggg aagcgtggcg ctttctcata gctcacgctg | 4404 |
| taggtatctc agttcggtgt aggtcgttcg ctccaagctg ggctgtgtgc acgaaccccc | 4464 |

-continued

```
cgttcagccc gaccgctgcg ccttatccgg taactatcgt cttgagtcca acccggtaag    4524
acacgactta tcgccactgg cagcagccac tggtaacagg attagcagag cgaggtatgt    4584
aggcggtgct acagagttct tgaagtggtg cctaactac ggctacacta gaagaacagt     4644
atttggtatc tgcgctctgc tgaagccagt taccttcgga aaaagagttg gtagctcttg    4704
atccggcaaa caaaccaccg ctggtagcgg tggttttttt gtttgcaagc agcagattac    4764
gcgcagaaaa aaaggatctc aagaagatcc tttgatcttt tctacggggt ctgacgctca    4824
gtggaacgaa aactcacgtt aagggatttt ggtcatgaga ttatcaaaaa ggatcttcac    4884
ctagatcctt ttaaattaaa aatgaagttt taaatcaatc taaagtatat atgagtaaac    4944
ttggtctgac agttaccaat gcttaatcag tgaggcacct atctcagcga tctgtctatt    5004
tcgttcatcc atagttgcct gactccccgt cgtgtagata actacgatac gggagggctt    5064
accatctggc cccagtgctg caatgatacc gcgagaacca cgctcaccgg ctccagattt    5124
atcagcaata aaccagccag ccggaagggc cgagcgcaga agtggtcctg caactttatc    5184
cgcctccatc cagtctatta attgttgccg ggaagctaga gtaagtagtt cgccagttaa    5244
tagtttgcgc aacgttgttg ccattgctac aggcatcgtg gtgtcacgct cgtcgtttgg    5304
tatggcttca ttcagctccg gttcccaacg atcaaggcga gttacatgat cccccatgtt    5364
gtgcaaaaaa gcggttagct ccttcggtcc tccgatcgtt gtcagaagta agttggccgc    5424
agtgttatca ctcatggtta tggcagcact gcataattct cttactgtca tgccatccgt    5484
aagatgcttt tctgtgactg gtgagtactc aaccaagtca ttctgagaat agtgtatgcg    5544
gcgaccgagt tgctcttgcc cggcgtcaat acgggataat accgcgccac atagcagaac    5604
tttaaaagtg ctcatcattg gaaaacgttc ttcggggcga aaactctcaa ggatcttacc    5664
gctgttgaga tccagttcga tgtaacccac tcgtgcaccc aactgatctt cagcatcttt    5724
tactttcacc agcgtttctg ggtgagcaaa aacaggaagg caaaatgccg caaaaaaggg    5784
aataagggcg acacggaaat gttgaatact catactcttc ctttttcaat attattgaag    5844
catttatcag ggttattgtc tcatgagcgg atacatattt gaatgtattt agaaaaataa    5904
acaaataggg gttccgcgca catttccccg aaaagtgcca cctgacgtct aagaaaccat    5964
tattatcatg acattaacct ataaaaatag gcgtatcacg aggccctttc gggtcgcgcg    6024
tttcggtgat gacggtgaaa acctctgaca catgcagctc ccgttgacgg tcacagcttg    6084
tctgtaagcg gatgccggga gcagacaagc ccgtcagggc gcgtcagcgg tgttggcgg    6144 gtgtcggggc tggcttaact atgcggcatc agagcagatt gtactgagag tgcaccataa    6204
aattgtaaac gttaatattt tgttaaaatt cgcgttaaat ttttgttaaa tcagctcatt    6264
ttttaaccaa taggccgaaa tcggcaaaat cccttataaa tcaaaagaat agcccgagat    6324
agggttgagt gttgttccag tttggaacaa gagtccacta ttaaagaacg tggactccaa    6384
cgtcaaaggg cgaaaaaccg tctatcaggg cgatggccca ctacgtgaac catcacccaa    6444
atcaagtttt ttggggtcga ggtgccgtaa agcactaaat cggaaccota aagggagccc    6504 ccgatttaga gcttgacggg gaaagccggc gaacgtggcg agaaaggaag ggaagaaagc    6564
gaaaggagcg ggcgctaggg cgctggcaag tgtagcggtc acgctgcgcg taaccaccac    6624
acccgccgcg cttaatgcgc cgctacaggg cgcgtactat ggttgctttg acgtatgcgg    6684
tgtgaaatac cgcacagatg cgtaaggaga aaataccgca tcaggcgcca ttcgccattc    6744
aggctgcgca actgttggga agggcgatcg gtgcgggcct cttcgctatt acgccagctg    6804
gcgaaagggg gatgtgctgc aaggcgatta agttgggtaa cgccagggtt ttcccagtca    6864
```
cgacgttgta aaacgacggc cagtgaattc catggtctca actttc        6910

<210> SEQ ID NO 16
<211> LENGTH: 676
<212> TYPE: PRT
<213> ORGANISM: Dengue virus

<400> SEQUENCE: 16

```
Met Ser Val Thr Met Leu Leu Met Leu Leu Pro Thr Ala Leu Ala Phe
1               5                   10                  15

His Leu Thr Thr Arg Gly Gly Glu Pro His Met Ile Val Ser Lys Gln
            20                  25                  30

Glu Arg Gly Lys Ser Leu Leu Phe Lys Thr Ser Ala Gly Val Asn Met
        35                  40                  45

Cys Thr Leu Ile Ala Met Asp Leu Gly Glu Leu Cys Glu Asp Thr Met
    50                  55                  60

Thr Tyr Lys Cys Pro Arg Ile Thr Glu Thr Glu Pro Asp Asp Val Asp
65                  70                  75                  80

Cys Trp Cys Asn Ala Thr Glu Thr Trp Val Thr Tyr Gly Thr Cys Ser
                85                  90                  95

Gln Thr Gly Glu His Arg Arg Asp Lys Arg Ser Val Ala Leu Ala Pro
            100                 105                 110

His Val Gly Leu Gly Leu Glu Thr Arg Thr Glu Thr Trp Met Ser Ser
        115                 120                 125

Glu Gly Ala Trp Lys Gln Ile Gln Lys Val Glu Thr Trp Ala Leu Arg
    130                 135                 140

His Pro Gly Phe Thr Val Ile Ala Leu Phe Leu Ala His Ala Ile Gly
145                 150                 155                 160

Thr Ser Ile Thr Gln Lys Gly Ile Ile Phe Ile Leu Leu Met Leu Val
                165                 170                 175

Thr Pro Ser Met Ala Met Arg Cys Val Gly Ile Gly Asn Arg Asp Phe
            180                 185                 190

Val Glu Gly Leu Ser Gly Ala Thr Trp Val Asp Val Val Leu Glu His
        195                 200                 205

Gly Ser Cys Val Thr Thr Met Ala Lys Asp Lys Pro Thr Leu Asp Ile
    210                 215                 220

Glu Leu Leu Lys Thr Glu Val Thr Asn Pro Ala Val Leu Arg Lys Leu
225                 230                 235                 240

Cys Ile Glu Ala Lys Ile Ser Asn Thr Thr Thr Asp Ser Arg Cys Pro
                245                 250                 255

Thr Gln Gly Glu Ala Thr Leu Val Glu Glu Gln Asp Thr Asn Phe Val
            260                 265                 270

Cys Arg Arg Thr Phe Val Asp Arg Gly Trp Gly Asn Gly Cys Gly Leu
        275                 280                 285

Ala Gly Lys Gly Ser Leu Ile Thr Cys Ala Lys Phe Lys Cys Val Thr
    290                 295                 300

Lys Leu Glu Gly Lys Ile Val Gln Tyr Glu Asn Leu Lys Tyr Ser Val
305                 310                 315                 320

Ile Val Thr Val His Thr Gly Asp Gln His Gln Val Gly Asn Glu Thr
                325                 330                 335

Thr Glu His Gly Thr Thr Ala Thr Ile Thr Pro Gln Ala Pro Thr Ser
            340                 345                 350

Glu Ile Gln Leu Thr Asp Tyr Gly Ala Leu Thr Leu Asp Cys Ser Pro
        355                 360                 365
```

```
Arg Thr Gly Leu Asp Phe Asn Glu Met Val Leu Leu Thr Met Glu Lys
        370                 375                 380

Lys Ser Trp Leu Val His Lys Gln Trp Phe Leu Asp Leu Pro Leu Pro
385                 390                 395                 400

Trp Thr Ser Gly Ala Ser Thr Ser Gln Glu Thr Trp Asn Arg Gln Asp
                405                 410                 415

Leu Leu Val Thr Phe Lys Thr Ala His Ala Met Lys Gln Glu Val Val
                420                 425                 430

Val Leu Gly Ser Gln Glu Gly Ala Met His Thr Ala Leu Thr Gly Ala
                435                 440                 445

Thr Glu Ile Gln Thr Ser Gly Thr Thr Thr Ile Phe Ala Gly His Leu
450                 455                 460

Lys Cys Arg Leu Lys Met Asp Lys Leu Thr Leu Lys Gly Met Ser Tyr
465                 470                 475                 480

Val Met Cys Thr Gly Ser Phe Lys Leu Glu Lys Glu Val Ala Glu Thr
                485                 490                 495

Gln His Gly Thr Val Leu Val Gln Val Lys Tyr Glu Gly Thr Asp Ala
                500                 505                 510

Pro Cys Lys Ile Pro Phe Ser Ser Gln Asp Glu Lys Gly Val Thr Gln
                515                 520                 525

Asn Gly Arg Leu Ile Thr Ala Asn Pro Ile Val Thr Asp Lys Glu Lys
530                 535                 540

Pro Val Asn Ile Glu Ala Glu Pro Pro Phe Gly Glu Ser Tyr Ile Val
545                 550                 555                 560

Val Gly Ala Gly Glu Lys Ala Leu Lys Leu Ser Trp Phe Lys Lys Gly
                565                 570                 575

Ser Ser Ile Gly Lys Met Phe Glu Ala Thr Ala Arg Gly Ala Arg Arg
                580                 585                 590

Met Ala Ile Leu Gly Asp Thr Ala Trp Asp Phe Gly Ser Ile Gly Gly
                595                 600                 605

Val Phe Thr Ser Val Gly Lys Leu Ile His Gln Ile Phe Gly Thr Ala
610                 615                 620

Tyr Gly Val Leu Phe Ser Gly Val Ser Trp Thr Met Lys Ile Gly Ile
625                 630                 635                 640

Gly Ile Leu Leu Thr Trp Leu Gly Leu Asn Ser Arg Ser Thr Ser Leu
                645                 650                 655

Ser Met Thr Cys Ile Ala Val Gly Met Val Thr Leu Tyr Leu Gly Val
                660                 665                 670

Met Val Gln Ala
        675

<210> SEQ ID NO 17
<211> LENGTH: 14
<212> TYPE: PRT
<213> ORGANISM: Dengue virus
<220> FEATURE:
<221> NAME/KEY: SIGNAL
<222> LOCATION: (1)..(14)

<400> SEQUENCE: 17

Ser Val Thr Met Leu Leu Met Leu Leu Pro Thr Ala Leu Ala
1               5                   10

<210> SEQ ID NO 18
<211> LENGTH: 91
<212> TYPE: PRT
```

```
<213> ORGANISM: Dengue virus
<220> FEATURE:
<221> NAME/KEY: misc_feature
<222> LOCATION: (1)..(91)
<223> OTHER INFORMATION: pr sequence
<220> FEATURE:
<221> NAME/KEY: misc_feature
<222> LOCATION: (1)..(91)
<223> OTHER INFORMATION: DENV1 pr sequence

<400> SEQUENCE: 18

Phe His Leu Thr Thr Arg Gly Gly Glu Pro His Met Ile Val Ser Lys
1               5                   10                  15

Gln Glu Arg Gly Lys Ser Leu Leu Phe Lys Thr Ser Ala Gly Val Asn
            20                  25                  30

Met Cys Thr Leu Ile Ala Met Asp Leu Gly Glu Leu Cys Glu Asp Thr
        35                  40                  45

Met Thr Tyr Lys Cys Pro Arg Ile Thr Glu Thr Glu Pro Asp Asp Val
    50                  55                  60

Asp Cys Trp Cys Asn Ala Thr Glu Thr Trp Val Thr Tyr Gly Thr Cys
65                  70                  75                  80

Ser Gln Thr Gly Glu His Arg Arg Asp Lys Arg
                85                  90

<210> SEQ ID NO 19
<211> LENGTH: 75
<212> TYPE: PRT
<213> ORGANISM: Dengue virus
<220> FEATURE:
<221> NAME/KEY: MISC_FEATURE
<222> LOCATION: (1)..(75)
<223> OTHER INFORMATION: M sequence
<220> FEATURE:
<221> NAME/KEY: MISC_FEATURE
<222> LOCATION: (1)..(75)
<223> OTHER INFORMATION: DENV1 M sequence

<400> SEQUENCE: 19

Ser Val Ala Leu Ala Pro His Val Gly Leu Gly Leu Glu Thr Arg Thr
1               5                   10                  15

Glu Thr Trp Met Ser Ser Glu Gly Ala Trp Lys Gln Ile Gln Lys Val
            20                  25                  30

Glu Thr Trp Ala Leu Arg His Pro Gly Phe Thr Val Ile Ala Leu Phe
        35                  40                  45

Leu Ala His Ala Ile Gly Thr Ser Ile Thr Gln Lys Gly Ile Ile Phe
    50                  55                  60

Ile Leu Leu Met Leu Val Thr Pro Ser Met Ala
65                  70                  75

<210> SEQ ID NO 20
<211> LENGTH: 495
<212> TYPE: PRT
<213> ORGANISM: Dengue virus
<220> FEATURE:
<221> NAME/KEY: MISC_FEATURE
<222> LOCATION: (1)..(495)
<223> OTHER INFORMATION: DENV1 Envelope sequence

<400> SEQUENCE: 20

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30
```

```
Thr Met Ala Lys Asp Lys Pro Thr Leu Asp Ile Glu Leu Leu Lys Thr
         35                  40                  45
Glu Val Thr Asn Pro Ala Val Leu Arg Lys Leu Cys Ile Glu Ala Lys
 50                  55                  60
Ile Ser Asn Thr Thr Thr Asp Ser Arg Cys Pro Thr Gln Gly Glu Ala
 65                  70                  75                  80
Thr Leu Val Glu Glu Gln Asp Thr Asn Phe Val Cys Arg Arg Thr Phe
                 85                  90                  95
Val Asp Arg Gly Trp Gly Asn Gly Cys Gly Leu Phe Gly Lys Gly Ser
                100                 105                 110
Leu Ile Thr Cys Ala Lys Phe Lys Cys Val Thr Lys Leu Glu Gly Lys
             115                 120                 125
Ile Val Gln Tyr Glu Asn Leu Lys Tyr Ser Val Ile Val Thr Val His
 130                 135                 140
Thr Gly Asp Gln His Gln Val Gly Asn Glu Thr Thr Glu His Gly Thr
 145                 150                 155                 160
Thr Ala Thr Ile Thr Pro Gln Ala Pro Thr Ser Glu Ile Gln Leu Thr
                 165                 170                 175
Asp Tyr Gly Ala Leu Thr Leu Asp Cys Ser Pro Arg Thr Gly Leu Asp
             180                 185                 190
Phe Asn Glu Met Val Leu Leu Thr Met Glu Lys Lys Ser Trp Leu Val
             195                 200                 205
His Lys Gln Trp Phe Leu Asp Leu Pro Leu Pro Trp Thr Ser Gly Ala
 210                 215                 220
Ser Thr Ser Gln Glu Thr Trp Asn Arg Gln Asp Leu Leu Val Thr Phe
225                 230                 235                 240
Lys Thr Ala His Ala Lys Lys Gln Glu Val Val Val Leu Gly Ser Gln
                 245                 250                 255
Glu Gly Ala Met His Thr Ala Leu Thr Gly Ala Thr Glu Ile Gln Thr
             260                 265                 270
Ser Gly Thr Thr Thr Ile Phe Ala Gly His Leu Lys Cys Arg Leu Lys
             275                 280                 285
Met Asp Lys Leu Thr Leu Lys Gly Met Ser Tyr Val Met Cys Thr Gly
 290                 295                 300
Ser Phe Lys Leu Glu Lys Glu Val Ala Glu Thr Gln His Gly Thr Val
305                 310                 315                 320
Leu Val Gln Val Lys Tyr Glu Gly Thr Asp Ala Pro Cys Lys Ile Pro
                 325                 330                 335
Phe Ser Ser Gln Asp Glu Lys Gly Val Thr Gln Asn Gly Arg Leu Ile
             340                 345                 350
Thr Ala Asn Pro Ile Val Thr Asp Lys Glu Lys Pro Val Asn Ile Glu
             355                 360                 365
Ala Glu Pro Pro Phe Gly Glu Ser Tyr Ile Val Val Gly Ala Gly Glu
 370                 375                 380
Lys Ala Leu Lys Leu Ser Trp Phe Lys Lys Gly Ser Ser Ile Gly Lys
385                 390                 395                 400
Met Phe Glu Ala Thr Ala Arg Gly Ala Arg Arg Met Ala Ile Leu Gly
                 405                 410                 415
Asp Thr Ala Trp Asp Phe Gly Ser Ile Gly Gly Val Phe Thr Ser Val
             420                 425                 430
Gly Lys Leu Ile His Gln Ile Phe Gly Thr Ala Tyr Gly Val Leu Phe
             435                 440                 445
Ser Gly Val Ser Trp Thr Met Lys Ile Gly Ile Gly Ile Leu Leu Thr
```

```
                450             455             460
Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Met Val Gln Ala
                485                 490                 495

<210> SEQ ID NO 21
<211> LENGTH: 676
<212> TYPE: PRT
<213> ORGANISM: Dengue virus
<220> FEATURE:
<221> NAME/KEY: INIT_MET
<222> LOCATION: (1)..(1)
<220> FEATURE:
<221> NAME/KEY: SIGNAL
<222> LOCATION: (2)..(15)
<220> FEATURE:
<221> NAME/KEY: MISC_FEATURE
<222> LOCATION: (16)..(106)
<220> FEATURE:
<221> NAME/KEY: MISC_FEATURE
<222> LOCATION: (107)..(181)
<223> OTHER INFORMATION: DENV1 M sequence
<220> FEATURE:
<221> NAME/KEY: MISC_FEATURE
<222> LOCATION: (182)..(676)
<223> OTHER INFORMATION: DENV1 Envelope sequence

<400> SEQUENCE: 21

Met Ser Val Thr Met Leu Leu Met Leu Leu Pro Thr Ala Leu Ala Phe
1               5                   10                  15

His Leu Thr Thr Arg Gly Gly Glu Pro His Met Ile Val Ser Lys Gln
                20                  25                  30

Glu Arg Gly Lys Ser Leu Leu Phe Lys Thr Ser Ala Gly Val Asn Met
            35                  40                  45

Cys Thr Leu Ile Ala Met Asp Leu Gly Glu Leu Cys Glu Asp Thr Met
    50                  55                  60

Thr Tyr Lys Cys Pro Arg Ile Thr Glu Thr Glu Pro Asp Asp Val Asp
65                  70                  75                  80

Cys Trp Cys Asn Ala Thr Glu Thr Trp Val Thr Tyr Gly Thr Cys Ser
                85                  90                  95

Gln Thr Gly Glu His Arg Arg Asp Lys Arg Ser Val Ala Leu Ala Pro
            100                 105                 110

His Val Gly Leu Gly Leu Glu Thr Arg Thr Glu Thr Trp Met Ser Ser
        115                 120                 125

Glu Gly Ala Trp Lys Gln Ile Gln Lys Val Glu Thr Trp Ala Leu Arg
    130                 135                 140

His Pro Gly Phe Thr Val Ile Ala Leu Phe Leu Ala His Ala Ile Gly
145                 150                 155                 160

Thr Ser Ile Thr Gln Lys Gly Ile Ile Phe Ile Leu Leu Met Leu Val
                165                 170                 175

Thr Pro Ser Met Ala Met Arg Cys Val Gly Ile Gly Asn Arg Asp Phe
            180                 185                 190

Val Glu Gly Leu Ser Gly Ala Thr Trp Val Asp Val Val Leu Glu His
        195                 200                 205

Gly Ser Cys Val Thr Thr Met Ala Lys Asp Lys Pro Thr Leu Asp Ile
    210                 215                 220

Glu Leu Leu Lys Thr Glu Val Thr Asn Pro Ala Val Leu Arg Lys Leu
225                 230                 235                 240

Cys Ile Glu Ala Lys Ile Ser Asn Thr Thr Thr Asp Ser Arg Cys Pro
```

-continued

```
                    245                 250                 255
Thr Gln Gly Glu Ala Thr Leu Val Glu Glu Gln Asp Thr Asn Phe Val
                260                 265                 270
Cys Arg Arg Thr Phe Val Asp Arg Gly Trp Gly Asn Gly Cys Gly Leu
                275                 280                 285
Phe Gly Lys Gly Ser Leu Ile Thr Cys Ala Lys Phe Lys Cys Val Thr
                290                 295                 300
Lys Leu Glu Gly Lys Ile Val Gln Tyr Glu Asn Leu Lys Tyr Ser Val
305                 310                 315                 320
Ile Val Thr Val His Thr Gly Asp Gln His Gln Val Gly Asn Glu Thr
                325                 330                 335
Thr Glu His Gly Thr Thr Ala Thr Ile Thr Pro Gln Ala Pro Thr Ser
                340                 345                 350
Glu Ile Gln Leu Thr Asp Tyr Gly Ala Leu Thr Leu Asp Cys Ser Pro
                355                 360                 365
Arg Thr Gly Leu Asp Phe Asn Glu Met Val Leu Leu Thr Met Glu Lys
                370                 375                 380
Lys Ser Trp Leu Val His Lys Gln Trp Phe Leu Asp Leu Pro Leu Pro
385                 390                 395                 400
Trp Thr Ser Gly Ala Ser Thr Ser Gln Glu Thr Trp Asn Arg Gln Asp
                405                 410                 415
Leu Leu Val Thr Phe Lys Thr Ala His Ala Lys Lys Gln Glu Val Val
                420                 425                 430
Val Leu Gly Ser Gln Glu Gly Ala Met His Thr Ala Leu Thr Gly Ala
                435                 440                 445
Thr Glu Ile Gln Thr Ser Gly Thr Thr Thr Ile Phe Ala Gly His Leu
450                 455                 460
Lys Cys Arg Leu Lys Met Asp Lys Leu Thr Leu Lys Gly Met Ser Tyr
465                 470                 475                 480
Val Met Cys Thr Gly Ser Phe Lys Leu Glu Lys Glu Val Ala Glu Thr
                485                 490                 495
Gln His Gly Thr Val Leu Val Gln Val Lys Tyr Glu Gly Thr Asp Ala
                500                 505                 510
Pro Cys Lys Ile Pro Phe Ser Ser Gln Asp Glu Lys Gly Val Thr Gln
                515                 520                 525
Asn Gly Arg Leu Ile Thr Ala Asn Pro Ile Val Thr Asp Lys Glu Lys
                530                 535                 540
Pro Val Asn Ile Glu Ala Glu Pro Pro Phe Gly Glu Ser Tyr Ile Val
545                 550                 555                 560
Val Gly Ala Gly Glu Lys Ala Leu Lys Leu Ser Trp Phe Lys Lys Gly
                565                 570                 575
Ser Ser Ile Gly Lys Met Phe Glu Ala Thr Ala Arg Gly Ala Arg Arg
                580                 585                 590
Met Ala Ile Leu Gly Asp Thr Ala Trp Asp Phe Gly Ser Ile Gly Gly
                595                 600                 605
Val Phe Thr Ser Val Gly Lys Leu Ile His Gln Ile Phe Gly Thr Ala
                610                 615                 620
Tyr Gly Val Leu Phe Ser Gly Val Ser Trp Thr Met Lys Ile Gly Ile
625                 630                 635                 640
Gly Ile Leu Leu Thr Trp Leu Gly Leu Asn Ser Arg Ser Thr Ser Leu
                645                 650                 655
Ser Met Thr Cys Ile Ala Val Gly Met Val Thr Leu Tyr Leu Gly Val
                660                 665                 670
```

```
Met Val Gln Ala
        675

<210> SEQ ID NO 22
<211> LENGTH: 676
<212> TYPE: PRT
<213> ORGANISM: Dengue virus
<220> FEATURE:
<221> NAME/KEY: MISC_FEATURE
<223> OTHER INFORMATION: DEN2 prM E (F108A)_3' DEN1
<220> FEATURE:
<221> NAME/KEY: MISC_FEATURE
<222> LOCATION: (182)..(477)
<223> OTHER INFORMATION: DEN2 prM E (F108A)
<220> FEATURE:
<221> NAME/KEY: MISC_FEATURE
<222> LOCATION: (182)..(477)
<223> OTHER INFORMATION: DEV2 prM E (F108A)
<220> FEATURE:
<221> NAME/KEY: MISC_FEATURE
<222> LOCATION: (478)..(676)
<223> OTHER INFORMATION: 3' DEV1

<400> SEQUENCE: 22

Met Thr Ala Gly Met Ile Ile Met Leu Ile Pro Thr Val Met Ala Phe
1               5                   10                  15

His Leu Thr Thr Arg Asn Gly Glu Pro His Met Ile Val Ser Arg Gln
            20                  25                  30

Glu Lys Gly Lys Ser Leu Leu Phe Lys Thr Lys Asp Gly Thr Asn Met
        35                  40                  45

Cys Thr Leu Met Ala Met Asp Leu Gly Glu Leu Cys Glu Asp Thr Ile
    50                  55                  60

Thr Tyr Lys Cys Pro Phe Leu Lys Gln Asn Glu Pro Glu Asp Ile Asp
65                  70                  75                  80

Cys Trp Cys Asn Ser Thr Ser Thr Trp Val Thr Tyr Gly Thr Cys Thr
                85                  90                  95

Thr Thr Gly Glu His Arg Arg Glu Lys Arg Ser Val Ala Leu Val Pro
            100                 105                 110

His Val Gly Met Gly Leu Glu Thr Arg Thr Glu Thr Trp Met Ser Ser
        115                 120                 125

Glu Gly Ala Trp Lys His Ala Gln Arg Ile Glu Thr Trp Ile Leu Arg
    130                 135                 140

His Pro Gly Phe Thr Ile Met Ala Ala Ile Leu Ala Tyr Thr Ile Gly
145                 150                 155                 160

Thr Thr His Phe Gln Arg Val Leu Ile Phe Ile Leu Leu Thr Ala Ile
                165                 170                 175

Ala Pro Ser Met Thr Met Arg Cys Ile Gly Ile Ser Asn Arg Asp Phe
            180                 185                 190

Val Glu Gly Val Ser Gly Gly Ser Trp Val Asp Ile Val Leu Glu His
        195                 200                 205

Gly Ser Cys Val Thr Thr Met Ala Lys Asn Lys Pro Thr Leu Asp Phe
    210                 215                 220

Glu Leu Ile Lys Thr Glu Ala Lys Gln Pro Ala Thr Leu Arg Lys Tyr
225                 230                 235                 240

Cys Ile Glu Ala Lys Leu Thr Asn Thr Thr Thr Asp Ser Arg Cys Pro
                245                 250                 255

Thr Gln Gly Glu Pro Thr Leu Asn Glu Glu Gln Asp Lys Arg Phe Val
            260                 265                 270

Cys Lys His Ser Met Val Asp Arg Gly Trp Gly Asn Gly Cys Gly Leu
```

```
            275                 280                 285
Ala Gly Lys Gly Gly Ile Val Thr Cys Ala Met Phe Thr Cys Lys Lys
    290                 295                 300

Asn Met Glu Gly Lys Ile Val Gln Pro Glu Asn Leu Glu Tyr Thr Val
305                 310                 315                 320

Val Ile Thr Pro His Ser Gly Glu Glu His Ala Val Gly Asn Asp Thr
            325                 330                 335

Gly Lys His Gly Lys Glu Val Lys Ile Thr Pro Gln Ser Ser Ile Thr
            340                 345                 350

Glu Ala Glu Leu Thr Gly Tyr Gly Thr Val Thr Met Glu Cys Ser Pro
            355                 360                 365

Arg Thr Gly Leu Asp Phe Asn Glu Met Val Leu Leu Gln Met Lys Asp
            370                 375                 380

Lys Ala Trp Leu Val His Arg Gln Trp Phe Leu Asp Leu Pro Leu Pro
385                 390                 395                 400

Trp Leu Pro Gly Ala Asp Thr Gln Gly Ser Asn Trp Ile Gln Lys Glu
                405                 410                 415

Thr Leu Val Thr Phe Lys Asn Pro His Ala Lys Lys Gln Asp Val Val
            420                 425                 430

Val Leu Gly Ser Gln Glu Gly Ala Met His Thr Ala Leu Thr Gly Ala
            435                 440                 445

Thr Glu Ile Gln Met Ser Ser Gly Asn Leu Leu Phe Thr Gly His Leu
    450                 455                 460

Lys Cys Arg Leu Arg Met Asp Lys Leu Gln Leu Lys Gly Met Ser Tyr
465                 470                 475                 480

Val Met Cys Thr Gly Ser Phe Lys Leu Glu Lys Glu Val Ala Glu Thr
                485                 490                 495

Gln His Gly Thr Val Leu Val Gln Val Lys Tyr Glu Gly Thr Asp Ala
                500                 505                 510

Pro Cys Lys Ile Pro Phe Ser Ser Gln Asp Glu Lys Gly Val Thr Gln
            515                 520                 525

Asn Gly Arg Leu Ile Thr Ala Asn Pro Ile Val Thr Asp Lys Glu Lys
    530                 535                 540

Pro Val Asn Ile Glu Ala Glu Pro Pro Phe Gly Glu Ser Tyr Ile Val
545                 550                 555                 560

Val Gly Ala Gly Glu Lys Ala Leu Lys Leu Ser Trp Phe Lys Lys Gly
                565                 570                 575

Ser Ser Ile Gly Lys Met Phe Glu Ala Thr Ala Arg Gly Ala Arg Arg
            580                 585                 590

Met Ala Ile Leu Gly Asp Thr Ala Trp Asp Phe Gly Ser Ile Gly Gly
            595                 600                 605

Val Phe Thr Ser Val Gly Lys Leu Ile His Gln Ile Phe Gly Thr Ala
            610                 615                 620

Tyr Gly Val Leu Phe Ser Gly Val Ser Trp Thr Met Lys Ile Gly Ile
625                 630                 635                 640

Gly Ile Leu Leu Thr Trp Leu Gly Leu Asn Ser Arg Ser Thr Ser Leu
                645                 650                 655

Ser Met Thr Cys Ile Ala Val Gly Met Val Thr Leu Tyr Leu Gly Val
                660                 665                 670

Met Val Gln Ala
            675

<210> SEQ ID NO 23
```

```
<211> LENGTH: 674
<212> TYPE: PRT
<213> ORGANISM: Dengue virus
<220> FEATURE:
<221> NAME/KEY: misc_feature
<223> OTHER INFORMATION: DEV3 prM E (F108A)_3'DEV1
<220> FEATURE:
<221> NAME/KEY: misc_feature
<222> LOCATION: (182)..(475)
<223> OTHER INFORMATION: DEV3 prM E (F108A)
<220> FEATURE:
<221> NAME/KEY: misc_feature
<222> LOCATION: (476)..(676)
<223> OTHER INFORMATION: 3' DEV1

<400> SEQUENCE: 23
```

Met Thr Ser Leu C

```
Gln Gly Val Thr Val Glu Ile Thr Pro Gln Ala Ser Thr Val Glu Ala
                340                 345                 350

Ile Leu Pro Glu Tyr Gly Thr Leu Gly Leu Glu Cys Ser Pro Arg Thr
            355                 360                 365

Gly Leu Asp Phe Asn Glu Met Ile Leu Leu Thr Met Lys Asn Lys Ala
        370                 375                 380

Trp Met Val His Arg Gln Trp Phe Phe Asp Leu Pro Leu Pro Trp Thr
385                 390                 395                 400

Ser Gly Ala Thr Thr Glu Ala Pro Thr Trp Asn Arg Lys Glu Leu Leu
                405                 410                 415

Val Thr Phe Lys Asn Ala His Ala Lys Lys Gln Glu Val Val Val Leu
            420                 425                 430

Gly Ser Gln Glu Gly Ala Met His Thr Ala Leu Thr Gly Ala Thr Glu
        435                 440                 445

Ile Gln Asn Ser Gly Gly Thr Ser Ile Phe Ala Gly His Leu Lys Cys
    450                 455                 460

Arg Leu Lys Met Asp Lys Leu Glu Leu Lys Gly Met Ser Tyr Val Met
465                 470                 475                 480

Cys Thr Gly Ser Phe Lys Leu Glu Lys Glu Val Ala Glu Thr Gln His
                485                 490                 495

Gly Thr Val Leu Val Gln Val Lys Tyr Glu Gly Thr Asp Ala Pro Cys
            500                 505                 510

Lys Ile Pro Phe Ser Ser Gln Asp Glu Lys Gly Val Thr Gln Asn Gly
        515                 520                 525

Arg Leu Ile Thr Ala Asn Pro Ile Val Thr Asp Lys Glu Lys Pro Val
                535                 540

Asn Ile Glu Ala Glu Pro Pro Phe Gly Glu Ser Tyr Ile Val Val Gly
545                 550                 555                 560

Ala Gly Glu Lys Ala Leu Lys Leu Ser Trp Phe Lys Lys Gly Ser Ser
                565                 570                 575

Ile Gly Lys Met Phe Glu Ala Thr Ala Arg Gly Ala Arg Arg Met Ala
            580                 585                 590

Ile Leu Gly Asp Thr Ala Trp Asp Phe Gly Ser Ile Gly Gly Val Phe
        595                 600                 605

Thr Ser Val Gly Lys Leu Ile His Gln Ile Phe Gly Thr Ala Tyr Gly
    610                 615                 620

Val Leu Phe Ser Gly Val Ser Trp Thr Met Lys Ile Gly Ile Gly Ile
625                 630                 635                 640

Leu Leu Thr Trp Leu Gly Leu Asn Ser Arg Ser Thr Ser Leu Ser Met
                645                 650                 655

Thr Cys Ile Ala Val Gly Met Val Thr Leu Tyr Leu Gly Val Met Val
            660                 665                 670

Gln Ala

<210> SEQ ID NO 24
<211> LENGTH: 676
<212> TYPE: PRT
<213> ORGANISM: Dengue virus
<220> FEATURE:
<221> NAME/KEY: MISC_FEATURE
<223> OTHER INFORMATION: DEV4 prM E (F108A)_3'DEV1
<220> FEATURE:
<221> NAME/KEY: MISC_FEATURE
<222> LOCATION: (1)..(477)
<223> OTHER INFORMATION: DEV4 prM E (F108A)
<220> FEATURE:
```

```
<221> NAME/KEY: MISC_FEATURE
<222> LOCATION: (478)..(676)
<223> OTHER INFORMATION: 3' DEV1

<400> SEQUENCE: 24
```

| | | | | | | | | | | | | | | |
|---|---|---|---|---|---|---|---|---|---|---|---|---|---|---|
| Met | Ser | Thr | Val | Thr | Leu | Leu | Cys | Leu | Ile | Pro | Thr | Val | Met | Ala | Phe |
| 1 | | | | 5 | | | | | 10 | | | | | 15 | |
| His | Leu | Ser | Thr | Arg | Asp | Gly | Glu | Pro | Leu | Met | Ile | Val | Ala | Lys | His |
| | | | 20 | | | | | 25 | | | | | 30 | | |
| Glu | Arg | Gly | Arg | Pro | Leu | Leu | Phe | Lys | Thr | Thr | Glu | Gly | Ile | Asn | Lys |
| | | | 35 | | | | | 40 | | | | | 45 | | |
| Cys | Thr | Leu | Ile | Ala | Met | Asp | Leu | Gly | Glu | Met | Cys | Glu | Asp | Thr | Val |
| 50 | | | | | 55 | | | | | 60 | | | | | |
| Thr | Tyr | Lys | Cys | Pro | Leu | Leu | Val | Asn | Thr | Glu | Pro | Glu | Asp | Ile | Asp |
| 65 | | | | | 70 | | | | | 75 | | | | | 80 |
| Cys | Trp | Cys | Asn | Leu | Thr | Ser | Thr | Trp | Val | Met | Tyr | Gly | Thr | Cys | Thr |
| | | | | 85 | | | | | 90 | | | | | 95 | |
| Gln | Asn | Gly | Glu | Arg | Arg | Arg | Glu | Lys | Arg | Ser | Val | Ala | Leu | Thr | Pro |
| | | | 100 | | | | | 105 | | | | | 110 | | |
| His | Ser | Gly | Met | Gly | Leu | Glu | Thr | Arg | Ala | Glu | Thr | Trp | Met | Ser | Ser |
| | | | 115 | | | | | 120 | | | | | 125 | | |
| Glu | Gly | Ala | Trp | Lys | His | Ala | Gln | Arg | Val | Glu | Ser | Trp | Ile | Leu | Arg |
| 130 | | | | | 135 | | | | | 140 | | | | | |
| Asn | Pro | Gly | Phe | Ala | Leu | Leu | Ala | Gly | Phe | Met | Ala | Tyr | Met | Ile | Gly |
| 145 | | | | | 150 | | | | | 155 | | | | | 160 |
| Gln | Thr | Gly | Ile | Gln | Arg | Thr | Val | Phe | Phe | Val | Leu | Met | Met | Leu | Val |
| | | | | 165 | | | | | 170 | | | | | 175 | |
| Ala | Pro | Ser | Tyr | Gly | Met | Arg | Cys | Ile | Gly | Val | Gly | Asn | Arg | Asp | Phe |
| | | | 180 | | | | | 185 | | | | | 190 | | |
| Val | Glu | Gly | Val | Ser | Gly | Gly | Ala | Trp | Val | Asp | Leu | Val | Leu | Glu | His |
| | | | 195 | | | | | 200 | | | | | 205 | | |
| Gly | Gly | Cys | Val | Thr | Thr | Met | Ala | Gln | Gly | Lys | Pro | Thr | Leu | Asp | Phe |
| 210 | | | | | 215 | | | | | 220 | | | | | |
| Glu | Leu | Ile | Lys | Thr | Thr | Ala | Lys | Glu | Val | Ala | Leu | Leu | Arg | Thr | Tyr |
| 225 | | | | | 230 | | | | | 235 | | | | | 240 |
| Cys | Ile | Glu | Ala | Ser | Ile | Ser | Asn | Ile | Thr | Thr | Ala | Thr | Arg | Cys | Pro |
| | | | | 245 | | | | | 250 | | | | | 255 | |
| Thr | Gln | Gly | Glu | Pro | Tyr | Leu | Lys | Glu | Glu | Gln | Asp | Gln | Gln | Tyr | Ile |
| | | | 260 | | | | | 265 | | | | | 270 | | |
| Cys | Arg | Arg | Asp | Val | Val | Asp | Arg | Gly | Trp | Gly | Asn | Gly | Cys | Gly | Leu |
| | | | 275 | | | | | 280 | | | | | 285 | | |
| Ala | Gly | Lys | Gly | Gly | Val | Val | Thr | Cys | Ala | Lys | Phe | Ser | Cys | Ser | Gly |
| 290 | | | | | 295 | | | | | 300 | | | | | |
| Lys | Ile | Thr | Gly | Asn | Leu | Val | Gln | Ile | Glu | Asn | Leu | Glu | Tyr | Thr | Val |
| 305 | | | | | 310 | | | | | 315 | | | | | 320 |
| Val | Val | Thr | Val | His | Asn | Gly | Asp | Thr | His | Ala | Val | Gly | Asn | Asp | Thr |
| | | | | 325 | | | | | 330 | | | | | 335 | |
| Ser | Asn | His | Gly | Val | Thr | Ala | Thr | Ile | Thr | Pro | Arg | Ser | Pro | Ser | Val |
| | | | 340 | | | | | 345 | | | | | 350 | | |
| Glu | Val | Glu | Leu | Pro | Asp | Tyr | Gly | Glu | Leu | Ser | Leu | Asp | Cys | Glu | Pro |
| | | | 355 | | | | | 360 | | | | | 365 | | |
| Arg | Ser | Gly | Ile | Asp | Phe | Asn | Glu | Met | Ile | Leu | Met | Lys | Met | Glu | Lys |
| | | | 370 | | | | | 375 | | | | | 380 | | |
| Lys | Thr | Trp | Leu | Val | His | Lys | Gln | Trp | Phe | Leu | Asp | Leu | Pro | Leu | Pro |

```
385                390                395                400
Trp Thr Ala Gly Ala Asp Thr Ser Glu Val His Trp Asn His Lys Glu
                405                410                415

Arg Met Val Thr Phe Lys Val Pro His Ala Lys Arg Gln Asp Val Thr
                420                425                430

Val Leu Gly Ser Gln Glu Gly Ala Met His Ser Ala Leu Thr Gly Ala
                435                440                445

Thr Glu Val Asp Ser Gly Asp Gly Asn His Met Phe Ala Gly His Leu
                450                455                460

Lys Cys Lys Val Arg Met Glu Lys Leu Arg Ile Lys Gly Met Ser Tyr
465                470                475                480

Val Met Cys Thr Gly Ser Phe Lys Leu Glu Lys Glu Val Ala Glu Thr
                485                490                495

Gln His Gly Thr Val Leu Val Gln Val Lys Tyr Glu Gly Thr Asp Ala
                500                505                510

Pro Cys Lys Ile Pro Phe Ser Ser Gln Asp Glu Lys Gly Val Thr Gln
                515                520                525

Asn Gly Arg Leu Ile Thr Ala Asn Pro Ile Val Thr Asp Lys Glu Lys
                530                535                540

Pro Val Asn Ile Glu Ala Glu Pro Pro Phe Gly Glu Ser Tyr Ile Val
545                550                555                560

Val Gly Ala Gly Glu Lys Ala Leu Lys Leu Ser Trp Phe Lys Lys Gly
                565                570                575

Ser Ser Ile Gly Lys Met Phe Glu Ala Thr Ala Arg Gly Ala Arg Arg
                580                585                590

Met Ala Ile Leu Gly Asp Thr Ala Trp Asp Phe Gly Ser Ile Gly Gly
                595                600                605

Val Phe Thr Ser Val Gly Lys Leu Ile His Gln Ile Phe Gly Thr Ala
                610                615                620

Tyr Gly Val Leu Phe Ser Gly Val Ser Trp Thr Met Lys Ile Gly Ile
625                630                635                640

Gly Ile Leu Leu Thr Trp Leu Gly Leu Asn Ser Arg Ser Thr Ser Leu
                645                650                655

Ser Met Thr Cys Ile Ala Val Gly Met Val Thr Leu Tyr Leu Gly Val
                660                665                670

Met Val Gln Ala
                675
```